US012669416B2

(12) United States Patent
Ishitsuka et al.

(10) Patent No.: US 12,669,416 B2
(45) Date of Patent: Jun. 30, 2026

(54) METHODS AND DEVICES FOR MANIPULATING BIOLOGICAL SAMPLES

(71) Applicant: Singular Genomics Systems, Inc., San Diego, CA (US)

(72) Inventors: Yuji Ishitsuka, San Diego, CA (US); Jaekyung Koh, San Diego, CA (US); Robert James Stover, San Diego, CA (US); Pavel Shekhtmeyster, San Diego, CA (US); Sandor Kovacs, Middletown, DE (US); Hu Cang, San Diego, CA (US); Valeria Rascon, San Diego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 0 days.

(21) Appl. No.: 19/369,905

(22) Filed: Oct. 27, 2025

(65) Prior Publication Data

US 2026/0049908 A1    Feb. 19, 2026

Related U.S. Application Data

(60) Continuation of application No. 19/253,283, filed on Jun. 27, 2025, which is a division of application No.
(Continued)

(51) Int. Cl.
*G01N 1/00* (2006.01)
*G01N 1/28* (2006.01)
(Continued)

(52) U.S. Cl.
CPC ............... *G01N 1/30* (2013.01); *G01N 1/286* (2013.01); *G01N 1/312* (2013.01); *G16B 20/00* (2019.02); *G16B 40/20* (2019.02); *G01N 2001/288* (2013.01); *G01N 2001/305* (2013.01); *G01N 2001/315* (2013.01)

(58) Field of Classification Search
None
See application file for complete search history.

(56) References Cited

U.S. PATENT DOCUMENTS 4,808,521 A    2/1989    Allen
4,814,167 A    3/1989    Wirth et al.
(Continued)

FOREIGN PATENT DOCUMENTS

CA          2909344 A1    10/2014
WO    2016130559 A1     8/2016
(Continued)

OTHER PUBLICATIONS (Jan. 9, 2004) "ANSI SLAS Jan. 2004 (R2012): for Microplates—Footprint Dimensions", Secretariat Society for Laboratory Automation and Screening, 8 pages.
(Continued)

*Primary Examiner* — Jyoti Mutreja
(74) *Attorney, Agent, or Firm* — Mintz, Levin, Cohn, Ferris, Glovsky and Popeo, P.C.; Zachary L. Terranova

(57)        ABSTRACT

Disclosed herein, inter alia, are devices and methods for efficient transfer and analyses of cellular material, tissue samples, such as tissue sections, using carrier substrates and devices.

23 Claims, 23 Drawing Sheets

FFPE block or frozen tissue block

Related U.S. Application Data

18/921,957, filed on Oct. 21, 2024, now Pat. No. 12,416,552, which is a continuation of application No. PCT/US2024/013802, filed on Jan. 31, 2024.

(60) Provisional application No. 63/617,636, filed on Jan. 4, 2024, provisional application No. 63/513,834, filed on Jul. 14, 2023, provisional application No. 63/482,727, filed on Feb. 1, 2023.

(51) Int. Cl.

| | |
|---|---|
| *G01N 1/30* | (2006.01) |
| *G01N 1/31* | (2006.01) |
| *G16B 20/00* | (2019.01) |
| *G16B 40/20* | (2019.01) |

(56) References Cited

U.S. PATENT DOCUMENTS

| | | | |
|---|---|---|---|
| 4,816,253 A | | 3/1989 | Likhite |
| 4,829,012 A | | 5/1989 | Cambiaso et al. |
| 4,882,245 A | | 11/1989 | Gelorme et al. |
| 4,970,276 A | | 11/1990 | Das et al. |
| 5,364,612 A | | 11/1994 | Goldenberg |
| 5,597,725 A | | 1/1997 | Suzuki |
| 5,654,178 A | | 8/1997 | Fitzpatrick et al. |
| 6,444,661 B1 | | 9/2002 | Barton et al. |
| 6,890,740 B2 | | 5/2005 | Robinson |
| 6,897,012 B2 | | 5/2005 | Hada et al. |
| 6,991,888 B2 | | 1/2006 | Padmanaban et al. |
| 7,405,056 B2 | * | 7/2008 | Lam ..................... G01N 1/286 |
| | | | 435/40.52 |
| 7,465,279 B2 | | 12/2008 | Beckman et al. |
| 7,467,632 B2 | | 12/2008 | Lee et al. |
| 10,974,990 B2 | | 4/2021 | Da et al. |
| 11,311,874 B2 | | 4/2022 | Bandara et al. |
| 11,434,525 B2 | | 9/2022 | Glezer |
| 11,492,662 B2 | | 11/2022 | Glezer et al. |
| 11,643,679 B2 | | 5/2023 | Glezer et al. |
| 11,680,288 B2 | | 6/2023 | Glezer |
| 11,753,678 B2 | | 9/2023 | Glezer |
| 12,158,402 B2 | | 12/2024 | Ishitsuka et al. |
| 12,181,388 B2 | | 12/2024 | Ishitsuka et al. |
| 12,298,211 B2 | | 5/2025 | Ishitsuka et al. |
| 12,416,552 B2 | | 9/2025 | Ishitsuka et al. |
| 2002/0164656 A1 | | 11/2002 | Hoeffler et al. |
| 2003/0087985 A1 | | 5/2003 | Hubbell et al. |
| 2005/0288796 A1 | | 12/2005 | Awad et al. |
| 2006/0223122 A1 | | 10/2006 | Fogo et al. |
| 2006/0223197 A1 | | 10/2006 | Vielsack |
| 2006/0234234 A1 | | 10/2006 | Van et al. |
| 2006/0246453 A1 | | 11/2006 | Kato et al. |
| 2008/0000373 A1 | | 1/2008 | Petrucci-Samija et al. |
| 2008/0032328 A1 | | 2/2008 | Cline et al. |
| 2009/0011943 A1 | | 1/2009 | Drmanac et al. |
| 2010/0055733 A1 | | 3/2010 | Lutolf et al. |
| 2010/0136114 A1 | | 6/2010 | Mao |
| 2010/0160478 A1 | | 6/2010 | Nilsson et al. |
| 2011/0021965 A1 | | 1/2011 | Karp et al. |
| 2011/0252935 A1 | | 10/2011 | Welsh |
| 2011/0259744 A1 | | 10/2011 | Moyle |
| 2012/0301886 A1 | | 11/2012 | Farrell et al. |
| 2013/0035248 A1 | | 2/2013 | Icenhour |
| 2013/0040344 A1 | | 2/2013 | Ju |
| 2013/0040843 A1 | | 2/2013 | Von et al. |
| 2013/0040847 A1 | | 2/2013 | Thrippleton et al. |
| 2013/0152710 A1 | | 6/2013 | Laugharn et al. |
| 2014/0335511 A1 | | 11/2014 | Glaser et al. |
| 2015/0079351 A1 | | 3/2015 | Atasoy et al. |
| 2015/0125952 A1 | | 5/2015 | Kim et al. |
| 2016/0116384 A1 | | 4/2016 | Chen et al. |
| 2016/0168650 A1 | | 6/2016 | Kallioniemi et al. |
| 2016/0249891 A1 | | 9/2016 | Gardner et al. |
| 2019/0002971 A1 | | 1/2019 | Koslover et al. |
| 2019/0168210 A1 | | 6/2019 | Anderson |
| 2019/0185620 A1 | | 6/2019 | Gorman et al. |
| 2019/0358312 A1 | | 11/2019 | Irvine et al. |
| 2020/0353120 A1 | | 11/2020 | Zhao et al. |
| 2021/0150707 A1 | | 5/2021 | Weisenfeld et al. |
| 2021/0247316 A1 | | 8/2021 | Bava |
| 2021/0253987 A1 | | 8/2021 | Engler et al. |
| 2023/0266209 A1 | | 8/2023 | Koh et al. |
| 2023/0347021 A1 | | 11/2023 | Koh et al. |
| 2025/0034623 A1 | | 1/2025 | Ishitsuka et al. |
| 2025/0067639 A1 | | 2/2025 | Ishitsuka et al. |
| 2025/0224314 A1 | | 7/2025 | Ishitsuka et al. |
| 2025/0322905 A1 | | 10/2025 | Ishitsuka et al. |

FOREIGN PATENT DOCUMENTS

| | | |
|---|---|---|
| WO | 2020176788 A1 | 9/2020 |
| WO | 2021133845 A1 | 7/2021 |
| WO | 2023076832 A1 | 5/2023 |
| WO | 2024163634 A2 | 8/2024 |

OTHER PUBLICATIONS (Jan. 9, 2004) "ANSI SLAS Feb. 2004 (R2012): for Microplates—Height Dimensions", Secretariat Society for Laboratory Automation and Screening, 9 pages.

(Jan. 9, 2004) "Ansi Slas Mar. 2004 (R2012): for Microplates—Bottom Outside Flange Dimensions", Secretariat Society for Laboratory Automation and Screening, 10 pages.

(Jan. 9, 2004) "ANSI SLAS Apr. 2004 (R2012): for Microplates—Well Positions", Secretariat Society for Laboratory Automation and Screening, 13 pages.

(Apr. 9, 2009) "ANSI SLAS Jun. 2012: for Microplates—Well Bottom Elevation", Secretariat Society for Laboratory Automation and Screening, 9 pages.

Pray et al. (2008) "Eukaryotic Genome Complexity", Nature Education, 1(1):36 (4 Pages).

Extended European Search Report Received in EP Application No. 22888394.8, mailed on Jul. 24, 2025, 17 pages.

"How Many Species of Bacteria Are There", retrieved from http://www.wisegeek.org/how-many-species-of-bacteria-are-there.htm, retrieved on Jan. 21, 2014, 2 pages.

International Search Report and Written Opinion Issued in PCT Application No. PCT/US24/13802, mailed on Sep. 3, 2024, 14 Pages.

International Search Report Issued in PCT Application No. PCT/US22/78462, mailed on Mar. 3, 2023, 22 Pages.

"Oligonucleotide definition", retrieved from Merriam-Webster.com, retrieved on Aug. 23, 2017, 1 page.

(2006) "The Cancer Genome Atlas Program (TCGA)", National Cancer Institute Center for Cancer Genomics, Retrieved from https://www.cancer.gov/ccg/research/genome-sequencing/tcga, 2 pages.

Arce et al. (Jul. 24, 2013) "Fast and Accurate Automated Cell Boundary Determination for Fluorescence Microscopy", Scientific Reports, 3(1):2266 (6 pages).

Paszek et al. (Sep. 2005) "Tensional Homeostasis and the Malignant Phenotype", Cancer cell, 8(3):241-254.

Burgstaller et al. (Jul. 5, 2017) "The Instructive Extracellular Matrix of the Lung: Basic Composition and Alterations in Chronic Lung Disease", European Respiratory Journal, 50(1):1601805 (16 Pages).

Pankova et al. (2019) "RASSF1A Controls Tissue Stiffness and Cancer Stem-Like Cells in Lung Adenocarcinoma", The EMBO journal, 38(13):EMBJ2018100532 (20 Pages).

White Eric S. (2015) "Lung Extracellular Matrix and Fibroblast Function", Annals of the American Thoracic Society, 12:S30-S33.

Ahn et al. (Oct. 1, 2010) "Mechanical Property Characterization of Prostate Cancer Using a Minimally Motorized Indenter in an Ex Vivo Indentation Experiment", Urology, 76(4):1007-1011.

Krupski et al. (2010) "Assessing Mechanical Properties of Benign and Malignant Prostate Tissue", Journal of Clinical Oncology, e15109-e15109.

Zhai et al. (Oct. 2010) "Characterizing the stiffness of Human Prostates using Acoustic Radiation Force", Ultrasonic imaging, 32(4):201-213 (19 Pages).

(56) References Cited

OTHER PUBLICATIONS

Cox et al. (2011) "Remodeling and Homeostasis of the Extracellular Matrix: Implications for Fibrotic Diseases and Cancer", Disease models & mechanisms, 4(2):165-178.

Chen et al. (Jan. 30, 2015) "Expansion Microscopy", Science, 347(6221):543-548 (13 pages).

Carpenter et al. (Oct. 31, 2006) "Cellprofiler: Image Analysis Software for Identifying and Quantifying Cell Phenotypes", Genome Biology, 7(10):R100 (11 pages).

Chen et al. (Apr. 24, 2015) "RNA Imaging. Spatially Resolved, Highly Multiplexed RNA Profiling in Single Cells", Science, 348(6233):aaa6090 (16 pages).

Cai, Matthew Zhipong (2019) "Spatial Mapping of Single Cells in Human Cerebral Cortex Using Dartfish: A Highly Multiplexed Method for in Situ Quantification of Targeted RNA Transcripts", UC San Diego, 108 pages.

Dirks et al. (2004) "Triggered Amplification by Hybridization Chain Reaction", Proceedings of the National Academy of Sciences of the United States of America, 101(43):15275-15278.

Fan et al. (2018) "Branched Rolling Circle Amplification Method for Measuring Serum Circulating MicroRNA Levels for Early Breast Cancer Detection", Cancer Science, 109(9):2897-2906.

Feeney et al. (1982) "Chemical Modification of Proteins: An Overview", American Chemical Society, 198:3-55(53 pages).

Galante et al. (2017) "Sterilization of Hydrogels for Biomedical Applications: A Review", Journal of Biomedical Materials Research Part B, 106(6):2472-2492.

Gao et al. (Mar. 13, 2020) "Comparison of Fresh Frozen Tissue with Formalin-Fixed Paraffin-Embedded Tissue for Mutation Analysis Using a Multi-Gene Panel in Patients with Colorectal Cancer", Frontiers in Oncology, 10:310 (8 pages).

Grokhovsky S.L. (2006) "Specificity of DNA Cleavage by Ultrasound", Molecular Biology, 40(2):276-283.

Haas et al. (Aug. 30, 1999) "Functionalized coating materials based on inorganic- organic polymers", Thin Solid Films, 351(1-2):198-203.

Han et al. (Jun. 2017) "Sterilization, Hydration-dehydration and Tube Fabrication of Zwitterionic Hydrogels", Biointerphases, 12(2):Article 02C411 (7 pages).

Kawamoto et al. (2003) "Use of a New Adhesive Film for the Preparation of Multi-purpose Fresh-frozen Sections From Hard Tissues, Whole-animals, Insects and Plants", Archives of Histology and Cytology, 66(2):123-143.

Koucherian et al. (Sep. 23, 2022) "Fabrication of Multilayer Molds by Dry Film Photoresist", Micromachines, 13(1583): 8 pages.

Lage et al. (Feb. 2003) "Whole Genome Analysis of Genetic Alterations in Small DNA Samples Using Hyperbranched Strand Displacement Amplification And Array-CGH", Genome Research, 13(2):294-307.

Larsson et al. (May 2010) "In Situ Detection and Genotyping of Individual mRNA Molecules", Nature Methods, 7(5):395-397 (5 pages).

Lizardi et al. (Jul. 19, 1998) "Mutation Detection and Single-Molecule Counting Using Isothermal Rolling-Circle Amplification", Nature Genetics, 19(3):225-232.

Magaki et al. (2019) "An Introduction to the Performance of Immunohistochemistry", Methods in Molecular Biology, 1897:289-298.

Mentre Pascale, (2004) "Interfacial Water: A Modulator of Biological Activity", Journal of Biological Physics and Chemistry, 4(2):115-123.

Merriam-Webster, (2024) "A Priori", https://www.merriam-webster.com/dictionary/a%20priori, 1-9 Pages.

Normand et al. (Dec. 1, 2000) "New Insight Into Agarose Gel Mechanical Properties", Biomacromolecules, 1(4):730-738.

Ryu et al. (2019) "Sticker Method for Preparation of Frozen Section Using Adhesive Film", Journal of Neuroscience Methods, 328:108436 (6 pages).

Sansone Alfredo, (Jun. 2019) "Spatial Transcriptomics Levels Up", Nature Methods, 16(6):458 (1 page).

Sy et al. (2019) "Microtomy: Cutting Formalin-Fixed, Paraffin-Embedded Sections", Methods in Molecular Biology, 1897:269-278.

Tanaka Motomu, (Mar. 17, 2020) "Interplays of Interfacial Forces Modulate Structure and Function of Soft and Biological Matters in Aquatic Environments", Frontiers in chemistry, 8:165 (10 pages).

Ticha et al. (2020) "A Novel Cryo-embedding Method for in-depth Analysis of Craniofacial Mini Pig Bone Specimens", Scientific Reports, 10:19510 (11 pages).

Turbett et al. (1997) "The Use of Optimal Cutting Temperature Compound Can Inhibit Amplification by Polymerase Chain Reaction", Diagnostic Molecular Pathology, 6(5):298-303.

Vickovic et al. (Oct. 2019) "High-definition Spatial Transcriptomics for in Situ Tissue Profiling", Nature Methods, 16(10):987-990 (14 pages).

Wang et al. (Mar. 19, 2018) "Multiplexed Imaging of High-density Libraries of RNAs with MERFISH and Expansion Microscopy", Scientific Reports, 8(1):4847 (13 pages).

Wang et al. (Jul. 27, 2018) "Three-dimensional Intact-tissue Sequencing of Single-cell Transcriptional States", Science, 361(6400):eaat5691 (11 pages).

Yang et al. (Mar. 31, 2020) "A Modified Tape Transfer Approach for Rapidly Preparing High-quality Cryosections of Undecalcified Adult Rodent Bones", Journal of Orthopedic Translation, 26:92-100.

* cited by examiner (i)

(ii)

(iii)

(iv)

(i)

(ii)

(iii)

(iv)

Cut sample with punch device(s)

Mount punch device(s) into receiving
array

Mount receiving array on substrate
(microplate or flowcell)

• Receiving array may be flipped to
enable preferred surface to contact the
substrate Push sample out of punch
device(s) using piston rod(s)

Remove receiving array, piston
rod(s), and punch device(s)

605

Transferred tissue
sections

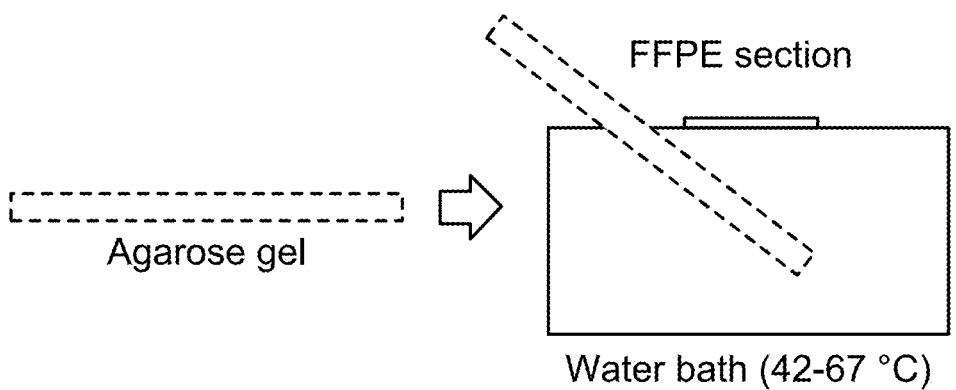
FFPE section
Agarose gel
Water bath (42-67 °C)
FIG. 7A
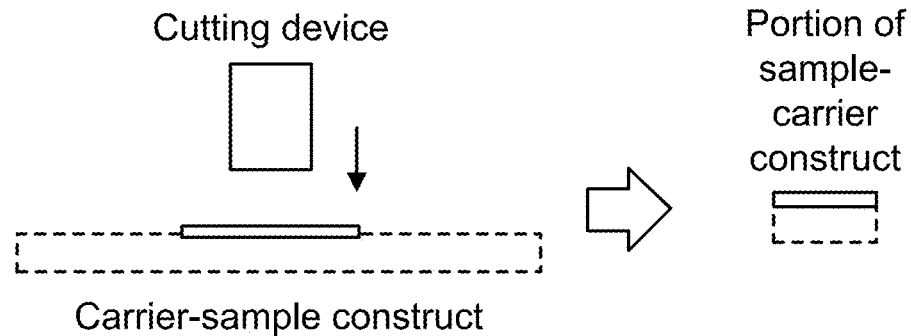
Cutting device
Portion of sample-carrier construct
Carrier-sample construct
FIG. 7B
Mount to slide, heat, and remove agarose gel
Glass
Deparaffinization and analyses
FIG. 7C

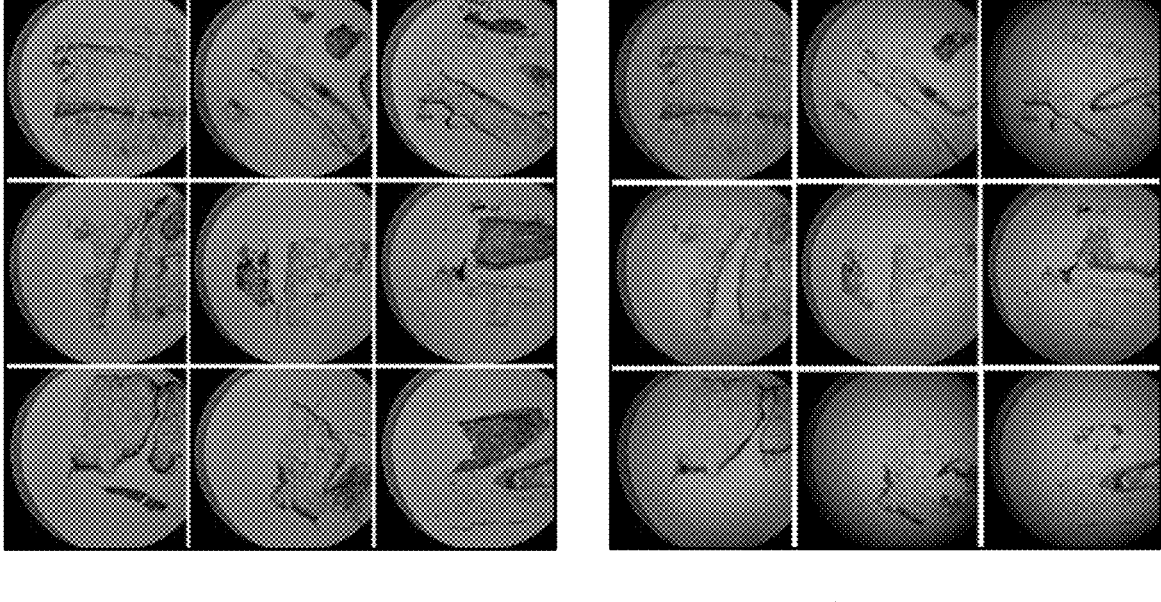
FIG. 8G                    FIG. 8H 96-well    48-well    24-well    12-well Ø 6.5 mm Ø 11 mm Ø 16 mm Ø 22 mm Ø 40 mm 6.5 x 6.5 mm 11 x 11 mm 15 x 36 mm Dia. 10.5mm 10mm x 10mm Dia. 4.5mm 4.5mm x 4.5mm 4.5mm x 10mm 10mm x 17mm Mouse brain          Intermediate surface          Well plate Serial sections in subsequent wells Well-preserved
morphology after transfer Zoomed-in view of H&E

102

101

B

150

101

105

Tissue

101

105

5mm
Carrier substrate

150

101

206

101

204

Step 1
Collect punch device

Step 2
Place punch on the punch tool

Step 3
Orient punch tool on the desired location of the tissue sample and cut the tissue and carrier substrate so a portion of the tissue and carrier are loaded in the punch device Step 4

Eject loaded punch device on piston array and repeat

Step 5

Place all the loaded punch devices on the piston array

Step 6

Align a glass slide affixed to a receiving array with the piston array and allow the pistons to push the carrier substrate

Step 7

Rotate the assembly 180° and heat (e.g., heat to 60°C)

Step 8

Remove piston array, the cutter, and carrier substrate will stick to the piston, leaving the tissue on the glass slide

METHODS AND DEVICES FOR MANIPULATING BIOLOGICAL SAMPLES

CROSS-REFERENCES TO RELATED APPLICATIONS

This application is a continuation application of U.S. patent application Ser. No. 19/253,283, filed Jun. 27, 2025, which is a divisional application of U.S. patent application Ser. No. 18/921,957, filed Oct. 21, 2024, now issued as U.S. Pat. No. 12,416,552, which is a continuation of International Application No. PCT/US2024/013802, filed Jan. 31, 2024, and which claims the benefit of U.S. Provisional Application No. 63/617,636 filed Jan. 4, 2024, U.S. Provisional Application No. 63/513,834 filed Jul. 14, 2023, and U.S. Provisional Application No. 63/482,727, filed Feb. 1, 2023; each of which is incorporated herein by reference in their entirety and for all purposes.

BACKGROUND

Methods for acquiring, preparing, and storing tissue sections for either immediate or future analysis have been largely unchanged for decades. For example, when a patient has a biopsy or surgery, the surgeon often removes a portion of tissue to obtain resected tissue for examination by a pathologist. The resected tissue may then be snap-frozen in liquid nitrogen shortly after surgical resection, generating what is commonly referred to as "fresh frozen" tissue. Alternatively, the resected tissue may be preserved in formaldehyde, embedded in paraffin wax, and optionally stored at room temperature, referred to as formalin-fixation and paraffin embedding (FFPE). Both preservation methods are widely used for preserving the macroscopic architecture of cellular structures (e.g., preserve tissue architecture, cell shape, and the components of the cell, such as proteins, DNA, RNA, carbohydrates, and enzymes) in tissue sections. Once a tissue sample has been prepared (e.g., either a fresh frozen sample or FFPE tissue block), a pathologist typically slices the tissue sample into very thin sections (e.g., sectioning using a cryotome, vibratome, or microtome) that are then placed on a glass slide and examined under a microscope. In recent years with the development of additional technologies to further analyze the sample (e.g., spatial gene expression and/or proteomic analyses), extracting or transferring the sample from a glass slide/transitional surface to another medium would be an attractive step in the processing of tissue samples. However, subsequent transfer and/or manipulation of the tissue section to another surface often introduces additional damage to the sample. For example, once the tissue section is attached to the first surface (e.g., a typical biopsy slide, such as functionalized and/or a charged glass surface), it may be extremely difficult to transfer again without damaging the tissue due to strong contact forces between the tissue section and attachment surface. Novel approaches for transferring biological specimens while minimizing damage are needed. Disclosed herein, inter alia, are solutions to these and other problems in the art.

BRIEF SUMMARY

In an aspect is provided a system for manipulating a biological sample. In embodiments, the system includes a punch device configured to form a sample portion of the biological sample, the punch device forming an internal cavity (e.g., the punch device includes shaft) and having a bottom edge sufficiently sharp to cut through the biological sample; a receiving substrate; and a piston sized and shaped to fit within the internal cavity of the punch device, wherein the piston inserts into the internal cavity of the punch device to expel the sample portion (e.g., all or a portion thereof) from the punch device onto the receiving substrate.

In embodiments, the system includes a punch device configured to form a sample portion of the biological sample, the punch device forming an internal cavity and having a bottom edge sufficiently sharp to cut through the biological sample; a receiving array having a receptacle sized and shaped to receive at least a portion of the punch device; a piston array having a piston sized and shaped to fit within the internal cavity of the punch device, wherein the piston inserts into the internal cavity of the punch device to expel the sample portion from the punch device into the at least one receptacle of the receiving array.

BRIEF DESCRIPTION OF THE DRAWINGS

FIG. 2A depicts a sample-carrier construct (i) wherein the sample is embedded in an embedding material, e.g., paraffin wax. The embedding material may be removed, for example when the embedding material is paraffin wax by contacting the construct with an organic solvent such as xylene or heptane, leaving the biological sample on the construct. Alternatively, the sample-carrier construct may be subjected to fluorogenic and/or chromogenic counterstaining (e.g., H&E staining) methods to aid in visualization and identifying details of the cell types, organelles, structures in the tissue section. In embodiments, selected removal of one or more portions of the construct may occur. To a sample-carrier construct, illustrated in step (i), one or more portions of the construct are removed or cut-out, for example using a cutting device, and depicted as circular dashed lines in step (ii). As described further herein, the shape can vary (e.g., square, rectangular, etc.) The resulting portions of the construct (shown as cylindrical bodies although the shape can vary), illustrated in step (iii), may then be placed into one or more wells of a multiwell container (e.g., a 96-well microplate), such that the biological sample of the portion is in contact with the bottom of the receiving substrate (i.e., well), as shown in step (iv) of FIG. 2A. FIG. 2B shows similar steps (i) though (iv) wherein the biological sample of the portion is positioned in contact with the bottom of the receiving substrate.

FIG. 5B shows a plunging device (i.e., piston array 206) comprising a base (205) and a collection of rods (204) extending from the base (205) wherein the rods 204 serve as pistons or pushers. In embodiments, the piston array includes the same structural and spatial configuration as the receiving array such that when the piston array contacts the sample within the retrained punch devices, the sample is expelled from the within the punch devices. FIG. 5C depicts a cross-section assembly of the piston array 206, loaded with a punch device (101). In embodiments, the piston (204) inserts into the loaded punch device and contacts the carrier substrate (105) to push the loaded portion of the sample (106) out of the punch device. The top (103) of the punch device is in contact with the glass slide (300). In embodiments, the receiving array (200) orients a plurality of punch devices in a repro-ducible pattern (e.g., a pattern of samples illustrated in FIG. 9C).

FIGS. 7A-7C presents a diagram of using a carrier sub-strate for capture and transfer of a tissue section onto a glass substrate (e.g., a well of a multiwell carrier). In this embodi-ment, the carrier substrate is an agarose gel and is prepared and placed in a warm water bath (e.g., maintained at a temperature between 42° C. and 67° C.), as shown in FIG. 7A. An FFPE tissue section floats in the water bath, followed by contacting the tissue section with the agarose gel to layer it atop the agarose. In embodiments, the carrier substrate maintains a hydrated interfacial surface (i.e., a plurality of water molecules at the surface forming an interstitial water layer) between the tissue section and the carrier substrate. Without being bound by any theory, the interfacial water is useful at facilitating transfer and does not significantly affect the structural integrity of the tissue section upon subsequent transfer. The tissue section and agarose gel (collectively referred to as a sample-carrier construct) are removed from the warm water bath and allowed to cool without completely drying out. A portion of the construct is removed, for example using a cutting device, e.g., a hole punch or cutting blade as described herein. Multiple portions may be made from a single tissue section. The portions (i.e., cutouts) are then mounted onto a functionalized glass slide by bringing the tissue section in contact with the glass surface. The glass, tissue section, and agarose may then heated (e.g., heated to 30° C.-70° C.) to facilitate removal of the agarose gel while retaining the tissue section on the glass surface. Alterna-tively, the agarose gel is physically removed (e.g., with forceps or tweezers).

FIGS. 8A-8H are images of H&E-stained tissue sections mounted on functionalized glass slides in a 96-well plate and subjected to 18 cycles of heat and chemical treatment, consistent with DNA sequencing reaction conditions, referred to as tissue integrity tests. FIG. 8A shows tissue sections mounted on an APTES-functionalized wells; and FIG. 8B shows the same tissue sections after the 18 cycles of tissue integrity testing. FIG. 8C shows tissue sections mounted on a (5,6-epoxyhexyl)triethoxysilane (EHTES)-functionalized slide, and FIG. 8D shows the same tissue sections after the 18 cycles of tissue integrity testing. FIG. 8E shows tissue sections mounted on an EHTES and poly-ethyleneimine (PEI)-functionalized slide, and FIG. 8F shows the same tissue sections after the 18 cycles of tissue integrity testing. FIG. 8G shows tissue sections mounted on a PEI-functionalized slide, and FIG. 8H shows the same tissue sections after the 18 cycles of tissue integrity testing.

FIG. 9C illustrates different embodiments of punch devices, with the internal dimensions shown below each embodiment of a punch device. Adjacent to the punch device illustrations are examples of tissue placement on a four-channel flow cell. For example, a square punch device with internal dimen-sions 10 mm by 10 mm results in ten distinct 10 mm×10 mm tissue samples arranged on a flow cell. Typical flow cells include a 75 mm×25 mm glass slide, with fluidic channels formed via a channel spacer, and a cover slip affixed to the channel spacer. FIG. 9D shows transferred FFPE tissue sections on a four channel flow cell with circular (left) and rectangular (right) cutters. In embodiments, when utilizing a receiving array, the plurality of punch devices are arranged in a reproducible pattern (e.g., a pattern of samples illustrated in FIG. 9C). Alternatively, the punch devices may be applied to the glass slide in a custom manner (e.g., random order) depicted in FIG. 9D.

FIG. 10A provides a microplate (e.g., a container including 96 wells) with 96 mouse brain tissue sections arranged using the methods described herein. A neonatal mouse brain paraffin block in coronal orientation was sectioned in 5 μm sections. The arranged tissue sections represent approximately 500 μm in the z axis of the tissue. In this embodiment, H&E staining of the mouse brain sections occurred following transfer to the microplate. FIG. 10B provides images of the first three wells and an expanded view of three different regions within one the brain sections demonstrating the transfer methods described herein do not compromise the integrity of the tissue structures.

FIG. 17C illustrates that the assembly may be inverted (or turned over) to aid forcing the biological sample to remain in contact with the receiving substrate. Following incubation on a heat plate, the receiving array, pistons, and punch devices are removed such that the sample (e.g., the tissue section) is retained on the substrate. A plurality of samples may be loaded according to the workflow illustrated herein.

DETAILED DESCRIPTION

Figure 1:
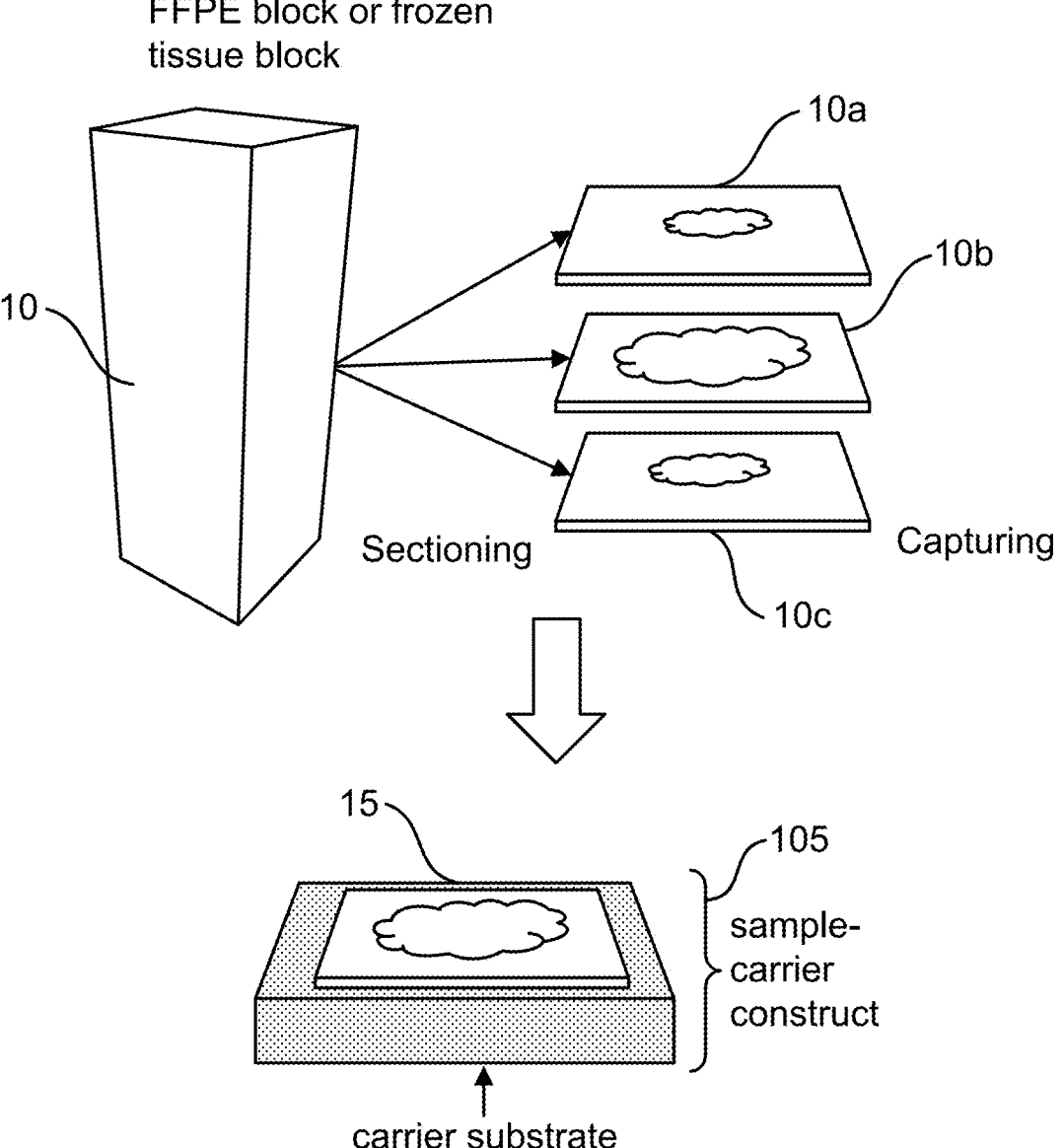
FIG. 1 schematically depicts a process for generating sections and subsequent capture of a biological sample. A sample block, either an FFPE block (i.e., a paraffin embedded biological sample) or fresh frozen tissue block containing a biological sample, is sliced into very thin sections, referred to as sectioning. Individual sections are then captured using a carrier substrate to generate a sample-carrier construct formed of a sample portion positioned on, atop or otherwise coupled to a carrier substrate.

The aspects and embodiments described herein relate to the transfer and manipulation of biological samples (e.g., tissue sections). As described herein, the methods and compositions of this disclosure have many advantages, including greatly enhanced efficiency and speed for tissue testing; and greatly decreased cost for multiple tissue testing.

I. Definitions

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise. Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

In the description, relative terms such as "before," "after," "above," "below," "up," "down," "top" and "bottom" as well as derivative thereof (e.g., "horizontally," "downwardly," "upwardly," etc.) should be construed to refer to the orientation as then described or as shown in the drawing or figure under discussion. These relative terms are for convenience of description and do not require that the system be constructed or operated in a particular orientation.

As used herein, the term "contacting" is used in accordance with its plain ordinary meaning and refers to the process of allowing at least two distinct species (e.g., chemical compounds, biomolecules, nucleotides, binding reagents, or cells) to become sufficiently proximal to react, interact or physically touch. However, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound, a protein (e.g., an antibody), substrate, device, or enzyme.

As may be used herein, the terms "nucleic acid," "nucleic acid molecule," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may include natural nucleic acid sequences and variants thereof, artificial nucleic acid sequences, or a combination of such sequences. As may be used herein, the terms "nucleic acid oligomer" and "oligonucleotide" are used interchangeably and are intended to include, but are not limited to, nucleic acids having a length of 200 nucleotides or less. In some embodiments, an oligonucleotide is a nucleic acid having a length of 2 to 200 nucleotides, 2 to 150 nucleotides, 5 to 150 nucleotides or 5 to 100 nucleotides. The terms "polynucleotide," "oligonucleotide," "oligo" or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. In some embodiments, an oligonucleotide is a primer configured for extension by a polymerase when the primer is annealed completely or partially to a complementary nucleic acid template. A primer is often a single stranded nucleic acid. In certain embodiments, a primer, or portion thereof, is substantially complementary to a portion of an adapter. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. In some embodiments, an oligonucleotide may be immobilized to a solid support.

The term "messenger RNA" or "mRNA" refers to an RNA that is without introns and is capable of being translated into a polypeptide. The term "RNA" refers to any ribonucleic acid, including but not limited to mRNA, tRNA (transfer RNA), rRNA (ribosomal RNA), and/or noncoding RNA (such as lncRNA (long noncoding RNA)). The term "cDNA" refers to a DNA that is complementary or identical to an RNA, in either single stranded or double stranded form.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

In some embodiments, a nucleic acid includes a label. As used herein, the term "label" or "labels" is used in accordance with their plain and ordinary meanings and refer to molecules that can directly or indirectly produce or result in a detectable signal either by themselves or upon interaction with another molecule. Non-limiting examples of detectable labels include fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the label is a dye. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.). In embodiments, a particular nucleotide type is associated with a particular label, such that identifying the label identifies the nucleotide with which it is associated. In embodiments, the label is luciferin that reacts with luciferase to produce a detectable signal in response to one or more bases being incorporated into an elongated complementary strand, such as in pyrosequencing. In embodiment, a nucleotide includes a label (such as a dye). In embodiments, the label is not associated with any particular nucleotide, but detection of the label identifies whether one or more nucleotides having a known identity were added during an extension step (such as in the case of pyrosequencing). Examples of detectable agents (i.e., labels) include imaging agents, including fluorescent and luminescent substances, molecules, or compositions, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). The term "cyanine" or "cyanine moiety" as described herein refers to a detectable moiety containing two nitrogen groups separated by a polymethine chain. In embodiments, the cyanine moiety has 3 methine structures (i.e., cyanine 3 or Cy3). In embodiments, the cyanine moiety has 5 methine structures (i.e., cyanine 5 or Cy5). In embodiments, the cyanine moiety has 7 methine structures (i.e., cyanine 7 or Cy7).

As used herein, the term "biomolecule" refers to an agent (e.g., a compound, macromolecule, or small molecule), and the like derived from a biological system (e.g., an organism). The biomolecule may contain multiple individual components that collectively construct the biomolecule, for example, in embodiments, the biomolecule is a polynucleotide wherein the polynucleotide is composed of nucleotide monomers. The biomolecule may be or may include DNA, RNA, organelles, carbohydrates, lipids, proteins, or any combination thereof. These components may be extracellular. In some examples, the biomolecule may be referred to as a clump or aggregate of combinations of components. In some instances, the biomolecule may include one or more constituents of a cell but may not include other constituents of the cell. In embodiments, a biomolecule is a molecule produced by a biological system (e.g., an organism). In embodiments, a biomolecule may be referred to as an analyte. Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In embodiments, the analytes within a cell can be localized to subcellular locations, including, for example, organelles, e.g., mitochondria, Golgi apparatus, endoplasmic reticulum, chloroplasts, endocytic vesicles, exocytic vesicles, vacuoles, lysosomes, etc. In embodiments, analyte(s) can be peptides or proteins, including antibodies and/or enzymes. In embodiments, an analyte can be detected indirectly, such as through detection of an intermediate agent, for example, a ligation product or an analyte capture agent (e.g., an oligonucleotide-conjugated antibody), such as those described herein.

As used herein, the term "biological system" refers to a virus, cell, cell derivative, cell nucleus, cell organelle, cell constituent and the like derived from a biological sample. Examples of a cell organelle include, without limitation, a nucleus, endoplasmic reticulum, a ribosome, a Golgi apparatus, an endoplasmic reticulum, a chloroplast, an endocytic vesicle, an exocytic vesicle, a vacuole, and a lysosome. The biological system (e.g., an organism) may contain multiple individual components, such as viruses, cells, cell derivatives, cell nuclei, cell organelles and cell constituents, including combinations of different of these and other components. The biological system may include DNA, RNA, organelles, proteins, or any combination thereof. These components may be extracellular. In some examples, the biological system may be referred to as a clump or aggregate of combinations of components. In some instances, the biological system may include one or more constituents of a cell but may not include other constituents of the cell. An example of such constituents include nucleus or an organelle. A cell may be a live or viable cell. The live cell may be capable of being cultured, for example, being cultured when enclosed in a gel or polymer matrix or cultured when including a gel or polymer matrix. A biological system may include a single cell and/or a single nuclei from a cell.

As used herein, the term "polymer" refers to macromolecules having one or more structurally unique repeating units. The repeating units are referred to as "monomers," which are polymerized for the polymer. Typically, a polymer is formed by monomers linked in a chain-like structure. A polymer formed entirely from a single type of monomer is referred to as a "homopolymer." A polymer formed from two or more unique repeating structural units may be referred to as a "copolymer." A polymer may be linear or branched, and may be random, block, polymer brush, hyperbranched polymer, bottlebrush polymer, dendritic polymer, or polymer micelles. The term "polymer" includes homopolymers, copolymers, tripolymers, tetra polymers and other polymeric molecules made from monomeric subunits. Copolymers include alternating copolymers, periodic copolymers, statistical copolymers, random copolymers, block copolymers, linear copolymers and branched copolymers. The term "polymerizable monomer" is used in accordance with its meaning in the art of polymer chemistry and refers to a compound that may covalently bind chemically to other monomer molecules (such as other polymerizable monomers that are the same or different) to form a polymer.

Polymers can be hydrophilic, hydrophobic or amphiphilic, as known in the art. Thus, "hydrophilic polymers" are substantially miscible with water and include, but are not limited to, polyethylene glycol and the like. "Hydrophobic polymers" are substantially immiscible with water and include, but are not limited to, polyethylene, polypropylene, polybutadiene, polystyrene, polymers disclosed herein, and the like. "Amphiphilic polymers" have both hydrophilic and hydrophobic properties and are typically copolymers having hydrophilic segment(s) and hydrophobic segment(s). Polymers include homopolymers, random copolymers, and block copolymers, as known in the art. The term "homopolymer" refers, in the usual and customary sense, to a polymer having a single monomeric unit. The term "copolymer" refers to a polymer derived from two or more monomeric species. The term "random copolymer" refers to a polymer derived from two or more monomeric species with no preferred ordering of the monomeric species. The term "block copolymer" refers to polymers having two or homopolymer subunits linked by covalent bond. Thus, the term "hydrophobic homopolymer" refers to a homopolymer which is hydrophobic. The term "hydrophobic block copolymer" refers to two or more homopolymer subunits linked by covalent bonds and which is hydrophobic.

A "receiving substrate" is used according to its plain and ordinary meaning and generally refers to a substantially solid construct with a surface that functions to support a tissue section. A receiving substrate may be composed of any appropriate material such as metal, plastic, glass or polymer based materials.

As used herein, the term "hydrogel" or "hydrogel carrier" refers to a three-dimensional polymeric structure that is substantially insoluble in water, but which is capable of absorbing and retaining water (e.g. large quantities of water) to form a substantially stable, often soft and pliable, structure. In embodiments, water can penetrate in between polymer chains of a polymer network, subsequently causing swelling and the formation of a hydrogel. In embodiments, hydrogels are super-absorbent (e.g., containing more than about 90% water) and can be comprised of natural or synthetic polymers. Hydrogels can contain over 99% water and may include natural or synthetic polymers, or a combination thereof. Hydrogels also possess a degree of flexibility very similar to natural tissue, due to their significant water content. A detailed description of suitable hydrogels may be found in published U.S. patent application 20100055733, herein specifically incorporated by reference. By "hydrogel subunits" or "hydrogel precursors" is meant hydrophilic monomers, prepolymers, or polymers that can be crosslinked, or "polymerized", to form a three-dimensional (3D) hydrogel network.

Hydrogels may be prepared by cross-linking hydrophilic biopolymers or synthetic polymers. Thus, in some embodiments, the hydrogel may include a crosslinker. As used herein, the term "crosslinker" refers to a molecule that can form a three-dimensional network when reacted with the appropriate base monomers. Examples of the hydrogel polymers, which may include one or more crosslinkers, include but are not limited to, hyaluronans, chitosans, agar, heparin, sulfate, cellulose, alginates (including alginate sulfate), collagen, dextrans (including dextran sulfate), pectin, carrageenan, polylysine, gelatins (including gelatin type A), agarose, (meth)acrylate-oligolactide-PEO-oligolactide-(meth)acrylate, PEO-PPO-PEO copolymers (Pluronics), poly(phosphazene), poly(methacrylates), poly(N-vinylpyrrolidone), PL(G)A-PEO-PL(G)A copolymers, poly(ethylene imine), polyethylene glycol (PEG)-thiol, PEG-acrylate, acrylamide, N,N'-bis(acryloyl)cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetracrylate, or combinations thereof. Thus, for example, a combination may include a polymer and a crosslinker, for example polyethylene glycol (PEG)-thiol/PEG-acrylate, acrylamide/N,N'-bis(acryloyl)cystamine (BACy), or PEG/polypropylene oxide (PPO). In embodiments, the hydrogel includes chemical crosslinks (e.g., intermolecular or intramolecular joining of two or more molecules by a covalent bond) and may be referred to as a chemical hydrogel. In embodiments, the hydrogel includes physical crosslinks (e.g., intermolecular or intramolecular joining of two or more molecules by a non-covalent bond) and may be referred to as a physical hydrogel. In embodiments, the physical hydrogel include one or more crosslinks including hydrogen bonds, hydrophobic interactions, and/or polymer chain entanglements.

As used herein, the term "interfacial", or "interfacial layer", is used in accordance with its plain ordinary meaning and refers to the boundary between any two bulk phases (gas, liquid, or solid) in contact where the properties differ from the properties of the bulk phases. In embodiments, an interfacial layer includes water. Interfacial water differs from bulk water in a number of properties, for example, interfacial water has a higher heat capacity than bulk water because more energy is necessary to break its hydrogen bonds. The arrangement and structure of the interfacial water layer varies depending on the structure of the hydrophilic and/or hydrophobic surface(s) the water layer is in contact with. Additional properties of interfacial water may be found in, e.g., Mentre P. J. Biol. Phys. and Chem. 2004; 4: 115-123 and Tanaka M. Front. Chem. 2020; 8:165, which are incorporated herein by reference in their entirety.

As used herein, the terms "solid support" and "substrate" and "substrate surface" and "solid surface" refers to discrete solid or semi-solid surfaces to which a plurality of functional groups (e.g., bioconjugate reactive moieties or specific binding reagents) may be attached. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A solid support may include a discrete particle that may be spherical (e.g., microspheres) or have a non-spherical or irregular shape, such as cubic, cuboid, pyramidal, cylindrical, conical, oblong, or disc-shaped, and the like. A bead can be non-spherical in shape. A solid support may be used interchangeably with the term "bead." A solid support may further include a polymer or hydrogel on the surface to which the primers are attached. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. Particularly useful solid supports for some embodiments have at least one surface located on a microplate. Solid surfaces can also be varied in their shape depending on the application in a method described herein. For example, a solid surface useful herein can be planar, or contain regions which are concave or convex. In embodiments, the geometry of the concave or convex regions (e.g., wells) of the solid surface conform to the size and shape of a substantially circular particle to maximize the contact between the particle. In embodiments, the wells of an array are randomly located such that nearest neighbor wells have random spacing between each other. Alternatively, in embodiments the spacing between the wells can be ordered, for example, forming a regular pattern. The term solid substrate is encompassing of a substrate (e.g., a microplate) having a surface including a polymer coating covalently attached thereto.

The term "microplate", "microtiter plate", "multiwell container", or "multiwell plate" as used herein, refers to a substrate including a surface, the surface including a plurality of reaction chambers separated from each other by interstitial regions on the surface. In embodiments, the microplate has dimensions as provided and described by American National Standards Institute (ANSI) and Society for Laboratory Automation And Screening (SLAS); for example the tolerances and dimensions set forth in ANSI SLAS 1-2004 (R2012); ANSI SLAS 2-2004 (R2012); ANSI SLAS 3-2004 (R2012); ANSI SLAS 4-2004 (R2012); and ANSI SLAS 6-2012, which are incorporated herein by reference. The dimensions of the microplate as described herein and the arrangement of the reaction chambers may be compatible with an established format for automated laboratory equipment. In embodiments, the device described herein provides methods for high-throughput screening. High-throughput screening (HTS) refers to a process that uses a combination of modern robotics, data processing and control software, liquid handling devices, and/or sensitive detectors, to efficiently process a large amount of (e.g., thousands, hundreds of thousands, or millions) samples in biochemical, genetic, or pharmacological experiments, either in parallel or in sequence, within a reasonably short period of time (e.g., days). Preferably, the process is amenable to automation, such as robotic simultaneous handling of 96 samples, 384 samples, 1536 samples or more. A typical HTS robot tests up to 100,000 to a few hundred thousand compounds per day. The samples are often in small volumes, such as no more than 1 mL, 500 µl, 200 µl, 100 µl, 50 µl or less. Through this process, one can rapidly identify active compounds, small molecules, antibodies, proteins or polynucleotides in a cell.

The reaction chambers may be provided as wells (alternatively referred to as reaction chambers), for example a microplate may contain 2, 4, 6, 12, 24, 48, 96, 384, or 1536 sample wells. In embodiments, the 96 and 384 wells are arranged in a 2:3 rectangular matrix. In embodiments, the 24 wells are arranged in a 3:8 rectangular matrix. In embodiments, the 48 wells are arranged in a 3:4 rectangular matrix. In embodiments, the reaction chamber is a microscope slide (e.g., a glass slide about 75 mm by about 25 mm). In embodiments the slide is a concavity slide (e.g., the slide includes a depression). In embodiments, the slide includes a coating for enhanced cell adhesion (e.g., poly-L-lysine, silanes, carbon nanotubes, polymers, epoxy resins, or gold). In embodiments, the microplate is about 5 inches by about 3.33 inches, and includes a plurality of 5 mm diameter wells. In embodiments, the microplate is about 5 inches by about 3.33 inches, and includes a plurality of 6 mm diameter wells. In embodiments, the microplate is about 5 inches by about 3.33 inches, and includes a plurality of 7 mm diameter wells. In embodiments, the microplate is about 5 inches by about 3.33 inches, and includes a plurality of 7.5 mm diameter wells. In embodiments, the microplate is 5 inches by 3.33 inches, and includes a plurality of 7.5 mm diameter wells. In embodiments, the microplate is about 5 inches by about 3.33 inches, and includes a plurality of 8 mm diameter wells. In embodiments, the microplate is a flat glass or plastic tray in which an array of wells are formed, wherein each well can hold between from a few microliters to hundreds of microliters of fluid reagents and samples.

The term "surface" is intended to mean an external part or external layer of a substrate. The surface can be in contact with another material such as a gas, liquid, gel, polymer, organic polymer, second surface of a similar or different material, metal, or coat. The surface, or regions thereof, can be substantially flat. The substrate and/or the surface can have surface features such as wells, pits, channels, ridges, raised regions, pegs, posts or the like.

The term "well" refers to a discrete concave feature in a substrate having a surface opening that is completely surrounded by interstitial region(s) of the surface. Wells can have any of a variety of shapes at their opening in a surface including but not limited to round, elliptical, square, polygonal, or star shaped (i.e., star shaped with any number of vertices). The cross section of a well taken orthogonally with the surface may be curved, square, polygonal, hyperbolic, conical, or angular. The wells of a microplate are available in different shapes, for example F-Bottom: flat bottom; C-Bottom: bottom with minimal rounded edges; V-Bottom: V-shaped bottom; or U-Bottom: U-shaped bottom. In embodiments, the well is substantially square. In embodiments, the well is square. In embodiments, the well is F-bottom. In embodiments, the microplate includes 24 substantially round flat bottom wells. In embodiments, the microplate includes 48 substantially round flat bottom wells. In embodiments, the microplate includes 96 substantially round flat bottom wells. In embodiments, the microplate includes 384 substantially square flat bottom wells.

The discrete regions (i.e., features, wells) of the microplate may have defined locations in a regular array, which may correspond to a rectilinear pattern, circular pattern, hexagonal pattern, or the like. In embodiments, the pattern of wells includes concentric circles of regions, spiral patterns, rectilinear patterns, hexagonal patterns, and the like. In embodiments, the pattern of wells is arranged in a rectilinear or hexagonal pattern A regular array of such regions is advantageous for detection and data analysis of signals collected from the arrays during an analysis. These discrete regions are separated by interstitial regions. As used herein, the term "interstitial region" refers to an area in a substrate or on a surface that separates other areas of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In embodiments the interstitial region is continuous whereas the features are discrete, for example, as is the case for an array of wells in an otherwise continuous surface. The separation provided by an interstitial region can be partial or full separation. In embodiments, interstitial regions have a surface material that differs from the surface material of the wells (e.g., the interstitial region contains a photoresist and the surface of the well is glass). In embodiments, interstitial regions have a surface material that is the same as the surface material of the wells (e.g., both the surface of the interstitial region and the surface of well contain a polymer or copolymer).

The terms "bind" and "bound" as used herein are used in accordance with their plain and ordinary meanings and refer to an association between atoms or molecules. The association can be direct or indirect. For example, bound atoms or molecules may be directly bound to one another, e.g., by a covalent bond or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules (e.g., as in a substrate, bound to a first antibody, bound to an analyte, bound to a second antibody), thereby forming a complex. As used herein, the term "attached" refers to the state of two things being joined, fastened, adhered, connected or bound to each other. For example, a sample such as a cell or tissue, can be attached to a material, such as a hydrogel, polymer, or solid support, by a covalent or non-covalent bond. In embodiments, attachment is a covalent attachment.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed by such disclosure herein. The upper and lower limits of any such smaller range (within a more broadly recited range) may independently be included in the smaller ranges, or as particular values themselves, and are also encompassed by such disclosure herein, subject to any specifically excluded limit in the stated range. Where the stated range includes one or both of the limits, ranges excluding either or both of those included limits are also included by such disclosure herein.

Provided herein are methods, systems, and compositions for analyzing a sample (e.g., sequencing nucleic acids within a sample) in situ. The term "in situ" is used in accordance with its ordinary meaning in the art and refers to a sample surrounded by at least a portion of its native environment, such as may preserve the relative position of two or more elements. For example, an extracted human cell obtained is considered in situ when the cell is retained in its local microenvironment so as to avoid extracting the target (e.g., nucleic acid molecules or proteins) away from their native environment. An in situ sample (e.g., a cell) can be obtained from a suitable subject. An in situ cell sample may refer to a cell and its surrounding milieu, or a tissue. A sample can be isolated or obtained directly from a subject or part thereof. In embodiments, the methods described herein (e.g., sequencing a plurality of target nucleic acids of a cell in situ) are applied to an isolated cell (i.e., a cell not surrounded by least a portion of its native environment). For the avoidance of any doubt, when the method is performed within a cell (e.g., an isolated cell) the method may be considered in situ. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may include cells or tissues that are normal, healthy, diseased (e.g., infected), and/or cancerous (e.g., cancer cells). A sample obtained from a subject may include cells or cellular material (e.g., nucleic acids) of multiple organisms (e.g., virus nucleic acid, fetal nucleic acid, bacterial nucleic acid, parasite nucleic acid). A sample may include a cell and RNA transcripts. A sample can include nucleic acids obtained from one or more subjects. In some embodiments a sample includes nucleic acid obtained from a single subject. A subject can be any living or non-living organism, including but not limited to a human, non-human animal, plant, bacterium, fungus, virus, or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a plant. In some embodiments, a subject is a human subject. A subject can be a patient (e.g., a human patient). In some embodiments a subject is suspected of having a genetic variation or a disease or condition associated with a genetic variation. A "tissue section" as used herein refers to a portion of a biological tissue derived from a biological sample, typically from an organism (e.g., a human or animal subject or patient).

As used herein, the term "fresh," generally in the context of a fresh tissue means that the tissue has recently been obtained from an organism, generally before any subsequent fixation steps, for example, flash freezing or chemical fixation. In embodiments, a fresh tissue is obtained from an organism about 1 second up to about 20 minutes before any fixation steps are performed. In embodiments, a fresh tissue is obtained from an organism about 1 second up to about 60 seconds before any fixation steps are performed. In embodiments, a fresh tissue is obtained from an organism about 30 seconds up to about 60 seconds before any fixation steps are performed. In embodiments, a fresh tissue is obtained from an organism about 1 minutes up to about 20 minutes before any fixation steps are performed. In embodiments, a fresh tissue is obtained from an organism about 1 minutes up to about 10 minutes before any fixation steps are performed. In embodiments, a fresh tissue is obtained from an organism about 1 minutes up to about 5 minutes before any fixation steps are performed. In embodiments, a fresh tissue is obtained from an organism about 30 seconds, about 1 minute, about 2 minutes, about 3 minutes, about 4 minutes, about 5 minutes, about 10 minutes, about 15 minutes, or about 20 minutes before any fixation steps are performed.

As used herein, the term "fix," refers to formation of covalent bonds, such as crosslinks, between biomolecules or within molecules. The process of fixing tissue samples or biological samples (e.g., cells and nuclei) for example, is called "fixation." The agent that causes fixation is generally referred to as a "fixative" or "fixing agent." "Fixed biological samples" (e.g., fixed cells or nuclei) or "fixed tissues" refers to biological samples (e.g., cells or nuclei) or tissues that have been in contact with a fixative under conditions sufficient to allow or result in formation of intra- and inter-molecular crosslinks between biomolecules in the biological sample. Fixation may be reversed and the process of reversing fixation may be referred to as "un-fixing" or "decrosslinking." Unfixing or decrosslinking refers to breaking or reversing the formation of covalent bonds in biomolecules formed by fixatives. In some examples, the tissue fixed is fresh tissue. In some examples, the tissue fixed may be frozen tissue. In some examples, the tissue fixed may not be dissociated. In some examples, the tissue fixed may be dissociated or partially dissociated (e.g., chopped, cut). In some examples, tissue that has been rapidly frozen and, perhaps, cut or chopped into pieces (e.g., small enough to fit into a tube or container used for fixation) may be used. In some examples, tissue may be dissociated or partially dissociated (e.g., cut, chopped) before or during fixation. In some examples, tissue that is fixed may not be dissociated. The frozen biological tissue can be fixed using a fixing agent, which is suitably an organic fixing agent. Suitable organic fixing agents include without limitation alcohols, ketones, aldehydes (e.g., glutaraldehyde), cross-linking agents, disuccinimidyl suberate (DSS), dimethylsuberimidate (DMS), formalin, dimethyladipimidate (DMA), dithiobis(-succinimidyl propionate) (DSP), disuccinimidyl tartrate (DST), ethylene glycol bis (succinimidyl succinate) (EGS), bis(sulfosuccinimidyl)suberate (BS3) and combinations thereof. A particularly suitable fixing agent is a formaldehyde-based fixing agent such as formalin, which is a mixture of formaldehyde and water. The formalin may include about 1% to about 15% by weight formaldehyde and about 85% to about 99% by weight water, suitable about 2% to about 8% by weight formaldehyde and about 92% to about 98% by weight water, or about 4% by weight formaldehyde and about 96% by weight water. In some examples, tissues may be fixed in 4% paraformaldehyde. Other suitable fixing agents will be appreciated by those of ordinary skill in the art (e.g., International PCT App. No. PCT/US2020/066705, which is incorporated herein by reference in its entirety).

As used herein, the term "permeable" refers to a property of a substance that allows certain materials to pass through the substance. "Permeable" may be used to describe a biological sample, such as a cell or nucleus, in which analytes in the biological sample can leave the biological sample. "Permeabilize" is an action taken to cause, for example, a biological sample (e.g., a cell) to release its analytes. In some examples, permeabilization of a biological sample is accomplished by affecting the integrity (e.g., compromising) of a biological sample membrane (e.g., a cellular or nuclear membrane) such as by application of a protease or other enzyme capable of disturbing a membrane allowing analytes to diffuse out of the biological sample. In some embodiments, permeabilizing a biological sample does not release the biomolecules (e.g., proteins and/or nucleic acids) contained within the sample.

As used herein, the term "single biological sample", such as a single cell or a single nucleus generally refers to a biological sample that is not present in an aggregated form or clump. Single biological samples, such as cells and/or nuclei may be the result of dissociating a tissue sample.

As used herein, the term "tissue freezing" is used in accordance with its plain and ordinary meaning and refers to different methods for freezing tissues. In some examples, the methods used may be rapid methods (e.g., "flash freezing" or "snap freezing"). In some examples, tissues may be lowered to temperatures below about −70° C. using these methods. In some examples, rapid freezing may use ultracold media. In some examples, an ultracold medium may be liquid nitrogen. In some examples, this type of freezing may preserve tissue integrity, in part by preventing the formation of ice crystals that would affect the tissue morphology. In some examples, an ultracold medium may be dry ice.

As used herein, a "single cell" refers to one cell. Single cells useful in the methods described herein can be obtained from a tissue of interest, or from a biopsy, blood sample, or cell culture. Additionally, cells from specific organs, tissues, tumors, neoplasms, or the like can be obtained and used in the methods described herein. In general, cells from any population can be used in the methods, such as a population of prokaryotic or eukaryotic organisms, including bacteria or yeast.

As used herein, the term "tissue" is used in accordance with its plain and ordinary meaning and refers to an organization of cells in a structure, where the structure generally functions as a unit in an organism (e.g., mammals) and may carry out specific functions. In some examples, cells in a tissue are configured in a mass and may not be free from one another. This disclosure describes methods of obtaining single biological samples (e.g., cells or nuclei) from tissues that can be used in various single biological samples (e.g., single-cell/nucleus) workflows. In some examples, blood cells (e.g., lymphocytes) can be considered a tissue. However, blood cells, like lymphocytes, generally are free from one another in the blood. The methods disclosed herein can be used to process those cells to obtain cells and/or nuclei, although dissociation steps may not be necessary when using those types of tissues. Generally, any type of tissue can be used in the methods described herein. Examples of tissues that may be used in the disclosed methods include, but are not limited to connective, epithelial, muscle and nervous tissue. In some examples, the tissues are from mammals. Tissues that contain any type of cells may be used. For example, tissues from abdomen, bladder, brain, esophagus, heart, intestine, kidney, liver, lung, lymph node, olfactory bulb, ovary, pancreas, skin, spleen, stomach, testicle, and the like. The tissue may be normal or tumor tissue (e.g., malignant). This example is not meant to be limiting. Although the conditions used in the disclosed may not be identical for different types of tissue, the methods may be applied to any tissue. The tissues used in the disclosed methods may be in various states. In some examples, the tissues used in the disclosed methods may be fresh, frozen, or fixed.

The term "cellular component" is used in accordance with its ordinary meaning in the art and refers to any organelle, nucleic acid, protein, or analyte that is found in a prokaryotic, eukaryotic, archaeal, or other organismic cell type. Examples of cellular components (e.g., a component of a cell) include RNA transcripts, proteins, membranes, lipids, and other analytes. In embodiments, a cellular component is a biomolecule.

A "gene" refers to a polynucleotide that is capable of conferring biological function after being transcribed and/or translated.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system including two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

As used herein the term "determine" can be used to refer to the act of ascertaining, establishing or estimating. A determination can be probabilistic. For example, a determination can have an apparent likelihood of at least 50%, 75%, 90%, 95%, 98%, 99%, 99.9% or higher. In some cases, a determination can have an apparent likelihood of 100%. An exemplary determination is a maximum likelihood analysis or report. As used herein, the term "identify," when used in reference to a thing, can be used to refer to recognition of the thing, distinction of the thing from at least one other thing or categorization of the thing with at least one other thing. The recognition, distinction or categorization can be probabilistic. For example, a thing can be identified with an apparent likelihood of at least 50%, 75%, 90%, 95%, 98%, 99%, 99.9% or higher. A thing can be identified based on a result of a maximum likelihood analysis. In some cases, a thing can be identified with an apparent likelihood of 100%.

The terms "bioconjugate group," "bioconjugate reactive moiety," and "bioconjugate reactive group" refer to a chemical moiety which participates in a reaction to form a bioconjugate linker (e.g., covalent linker).

As used herein, the term "bioconjugate reactive moiety" and "bioconjugate reactive group" refers to a moiety or group capable of forming a bioconjugate (e.g., covalent linker) as a result of the association between atoms or molecules of bioconjugate reactive groups. The association can be direct or indirect. For example, a conjugate between a first bioconjugate reactive group (e.g., —NH2, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds.; (n) azides coupled to alkynes using copper catalyzed cycloaddition click chemistry; (o) biotin conjugate can react with avidin or streptavidin to form a avidin-biotin complex or streptavidin-biotin complex.

The term "covalent linker" is used in accordance with its ordinary meaning and refers to a divalent moiety which connects at least two moieties to form a molecule.

The term "non-covalent linker" is used in accordance with its ordinary meaning and refers to a divalent moiety which includes at least two molecules that are not covalently linked to each other but are capable of interacting with each other via a non-covalent bond (e.g., electrostatic interactions (e.g., ionic bond, hydrogen bond, halogen bond) or van der Waals interactions (e.g., dipole-dipole, dipole-induced dipole, London dispersion). In embodiments, the non-covalent linker is the result of two molecules that are not covalently linked to each other that interact with each other via a non-covalent bond.

An "antibody" (Ab) is a protein that binds specifically to a particular substance, known as an "antigen" (Ag). An "antibody" or "antigen-binding fragment" is an immunoglobulin that binds a specific "epitope." The term encompasses polyclonal, monoclonal, and chimeric antibodies. In nature, antibodies are generally produced by lymphocytes in response to immune challenge, such as by infection or immunization. An "antigen" (Ag) is any substance that reacts specifically with antibodies or T lymphocytes (T cells). An antibody may include the entire antibody as well as any antibody fragments capable of binding the antigen or antigenic fragment of interest. Examples include complete antibody molecules, antibody fragments, such as Fab, F(ab') 2, CDRs, VL, VH, and any other portion of an antibody which is capable of specifically binding to an antigen. Antibodies used herein are immunospecific for, and therefore specifically and selectively bind to, for example, proteins either detected (e.g., biological targets of interest) or used for detection (e.g., probes containing oligonucleotide barcodes) in the methods and devices as described herein.

As used herein, the term "control" or "control experiment" is used in accordance with its plain and ordinary meaning and refers to an experiment in which the subjects, cells, tissues, or reagents of the experiment are treated as in a parallel experiment except for omission of a procedure, reagent, or variable of the experiment. In some instances, the control is used as a standard of comparison in evaluating experimental effects. In embodiments, a control cell is the same cell type as the cell being examined, wherein the control cell does not include the variable or is subjected to conditions being examined.

Typically, the concentration and molecular weight of the hydrogel subunit(s) will depend on the selected polymer and the desired characteristics, e.g., pore size, swelling properties, conductivity, elasticity/stiffness (Young's modulus), biodegradability index, etc., of the hydrogel network into which they will be polymerized. For example, it may be desirable for the hydrogel to include pores of sufficient size to allow the passage of macromolecules, e.g., proteins, nucleic acids, or small molecules as described in greater detail below, into the specimen. The ordinarily skilled artisan will be aware that pore size generally decreases with increasing concentration of hydrogel subunits and generally increases with an increasing ratio of hydrogel subunits to crosslinker, and will prepare a hydrogel composition that includes a concentration of hydrogel subunits that allows the passage of such macromolecules. As another example, it may be desirable for the hydrogel to have a particular stiffness, e.g., to provide stability in handling the embedded specimen, e.g., a Young's Modulus (also referred to herein as a compression modulus) of about 2-70 kN/m$^2$, for example, about 2 kN/m$^2$, about 4 kN/m$^2$, about 7 kN/m$^2$, about 10 kN/m$^2$, about 15 kN/m$^2$, about 20 kN/m$^2$, about 40 kN/m$^2$, but typically not more than about 70 kN/m$^2$. The ordinarily skilled artisan will be aware that the elasticity of a hydrogel network may be influenced by a variety of factors, including the branching of the polymer, the concentration of hydrogel subunits, and the degree of cross-linking, and will prepare a hydrogel composition that includes a concentration of hydrogel subunits to provide such desired elasticity. Thus, for example, the hydrogel composition may include an acrylamide monomer at a concentration of from about 1% w/v to about 20% w/v, e.g., about 2% to about 15%, about 3% to about 10%, about 4% to about 8%, and a concentration of bis-acrylamide crosslinker in the range of about 0.01% to about 0.075%, e.g., 0.01%, 0.02%, 0.025%, 0.03%, 0.04%, 0.05%, 0.06%, or 0.075%; or, for example, the hydrogel composition may include PEG prepolymers having a molecular weight ranging from at least about 2.5K to about 50K, e.g., 2.5K or more, 3.5K or more, 5K or more, 7.5K or more, 10K or more, 15K or more, 20K or more, but typically not more than about 50K, at a concentration in a range from about 1% w/w to about 50% w/w, e.g., 1% or more, 5% or more, 7.5% or more, 10% or more, 15% or more, 20% or more, 30% or more, 40% or more, and usually not more than about 50%. Concentrations of hydrogel subunits that provide desired hydrogel characteristics may be readily determined by methods in the art or as described in the working examples below.

The term "image" is used according to its ordinary meaning and refers to a representation of all or part of an object. The representation may be an optically detected reproduction. For example, an image can be obtained from fluorescent, luminescent, scatter, or absorption signals. The part of the object that is present in an image can be the surface or other xy plane of the object. Typically, an image is a 2 dimensional representation of a 3 dimensional object. An image may include signals at differing intensities (i.e., signal levels). An image can be provided in a computer readable format or medium. An image is derived from the collection of focus points of light rays coming from an object (e.g., the sample), which may be detected by any image sensor.

As used herein, the term "signal" is intended to include, for example, fluorescent, luminescent, scatter, or absorption impulse or electromagnetic wave transmitted or received. Signals can be detected in the ultraviolet (UV) range (about 200 to 390 nm), visible (VIS) range (about 391 to 770 nm), infrared (IR) range (about 0.771 to 25 microns), or other range of the electromagnetic spectrum. The term "signal level" refers to an amount or quantity of detected energy or coded information. For example, a signal may be quantified by its intensity, wavelength, energy, frequency, power, luminance, or a combination thereof. Other signals can be quantified according to characteristics such as voltage, current, electric field strength, magnetic field strength, frequency, power, temperature, etc. Absence of signal is understood to be a signal level of zero or a signal level that is not meaningfully distinguished from noise.

The term "xy coordinates" refers to information that specifies location, size, shape, and/or orientation in an xy plane. The information can be, for example, numerical coordinates in a Cartesian system. The coordinates can be provided relative to one or both of the x and y axes or can be provided relative to another location in the xy plane (e.g., a fiducial). The term "xy plane" refers to a 2 dimensional area defined by straight line axes x and y. When used in reference to a detecting apparatus and an object observed by the detector, the xy plane may be specified as being orthogonal to the direction of observation between the detector and object being detected.

The term "adhesion strength" or "attachment strength" as used herein refers to the interfacial force bonding two materials together. The adhesion strength may refer to the minimal amount of force necessary to detach and/or remove the two materials. Means for quantifying adhesion strength are known in the art, for example with a pull-off adhesion test. A pull-off adhesion test measures the resistance of a substance (e.g., a tissue sample) from a substrate (e.g., a carrier substrate) when a perpendicular tensile force is applied to the substance. As outlined in the American Society for Testing and Materials (ASTM) D4541 (and similarly in BS EN ISO 4624), the test may include attaching a test dolly to the substance (e.g., the tissue sample) and then pulling the dolly by exerting a force perpendicular to the surface in an effort to remove the dolly with the substance from the substrate. An alternative testing approach is outlined in ASTM D6677 which utilizes a utility knife to peel the substance away from the substrate and ASTM D3359 which uses a pressure sensitive tape. The peel strength tests employed for examining the strength of Band-Aid® bonds is provided in ASTM D903, ASTM D1876, and ASTM F2258, each of which are incorporated herein by reference and may be used for measuring the adhesion strength as described herein. Instruments for performing such measurements include the monotonic uniaxial tensile testing device provided by Bose® Biodynamic Test Instrument, Minnetonka, MN, for example by employing at a constant rate (e.g., 0.05 mm/sec) and continuously recording the load response (e.g., 200 measurements/sec) to the point of macroscopic failure, or the Avery Adhesive Test (AAT).

As used herein, the term "resected" or "resection" is used in accordance with its plain and ordinary meaning and refers to removal of part or all of a tissue or an organ from a subject, typically through surgical removal.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

II. Systems, Devices, & Kits

Figure 2A:
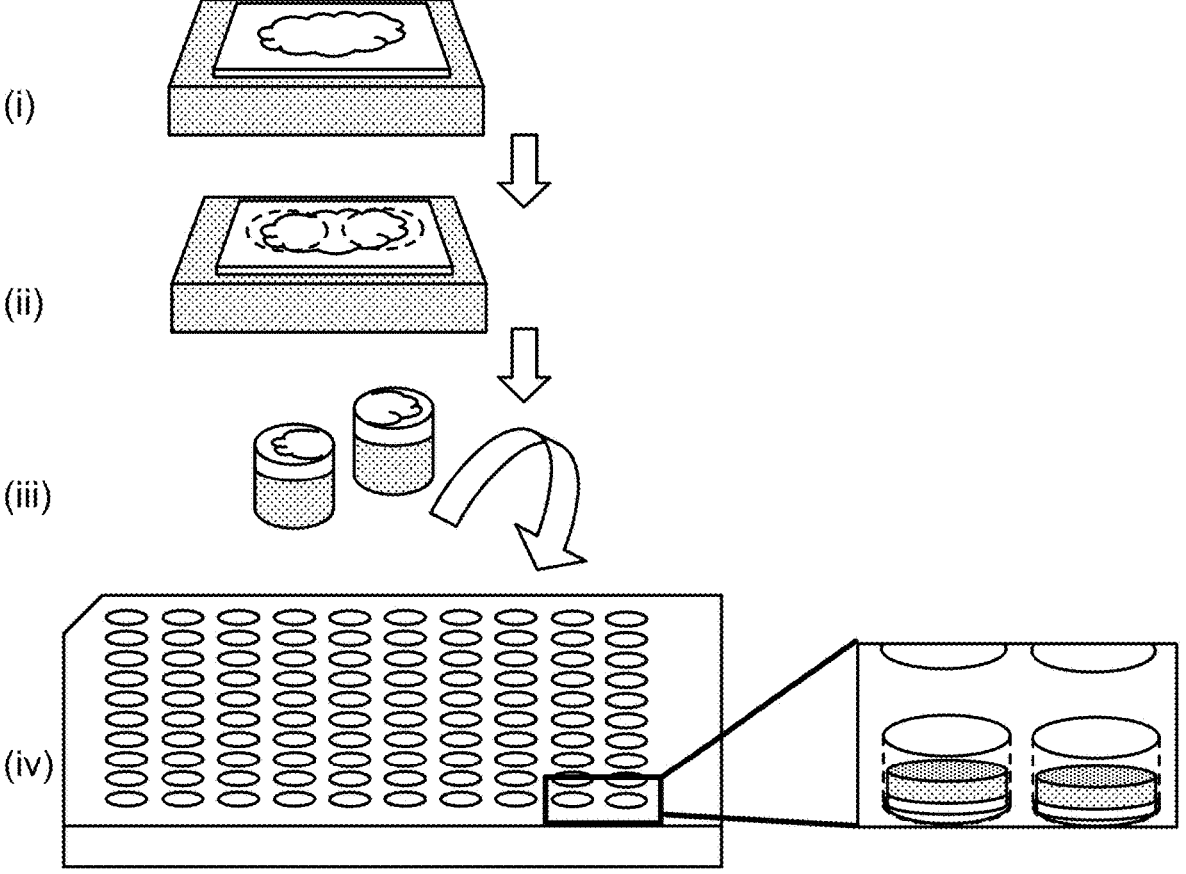
FIGS. 2A-2B schematically illustrates a potential workflow for the sample-carrier constructs. For example.
Figure 2B:
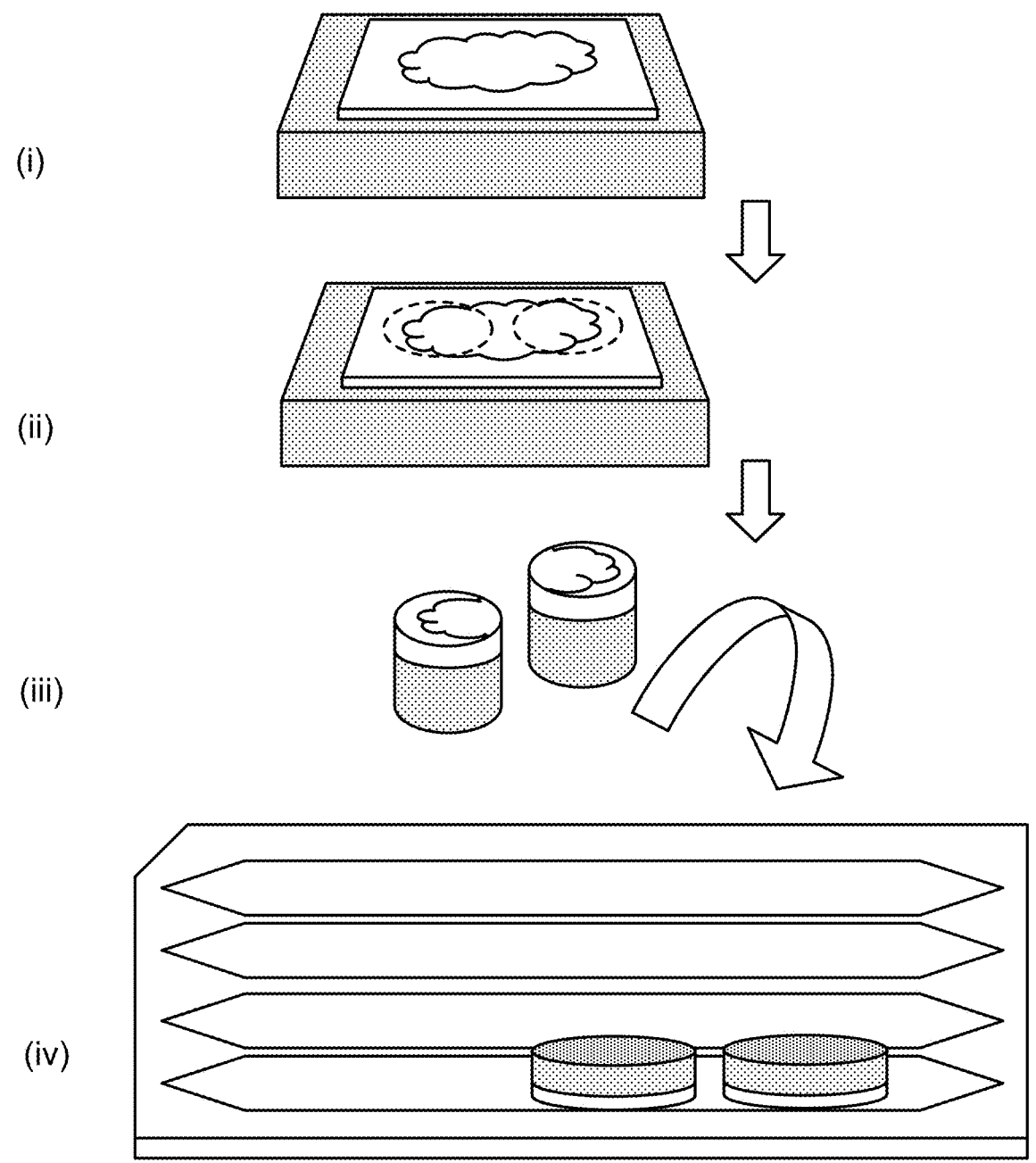

In an aspect, there is disclosed devices for manipulating one or more biological samples that can be obtained from a sample block (e.g., frozen tissue block or a paraffin embedded biological sample). FIG. 1 schematically shows a biological sample block 10, which can be for example either an FFPE block (i.e., a paraffin embedded biological sample) or fresh frozen tissue block containing a biological sample. The sample block 10 can be sliced into very thin sections 10a, 10b, and 10c pursuant to a sectioning process. The sections 10a-10c are captured or otherwise coupled to a carrier substrate 15 to generate a sample-carrier construct 105. FIGS. 2A-2B schematically illustrates a potential workflow for obtaining the sample-carrier constructs.

Figure 4A:
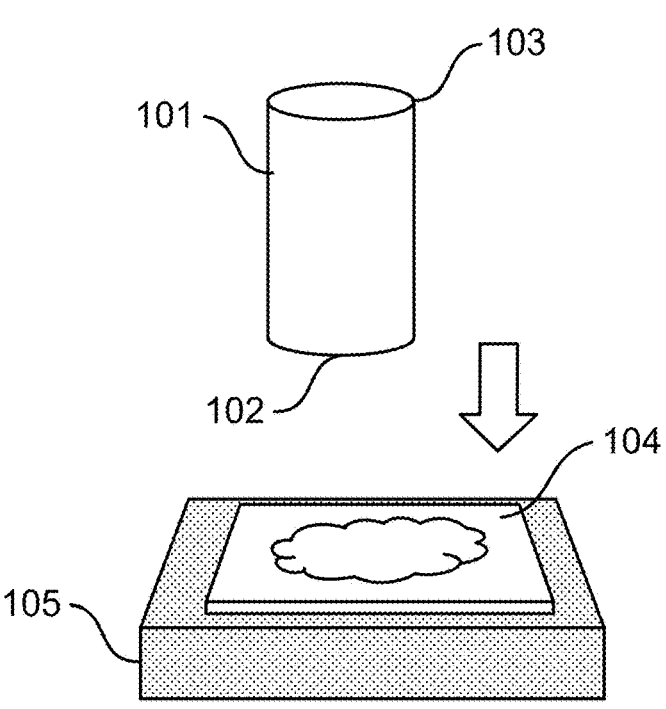
FIGS. 4A-4B illustrate elements of the punch device (101) and the method of use. The bottom edge (102) of the punch device is brought into contact with a sample (e.g., a sample as described herein, such as tissue section (104) attached to a carrier substrate (105)). In embodiments, the bottom edge (102) of the punch device is sharp to permit cutting through the sample and/or the carrier substrate. A downward pressure is applied to the punch device (such as to the top (103) of the punch device) to cut through the tissue section and the carrier substrate, as illustrated in FIG. 4B. A cross section is illustrated in FIG. 4B to show the resulting sample is cut to provide a portion of the sample (106), retaining a shape similar to the punch device. The portion of the sample (106) is thus loaded in the punch device.
Figure 4B:
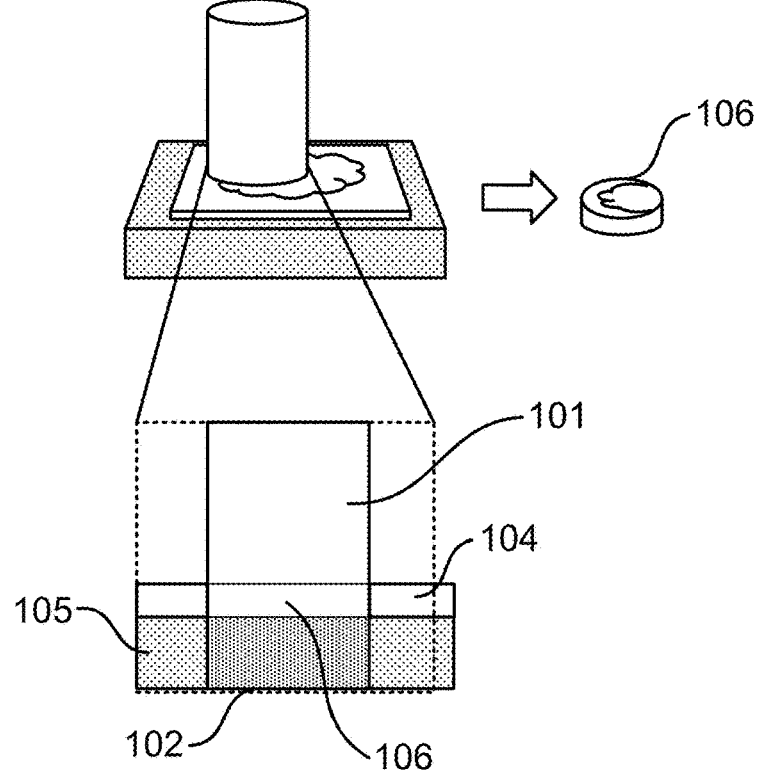

After the sample-carrier construct 105 is obtained or otherwise provided, one or more portions of the sample carrier construct are obtained using a sampling system as described further below. With reference to FIGS. 4A-4B, the sample cutting system includes at least one punch device 101. As shown in FIG. 4A, the punch device 101 is formed of hollow structure that forms an internal cavity (i.e., a shaft). The punch device 101 has a bottom edge 102 that is sufficiently sharp to cut through the sample carrier construct 105 when pressed against the sample carrier construct 105. In an embodiment, the bottom edge 102 has a tapered edge and/or a stainless steel blade attached at the bottom to facilitate cutting. In embodiments, the bottom edge 102 is substantially flat. The punch device 101 is shown having a cylindrical shape although the shape can vary (e.g., as described herein). The punch device 101 is hollow such the punch device 101 cuts or punches through the sample carrier construct 105 and forms a correspondingly shaped sample portion 106 inside the cavity of the punch device 101 when pressed thereto, such as in a cookie cutter manner. The punch device 101 with the sample portion 106 positioned therein can be referred to as a loaded punch device 101. The bottom edge 102 of the punch device 101 can be sufficiently sharp to cut through both the tissue section 104 and the carrier substrate 105, as shown in FIG. 4B, which shows the punch device 101 in a loaded state.

Figures 11, 12:
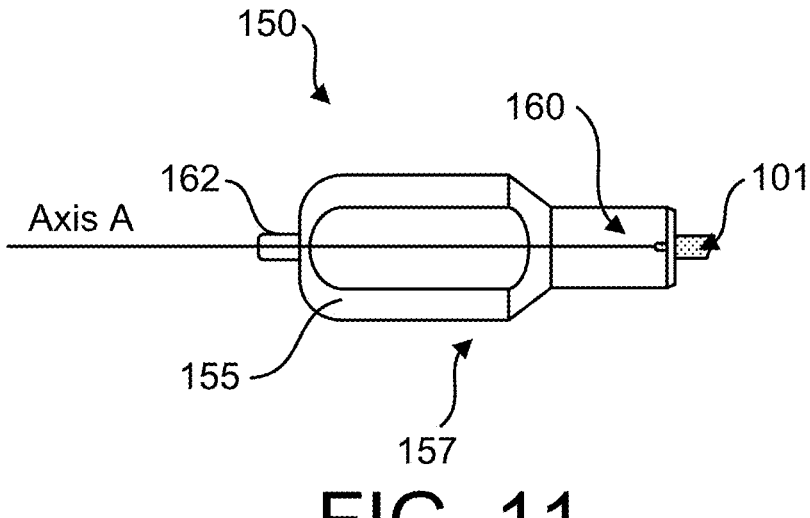
FIG. 11 shows another embodiment wherein a punch tool 150 is configured to be coupled to the punch device 101. The punch tool 150 is a tool that receives the punch device 101. In embodiments, a user actuates the spring-loaded punch tool 150 to expel, eject, or otherwise transition the punch device 101 toward the sample carrier construct 105 (FIG. 4A) to cut through the sample carrier construct 105 and obtain a sample portion 106. The punch tool 150 has an outer housing 155 that extends along a long axis A. The punch tool 150 has a docking region 160 that removably receives the punch device 101. In an embodiment, the punch device 101 is aligned with the long axis A when docked in the punch tool 150 to permit a user to grasp the punch tool 150 and ergonomically manipulate the position and orientation of the punch device 101 such as in the manner of grasping a pen. However, it should be appreciated that the size and shape of the punch tool 150 can vary and that the embodiment shown in FIG. 11 is a non-limiting example.
FIG. 12 shows the outer housing 155 of the punch tool 150 which includes an enlarged portion 157 that can be grasped with a hand of a user.
Figure 18:
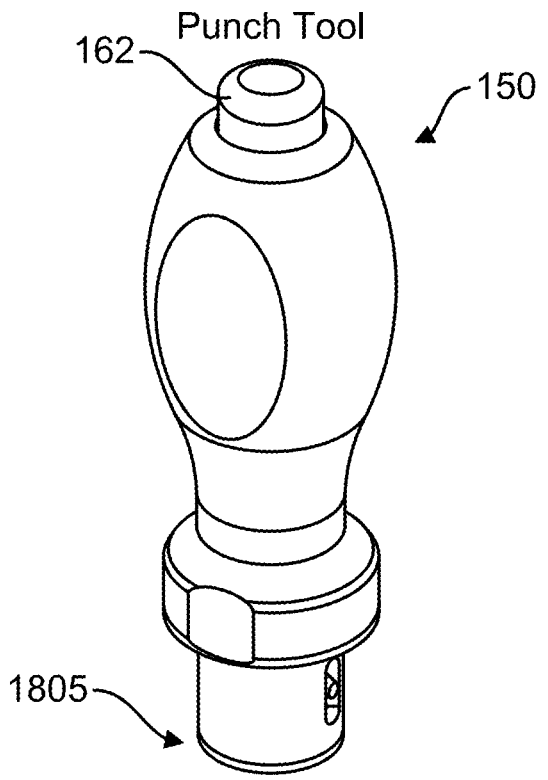
FIG. 18 shows another embodiment wherein a punch tool 150 is configured to be coupled to the punch device 101. In embodiments, the punch tool 150 is a spring-loaded tool that receives the punch device 101 and includes an actuator such as button to engage and release the punch device. The punch tool may also include a toroidal seal 1805, alternatively referred to as an O-ring, to facilitate retention of the cutting device when engaged in the punch tool.
Figure 19:
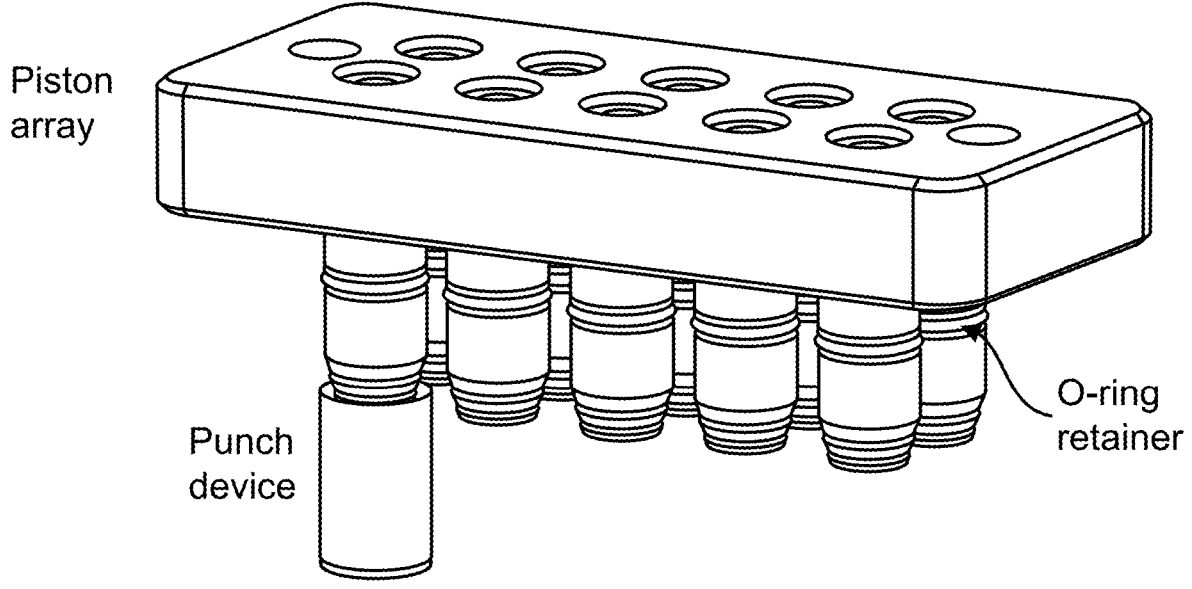
FIG. 19 illustrates an embodiment of the piston array. The piston array may further include a toroidal seal (i.e., an O-ring) to facilitate retention of the punch device when engaged on a piston of the piston array.

FIG. 11 shows another embodiment wherein a punch tool 150 is configured to be coupled to the punch device 101. The punch tool 150 is a spring-loaded tool that receives the punch device 101 and that can be actuated to eject the punch device 101 via a spring-loaded mechanism. A user actuates the punch tool 150 to expel, eject, or otherwise transition the punch device 101 toward the sample carrier construct 105 (FIG. 4A) to cut through the sample carrier construct 105 and obtain a sample portion 106. The punch tool 150 has an outer housing 155 that extends along a long axis A. The outer housing 155 has an enlarged portion 157 that can be grasped with a hand of a user, as shown in FIG. 12. The punch tool 150 has a docking region 160 that removably receives the punch device 101. In an embodiment, the punch device 101 is aligned with the long axis A when docked in the punch tool 150 to permit a user to grasp the punch tool 150 and ergonomically manipulate the position and orientation of the punch device 101 such as in the manner of grasping a pen. However, it should be appreciated that the size and shape of the punch tool 150 can vary and that the embodiment shown in FIG. 11 is a non-limiting example. For example, an alternative embodiment is illustrated in FIG. 18. In the embodiment of FIG. 18, the punch tool 150 has an ergonomically shaped housing and an O-ring 1805 on a bottom portion. The O-ring 1805 is configured to facilitate retention of the punch device when engaged in the punch tool 150. FIG. 19 shows the piston array with punch devices loaded thereon.

In the embodiments of FIGS. 11 and 18, the punch tool 150 has an actuator 162, such as a button, that can be actuated by a user to cause the spring-loaded punch tool 150 to exert a force onto the punch device 101 and move the punch device in an outward direction D. This can be used to cut a sample carrier construct 105, as described further below.

Figure 13:
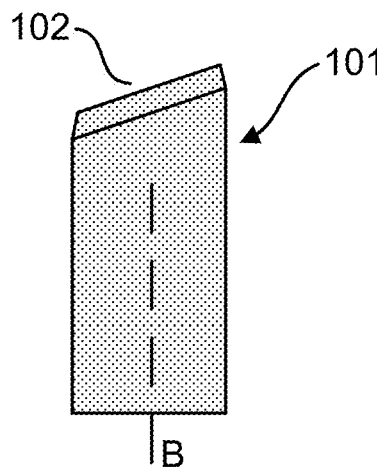
FIG. 13 shows an embodiment of the punch device 101. As mentioned, the punch device is body such as a tubular body having an internal lumen and a cutting edge 102 configured to cut through a biological sample, such as a tissue. The cutting edge 102 can be oriented at any of a variety of angles relative to a long axis B of the punch device 101. For example, the cutting edge may be substantially flat. In embodiments, the cutting edge is angled (e.g., a 10°, 150 or 20° angle).

FIG. 13 shows an embodiment of the punch device 101. As mentioned, the punch device is body having an internal lumen and a cutting edge 102 configured to cut through tissue. The cutting edge 102 can be oriented at any of a variety of angles relative to a long axis B of the punch device 101. In the embodiment of FIG. 13, the cutting edge 102 is angled at a non-normal angle relative to the axis B. The angle can vary.

Figure 14:
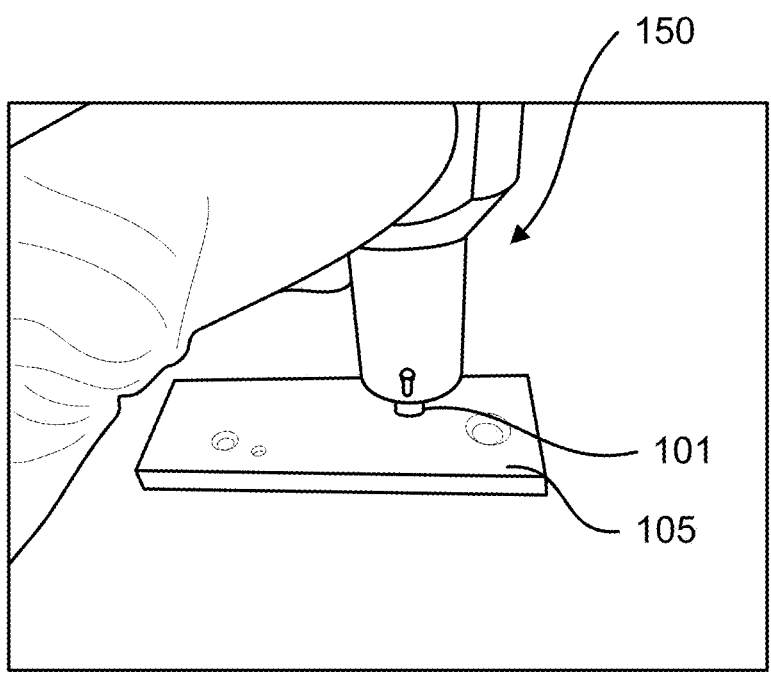
FIG. 14 demonstrates the punch tool 150 with a punch device 101 loaded thereon. The user grasps the punch tool 150 and then orients the punch tool 150 so that the cutting edge of the attached punch device 101 is facing or adjacent the sample carrier construct 105.
Figure 15:
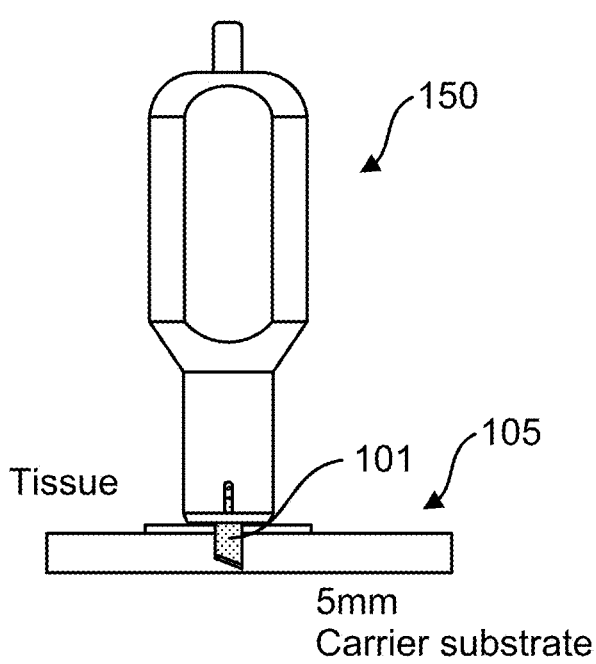
FIG. 15 provides an illustration of the punch tool 150 with a punch device 101 loaded thereon. The user grasps the punch tool 150 and then orients the punch tool 150 so that the cutting edge of the attached punch device 101 is facing or adjacent the sample carrier construct 105. The cutting device is then pushed down to cut through the tissue and the carrier substrate.
Figure 16:
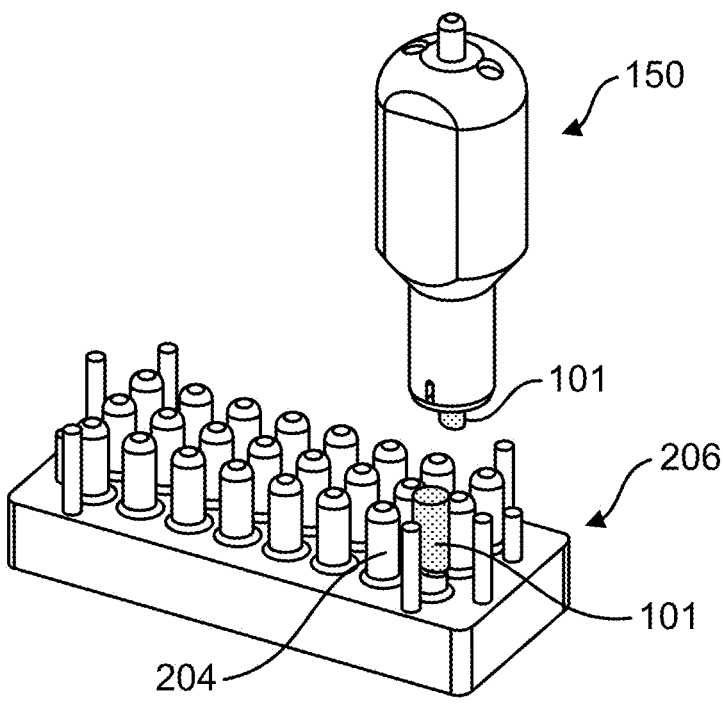
FIG. 16 shows that a user can then orient the punch tool 150 relative to a piston array 206 (described with reference to FIG. 5B) and eject the punch device 101 onto the piston array by inserting the punch device onto a piston that extends from the piston array.

In use, a user obtains a punch tool 150 with a punch device 101 loaded thereon (as shown in FIG. 11 or FIG. 18) The user can manually load the punch device 101 onto the punch tool 150 or the punch tool 150 can be pre-loaded with a punch device 101. The user grasps the punch tool 150 (as shown in FIG. 12) and then orients the punch tool 150 so that the cutting edge of the attached punch device 101 is facing or adjacent the sample carrier construct 105, as shown in FIG. 14 and FIG. 15. The user then actuates the actuator 162 so that the punch tool 150 pushes the punch device 101 toward and cuts into the sample carrier construct 105 to obtain a sample portion which is then retained inside a now loaded punch device 101. As shown in FIG. 16, the user can then orient the punch tool 150 relative to a piston array 206 (described below with reference to FIG. 5B) and eject the punch device 101 onto the piston array. That is, the punch device 101 inserts over a respective rod or piston 204 of the piston array such that at least a portion of the piston 204 is slidingly positioned inside the punch device 101.

The use of the punch tool 150 can provide greater consistency when obtaining multiple sample portions and minimize/reduce sample loss. The use of a punch tool 150 can also reduce the time spent manipulating samples. The punch tool 150 can include various mechanisms to facilitate cutting, such as a piezoelectric motor within the punch tool to improve cutting through various biological samples (e.g., bone) by introducing ultrasonic vibrations in the cutting blade or cutting edge of the punch device 101.

Figure 5A:
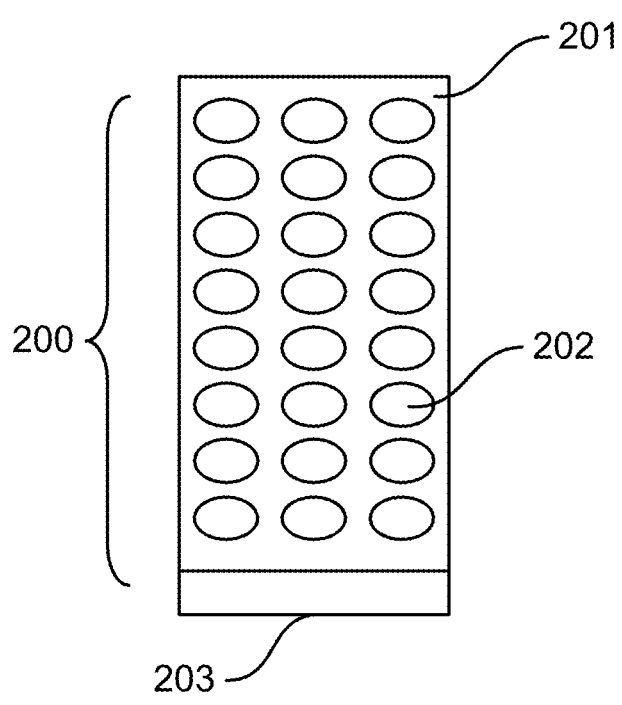
FIGS. 5A-5C provide illustrations of the receiving array (FIG. 5A) and the piston array (FIG. 5B), and the combined assembly. The receiving array (200) provides a series of wells or receptacles (202) for retaining the punch devices. In embodiments, the receptacles of the receiving array includes one or more bores, slots, seats, retention mechanisms, or other structures sized and shaped to receive, align, and secure a respective punch device within the receptacle (e.g., wherein the punch device includes a complementary-shaped structure to the bores, slots, seats, retention mechanisms, or other structures of the receiving array receptacle). The top (201) or the bottom (203) of the receiving array may contact the microplate depending on the user preference.
Figure 5B:
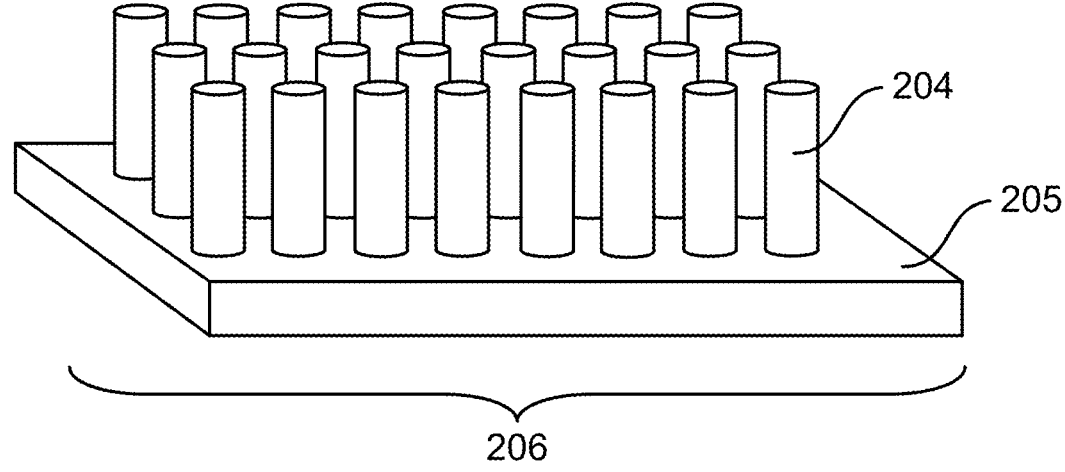
Figure 5C:
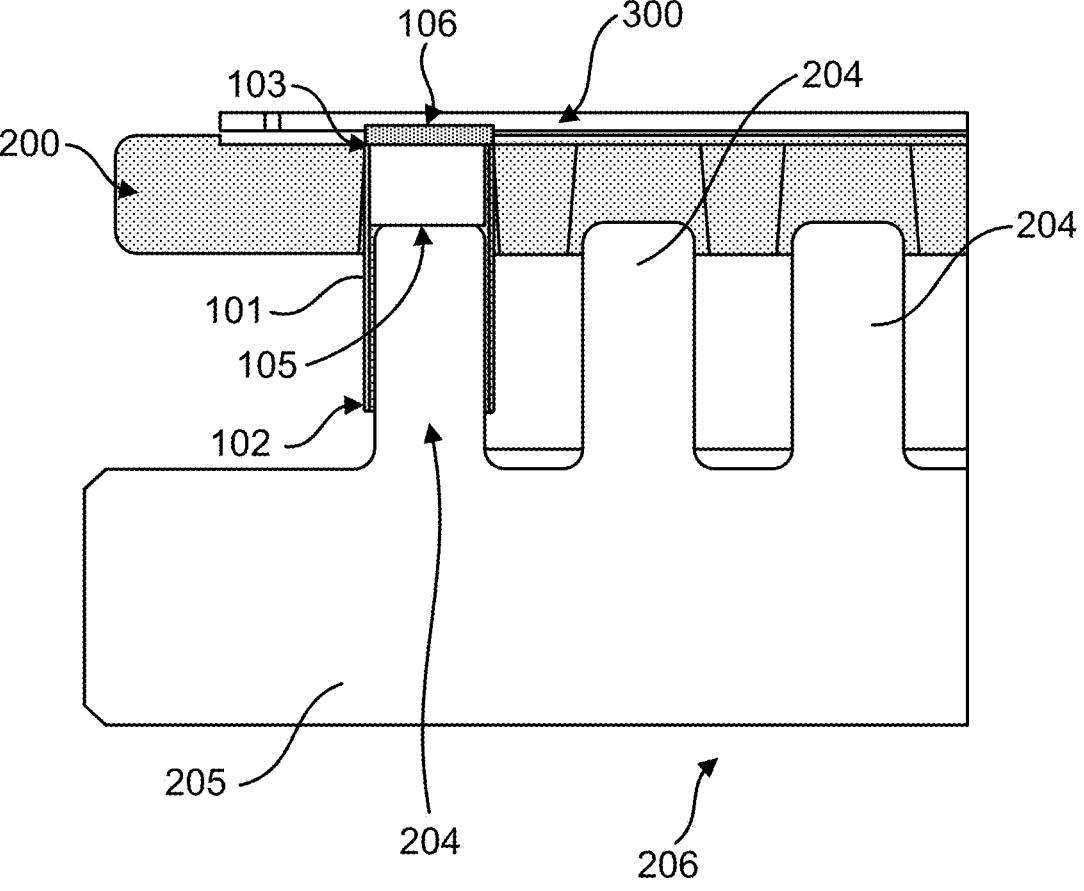

With reference to FIGS. 5A-5B, the sampling system further includes a receiving array 200 having one or more receptacles 202 each configured to receive at least one sample portion 106 obtained using the punch device 101. The receptacles 202 are also each configured to receive a punch device 101 containing sample portion 106 for depositing the sample portion 106 into a respective receptacle 202. The receptacles 202 may be arranged in a rectangular array pattern as shown in FIG. 5A or in any other pattern. The receiving array 200 is configured to mechanically interact with a piston array 206 (FIG. 5B). The receiving array may be a microplate. The receiving array may be a coupled to a glass slide (e.g., a receiving array may aid in alignment for placement of the samples in suitable locations, for example within predetermined channels of a flow cell). The piston array 206 is formed of a base 205 and one or more plungers, pistons or rods 204 extending upwardly from the base 205. Each rod 204 is sized and shaped to fit within a respective receptacle 202 of the receiving array 200. In an embodiment, the quantity of receptacles corresponds to the quantity of the rods 204. In addition, the size, shape and spatial arrangement of the rods correspond to and complements the size, shape and spatial arrangement of the receptacles 202 such that the piston array 200 can be mechanically coupled to the receiving array 200 with each rod 204 aligning with and inserting into a respective receptacle 202.

Figure 17A:
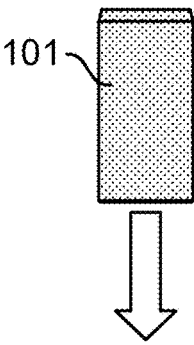
FIGS. 17A-17C provides a workflow describing an embodiment of sample manipulation. First a punch device 101 is collected and placed on a punch tool (e.g., the punch tool 150 described in FIG. 11). A user may then orient the punch tool 150 (with attached punch device 101) to cut through a biological sample, such as a tissue and the carrier substrate (e.g., as illustrated in FIG. 4B) such that the punch device 101 is loaded with a biological sample. The loaded punch device 101 may then be loaded onto the piston array 206 (see step 4 of FIG. 17B) by inserting the punch device 101 onto a corresponding piston. The process outlined in FIG. 17A may then be repeated with a new punch device to load the desired number of punch devices 101 each loaded with samples onto a respective piston of the piston array. The punch devices are then loaded into a receiving array which may have a similar configuration (such as a similar structural, size, and/or shape configuration) to the piston array. The receiving array is mounted onto a substrate (e.g., a receiving substrate as described herein, such as glass slide used to construct a flow cell) to form an assembly.
Figure 17A:
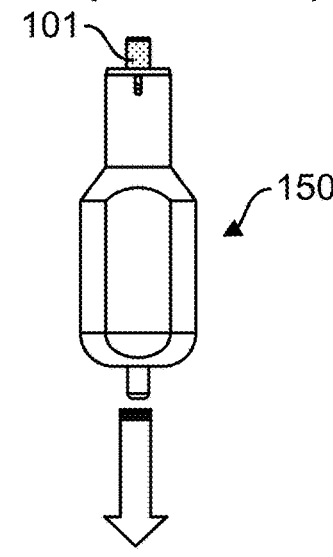
Figure 17A:
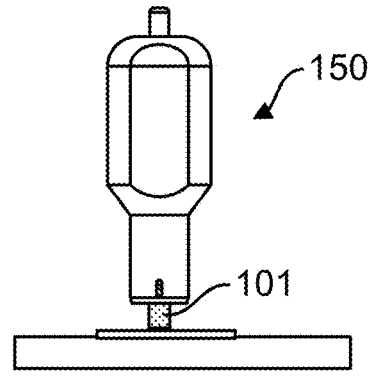
Figure 17B:
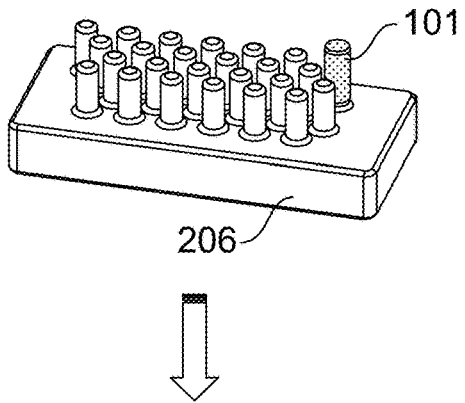
Figure 17B:
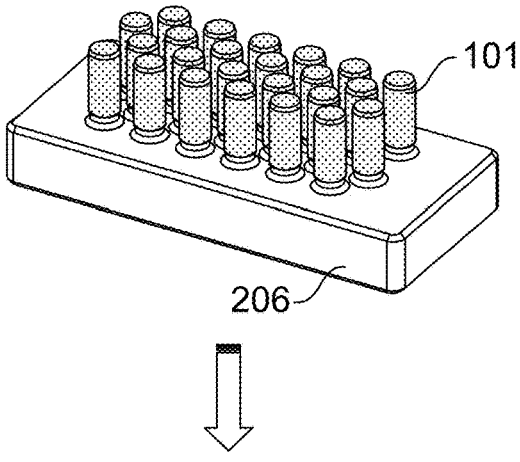
Figure 17B:
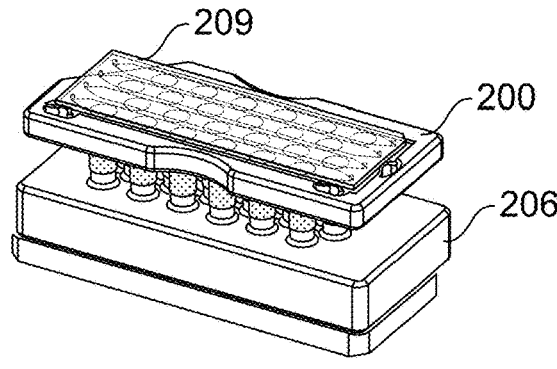
Figure 17C:
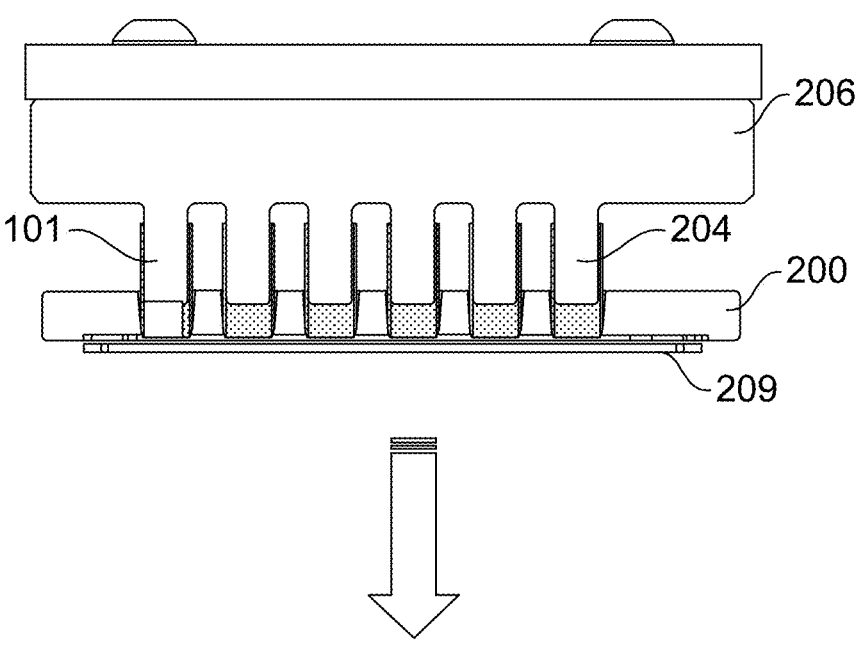
Figure 17C:
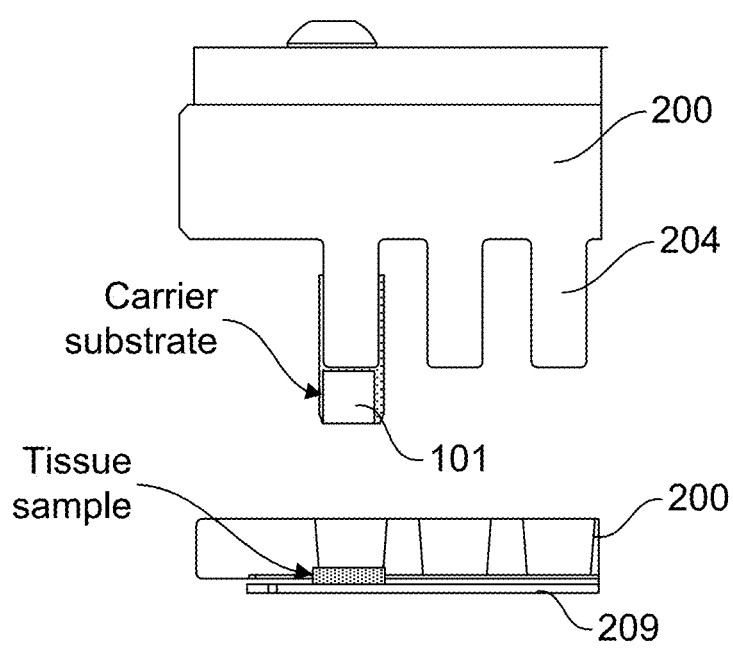

FIGS. 17A-17C show a workflow describing an embodiment of sample manipulation using the systems described herein. With reference to Step 1 of FIG. 17A, a punch device 101 is provided. The punch device 101 is coupled to a punch tool 150, as shown in Step 2, Pursuant to Step 3, the punch tool 150 is used to cut a sample and obtain a loaded punch device as shown in Step 3. With reference now to Step 4 of FIG. 17B, the loaded punch tool 101 is mounted onto the piston array 206 by inserting a piston or rod 204 of the piston array 206 into the punch tool 101. The punch tool 101 thus has a rod 204 inserted within the internal lumen of the punch tool 101. In Step 5 of FIG. 17B, additional punch tools 101 can each be loaded onto respective rods of the piston array 206 such that the piston array 206 is loaded with a plurality of loaded punch tools. In Step 6, a receiving array 200 is coupled to the piston array 206 such that each rod 204 (loaded with a punch tool 101) aligns with a corresponding receptacle of the receiving array 200. A receiving substrate such as a glass slide 209 is coupled to the receiving array 200. The glass slide may contain one or more channels. Alternatively, the glass slide 209 may be functionalized with a polymer and/or a coupling agent. The receiving array may contain an indentation, recession, or suitable pocket for receiving the glass slide. One or more retention mechanisms may be included with the receiving array for securing and aligning the glass slide. The rods 204 are then plunged into each hollow punch device 101 in a piston manner so that the rods 204 expel the sample portions onto the receiving substrate (e.g., glass slide.) As shown in Step 7 of FIG. 17C, the assembly comprised of the receiving array 200, glass slide 209, loaded punch tools 101 can then be turned over or rotated about 180 degrees to aid forcing the biological sample to remain in contact with the receiving substrate 209. Following incubation on a heat plate, in Step 8, the receiving array 200, rods 204, and punch devices 101 are removed from the receiving array 200 such that the tissue sample is retained on the receiving substrate (glass slide 209). The carrier substrate remains on the rod 204 thereby leaving the tissue sample on the glass slide 209. A second glass slide (not shown in FIG. 17B) may then be affixed to the first glass slide 209. The second glass slide may include an indentation to provide a channel. For example, the second glass slide may be etched to include 1, 2, 3, 4, 5, 6, 7, or 8 fluidically independent channels or reaction vessels. The two glass slides, once bonded together, may be referred to as a flow cell assembly. The flow cell assembly may include a first solid support, a gasket, and a second solid support, wherein the gasket forms reaction chamber (e.g., the channel) of the flow cell assembly. In embodiments, the flow cell assembly includes a first solid support and a second solid support, wherein the second solid support includes a spacer structure which forms one or more channels. In embodiments, the first and second solid supports are bonded together to form a closed reaction vessel. In embodiments, the first solid support or the second solid support includes an inlet port and an outlet port (e.g., ports to introduce and remove reagents from the channel). In embodiments, the first solid support includes an inlet port and an outlet port. In embodiments, the second solid support includes an inlet port and an outlet port. In embodiments, the first solid support includes an inlet port. In embodiments, the second solid support includes an inlet port. In embodiments, the first solid support includes an outlet port. In embodiments, the second solid support includes an outlet port.

In embodiments, the flow cell assembly includes a frame configured to retain the flow cell assembly. The frame can be configured to retain the flow cell such that a maximal surface area of the flow cell can be available to be exposed to an optical lens (e.g., the optical lens of a nucleic acid sequencing device). The optical lens (e.g., the optical lens of the sequencing device) can be configured to detect excitation, emission, or other signals present on the flow cell. The frame can be configured to retain the flow cell such that a maximal surface area of the flow cell can be available to be in contact with the receiver of a nucleic acid sequencer. The retaining of the flow cell further can include constraining a first, a second, a third, a fourth, a fifth, and a sixth degree of freedom of the flow cell. The frame can be an injection molded frame. The handle can be a raised handle. The frame can be further configured to provide a gap between a work surface and the flow cell. The frame further can include at least one ferromagnetic pin. The at least one biasing feature can be a spring finger. The at least one biasing feature can be a tab. The at least one biasing feature can be a wedge. The flow cell can further include a microchip. The microchip can be an electronically erasable programmable read only memory (EEPROM) chip or Radio Frequency Identification (RFID) tag.

The solid supports for some embodiments have at least one surface located within a flow cell or reaction chamber. Flow cells provide a convenient format for housing an array of clusters produced by the methods described herein, in particular when subjected to sequencing (e.g., SBS) or other detection technique that involves repeated delivery of reagents in cycles.

In embodiments, the first solid support includes a glass substrate. In embodiments, the second solid support includes a glass substrate. In embodiments, the glass substrate is a borosilicate glass substrate with a composition including $SiO_2$, $Al_2O_3$, $B_2O_3$, $Li_2O$, $Na_2O$, $K_2O$, MgO, CaO, SrO, BaO, ZnO, $TiO_2$, $ZrO_2$, $P_2O_5$, or a combination thereof (see e.g., U.S. Pat. No. 10,974,990). In embodiments, the glass substrate is an alkaline earth boro-aluminosilicate glass substrate.

In embodiments, the second solid support includes a channel bored into the second solid support. In embodiments, the second solid support includes a plurality of channels bored into the second solid support. In embodiments, the second solid support includes 2 channels bored into the second solid support. In embodiments, the second solid support includes 3 channels bored into the second solid support. In embodiments, the second solid support includes 4 channels bored into the second solid support. In embodiments, the width of the channel is from about 1 to 5 mm. In embodiments, the width of the channel is from about 5 to 10 mm. In embodiments, the width of the channel is from about 10 to 15 mm. In embodiments, the width of the channel is from about 5 mm. In embodiments, the width of the channel is from about 11 mm.

In embodiments, the second solid support includes a gasket, wherein the gasket defines the reaction chamber. In embodiments, the gasket includes silicone, polyimide, fluorocarbon elastomer, ethylene propylene diene, polychloroprene, polytetrafluoroethylene, nitrile rubber, butyl rubber, natural rubber, thermoplastic elastomer, or a combination thereof. In embodiments, the second solid support includes a spacer structure which forms a channel. The spacer structure may be made of any suitable material, for example resin, glass, plastic, silicon, an adhesive, or a combination thereof. In embodiments, the spacer includes a first adhesive in contact with the functionalized glass slide and second adhesive in contact with the second solid support.

In an aspect is provided a system for manipulating a biological sample. In embodiments, the system includes a punch device configured to form a sample portion of the biological sample, the punch device forming an internal cavity (e.g., the punch device includes shaft) and having a bottom edge sufficiently sharp to cut through the biological sample; a receiving substrate; and a piston sized and shaped to fit within the internal cavity of the punch device, wherein the piston inserts into the internal cavity of the punch device to expel the sample portion (e.g., all or a portion thereof) from the punch device onto the receiving substrate.

In embodiments, the system includes a punch device configured to form a sample portion of the biological sample, the punch device forming an internal cavity and having a bottom edge sufficiently sharp to cut through the biological sample; a receiving substrate; and a piston sized and shaped to fit within the internal cavity of the punch device, wherein the piston inserts into the internal cavity of the punch device to expel the sample portion from the punch device onto the receiving substrate (e.g., a solid support, as described herein).

In embodiments, the system includes a punch device configured to form a sample portion of the biological sample, the punch device forming an internal cavity and having a bottom edge sufficiently sharp to cut through the biological sample; a receiving array having a receptacle sized and shaped to receive at least a portion of the punch device; a piston array having a piston sized and shaped to fit within the internal cavity of the punch device, wherein the piston inserts into the internal cavity of the punch device to expel the sample portion from the punch device into the at least one receptacle of the receiving array.

In embodiments, the receiving substrate includes a functionalized glass surface or a functionalized plastic surface. Functionalization, as used herein, refers to a modification of the original surface. For example, functionalization may include topographical modifications (e.g., groves, posts, etching), chemical modifications (e.g., binding one or more compounds to the surface to alter the surface charge or bioconjugate reactive moieties on the surface), biological modifications (e.g., immobilizing one or more heparin proteins, heparin sulfate binding proteins, peptide sequences, growth factors, fibronectin, laminin, or collagen), or plasma treatment on reactive glass to generate bioconjugate reactive moieties on the surface. In embodiments, the receiving substrate (e.g., the receiving array) includes a plurality of receptacles arranged in a first pattern. In embodiments, the receiving substrate is a glass solid support. In embodiments, the receiving substrate is a glass solid support which is further assembled into a closed container, wherein the container includes an inlet and outlet port(e.g., a flow cell).

In embodiments, the receiving substrate is functionalized with an RGD peptide or YIGSR peptide. RGD peptide is one of the most physiologically ubiquitous binding motifs commonly used, which is found in many natural adhesive proteins such as fibronectin, vitronectin, laminin and collagen type I.

In embodiments, the receiving substrate is functionalized with one or more synthetic chemical molecules. In embodiments, the receiving substrate includes dimethyl sulfoxide (DMSO), all-trans retinoic acid (RA), dynorphin B, ascorbic acid. In embodiments, the receiving substrate includes one or more bioconjugate reactive moieties (e.g., carboxyl or amine groups) on the surface of the receiving substrate. In embodiments, the receiving substrate includes a glass solid support that is functionalized by contacting the glass solid support in triethanolamine buffer containing glutaraldehyde and 1-hydroxbenzol (HOBt), followed by contacting with 1-ethyl-3-(3-dimethylaminopropyl) carbodiimide (EDC) and/or N-hydroxysuccinimide (NHS). In embodiments, the functionalized glass surface includes (3-aminopropyl)triethoxysilane (APTES), (3-Aminopropyl)trimethoxysilane (APTMS), γ-Aminopropylsilatrane (APS), N-(6-amino-hexyl)aminomethyltriethoxysilane (AHAMTES), polyethylenimine (PEI), 5,6-epoxyhexyltriethoxysilane, or triethoxysilylbutyraldehyde, or a combination thereof. In embodiments, the functionalized glass surface includes (3-aminopropyl)triethoxysilane (APTES). In embodiments, the functionalized glass surface includes (3-Aminopropyl) trimethoxysilane (APTMS). In embodiments, the functionalized glass surface includes γ-Aminopropylsilatrane (APS). In embodiments, the functionalized glass surface includes N-(6-aminohexyl)aminomethyltriethoxysilane (AHAMTES). In embodiments, the functionalized glass surface includes polyethylenimine (PEI). In embodiments, the functionalized glass surface includes 5,6-epoxyhexyltriethoxysilane. In embodiments, the functionalized glass surface includes triethoxysilylbutyraldehyde. In embodiments, the receiving substrate is a functionalized glass surface or a functionalized plastic surface. In embodiments, the functionalized glass surface is functionalized with APTES, APTMS, APS, or AHAMTES.

In embodiments, the receiving substrate includes a polymer attached to the solid support. In embodiments, the polymer is polylysine, poly(2-dimethylaminoethyl methacrylate) (PDMAEMA), chitosan, poly(amidoamine) (PAMAM), polyvinylamine (PVAm), or poly(allylamine hydrochloride) (PAH). In embodiments, the receiving substrate includes a coupling agent. As used herein, the term "coupling agent" refers to a molecule capable of attaching two distinct entities such as molecules, surfaces, or materials, together by forming a chemical bond or complex. A coupling agent typically possesses functional groups (e.g., bioconjugate reactive groups) that allow it to interact with and bind to specific sites on both entities, thereby bridging them together. In embodiments, the coupling agent is (i) attached to the polymer or resist attached to the first solid support and (ii) attached to a component of the cell or tissue (e.g., attached to a biomolecule of a cell). In embodiments, the coupling agent modifies the surface hydrophilicity of the first solid support to provide a surface useful for cell adhesion via electrostatic and/or covalent interactions between the coupling agents and the macromolecules in the cell or tissue to be detected. Non-limiting examples of a coupling agent, includes but is not limited to, (3-aminopropyl)triethoxysilane (APTES), (3-Aminopropyl)trimethoxysilane (APTMS), γ-Aminopropylsilatrane (APS), N-(6-aminohexyl)aminomethyltriethoxysilane (AHAMTES), and polyethylenimine (PEI).

In embodiments, the receiving substrate further comprises a resist. In embodiments, the resist is substantially transparent. For example, the resist is attached to the receiving substrate (e.g., a glass slide). In embodiments, the receiving substrate (i.e., the solid support) includes a photoresist. As the name suggests, the photoresist (alternatively referred to as a resist) is an active material layer that can be patters by selective exposure and must "resist" chemical/physical attach of the underlying substrate. In embodiments, the solid support includes a glass substrate having a surface coated in silsesquioxane resist (e.g., polyhedral oligosilsesquioxanemethacrylate (POSS)), an epoxy-based polymer resist (e.g., SU-8 as described in U.S. Pat. No. 4,882,245), poly (vinylpyrrolidone-vinyl acrylic acid) copolymer resist (e.g., as described in U.S. Pat. No. 7,467,632), or novolaks resist, bisazides resist, or a combination thereof (e.g., as described in U.S. Pat. No. 4,970,276). In embodiments, the solid support includes a photoresist and polymer layer, wherein the photoresist is between the solid support and the polymer layer. Suitable photoresist compositions are known in the art, such as, for example the compositions and resins described in U.S. Pat. Nos. 6,897,012; 6,991,888; 4,882,245; 7,467,632; 4,970,276, each of which is incorporated herein by reference in their entirety. In embodiments, the solid support includes a photoresist and polymer layer, wherein the photoresist is covalently attached to the solid support and covalently attached to the polymer layer. In embodiments, the resist is an amorphous (non-crystalline) fluoropolymer (e.g., CYTOP® from Bellex), a crystalline fluoropolymer, or a fluoropolymer having both amorphous and crystalline domains. In embodiments, the resist is a suitable polysiloxane, such as polydimethylsiloxane (PDMS). In embodiments, the resist is a crosslinked polymer matrix. In embodiments, the resist includes silsesquioxane molecules. In embodiments, the resist includes polymerized epoxy-containing monomers, or polymerized poly(vinylpyrrolidone-vinyl acrylic acid) copolymers. In embodiments, the solid support includes a glass substrate having a surface coated in silsesquioxane resist (e.g., polyhedral oligosilsesquioxanemethacrylate (POSS)), an epoxy-based polymer resist (e.g., SU-8 as described in U.S. Pat. No. 4,882,245), poly(vinylpyrrolidone-vinyl acrylic acid) copolymer resist (e.g., as described in U.S. Pat. No. 7,467,632), or novolaks resist, bisazides resist, or a combination thereof (e.g., as described in U.S. Pat. No. 4,970,276).

In embodiments, the solid support includes a photoresist. A photoresist is a light-sensitive polymer material used to form a patterned coating on a surface. The process begins by coating a substrate (e.g., a glass substrate) with a light-sensitive organic material. A mask with the desired pattern is used to block light so that only unmasked regions of the material will be exposed to light. In the case of a positive photoresist, the photo-sensitive material is degraded by light and a suitable solvent will dissolve away the regions that were exposed to light, leaving behind a coating where the mask was placed. In the case of a negative photoresist, the photosensitive material is strengthened (either polymerized or cross-linked) by light, and a suitable solvent will dissolve away only the regions that were not exposed to light, leaving behind a coating in areas where the mask was not placed. In embodiments, the solid support includes an epoxy-based photoresist (e.g., SU-8, SU-8 2000, SU-8 3000, SU-8 GLM2060). In embodiments, the solid support includes a negative photoresist. Negative refers to a photoresist whereby the parts exposed to UV become cross-linked (i.e., immobilized), while the remainder of the polymer remains soluble and can be washed away during development. In embodiments, the solid support includes an Off-stoichiometry thiol-enes (OSTE) polymer (e.g., an OSTE resist). In embodiments, the solid support includes a Hydrogen Silsesquioxane (HSQ) polymer (e.g., HSQ resist).

In embodiments, the solid support includes a resist (e.g., a nanoimprint lithography (NIL) resist). Nanoimprint resists can include thermal curable materials (e.g., thermoplastic polymers), and/or UV-curable polymers. In embodiments, the solid support is generated by pressing a transparent mold possessing the pattern of interest (e.g., the pattern of wells) into photo-curable liquid film, followed by solidifying the liquid materials via a UV light irradiation. Typical UV-curable resists have low viscosity, low surface tension, and suitable adhesion to the glass substrate. For example, the solid support surface, but not the surface of the wells, is coated in an organically modified ceramic polymer (ORMOCER®, registered trademark of Fraunhofer-Gesellschaft zur Förderung der angewandten Forschung e. V. in Germany). Organically modified ceramics contain organic side chains attached to an inorganic siloxane backbone. Several ORMOCER® polymers are now provided under names such as "Ormocore", "Ormoclad" and "Ormocomp" by Micro Resist Technology GmbH. In embodiments, the solid support includes a resist as described in Haas et al Volume 351, Issues 1-2, 30 Aug. 1999, Pages 198-203, US 2015/0079351A1, US 2008/0000373, or US 2010/0160478, each of which is incorporated herein by reference. In embodiments, the solid support surface is coated in an organically modified ceramic polymer (ORMOCER®, registered trademark of Fraunhofer-Gesellschaft zur Förderung der angewandten Forschung e. V. in Germany).

In embodiments, the solid support includes a polymer layer. In embodiments, the polymer layer includes polymerized units of alkoxysilyl methacrylate, alkoxysilyl acrylate, alkoxysilyl methylacrylamide, alkoxysilyl methylacrylamide, or a copolymer thereof. In embodiments, the polymer layer includes polymerized units of alkoxysilyl methacrylate. In embodiments, the polymer layer includes polymerized units of alkoxysilyl acrylate. In embodiments, the polymer layer includes polymerized units of alkoxysilyl methylacrylamide.

In embodiments, the polymer layer includes polymerized units of alkoxysilyl methylacrylamide. In embodiments, the polymer layer includes glycidyloxypropyl-trimethyloxysilane. In embodiments, the polymer layer includes methacryloxypropyl-trimethoxysilane. In embodiments, the polymer layer includes polymerized units of -continued , or or a copolymer thereof. In embodiments, the polymer layer is an organically-modified ceramic polymer. In embodiments, the polymer includes polymerized monomers of alkoxysilyl polymers, such as

,

, or

In embodiments, the solid support includes polymerized units of

In embodiments, the solid support includes polymerized units of

In embodiments, the solid support includes polymerized unites of

.

In embodiments, the polymer layer includes one or more ceramic particles, (e.g., silicates, aluminates, and titanates). In embodiments, the polymer layer includes titanium dioxide, zinc oxide, and/or iron oxide.

In embodiments, the receiving substrate (e.g., the solid support) includes a photoresist, alternatively referred to herein as a resist. A "resist" as used herein is used in accordance with its ordinary meaning in the art of lithography and refers to a polymer matrix (e.g., a polymer network). In embodiments, the photoresist is a silsesquioxane resist, an epoxy-based polymer resist, poly(vinylpyrrolidone-vinyl acrylic acid) copolymer resist, an Off-stoichiometry thiol-enes (OSTE) resist, amorphous fluoropolymer resist, a crystalline fluoropolymer resist, polysiloxane resist, or a organically modified ceramic polymer resist. In embodiments, the photoresist is a silsesquioxane resist. In embodiments, the photoresist is an epoxy-based polymer resist. In embodiments, the photoresist is a poly(vinylpyrrolidone-vinyl acrylic acid) copolymer resist. In embodiments, the photoresist is an Off-stoichiometry thiol-enes (OSTE) resist. In embodiments, the photoresist is an amorphous fluoropolymer resist. In embodiments, the photoresist is a crystalline fluoropolymer resist. In embodiments, the photoresist is a polysiloxane resist. In embodiments, the photoresist is an organically modified ceramic polymer resist. In embodiments, the photoresist includes polymerized alkoxysilyl methacrylate polymers and metal oxides (e.g., $SiO_2$, ZrO, MgO, $Al_2O_3$, $TiO_2$ or $Ta_2O_5$). In embodiments, the photoresist includes polymerized alkoxysilyl acrylate polymers and metal oxides (e.g., $SiO_2$, ZrO, MgO, $Al_2O_3$, $TiO_2$ or $Ta_2O_5$). In embodiments, the photoresist includes metal atoms, such as Si, Zr, Mg, Al, Ti or Ta atoms. In embodiments, the solid support is a glass slide about 75 mm by about 25 mm. In embodiments, the solid support includes a resist (e.g., a photoresist or nanoimprint resist including a crosslinked polymer matrix attached to the solid support). Typical solid supports are planar (i.e., flat) glass, often 75×25 mm and 1 mm thick, or 3×1-inch and 1 mm thick, and are used to hold a specimen. In histopathology applications the glass slides are ground and polished for safe handling and include a frosted area painted for labeling purposes. Distinguishing between glass utilized in enological applications (wine glasses) and glass employed in histological laboratories, it is pertinent to note the compositional differences. In histological applications, borosilicate glass is predominantly utilized, attributed to its superior properties concerning its transmittance and reflectivity properties.

Borosilicate glass is characterized by its high clarity and minimal light absorption, allowing for the transmission of a greater spectrum of light. Such a property is essential in microscopy, as it ensures that more light passes through the specimen, thereby providing clearer, more detailed visualizations of the sample under observation. Enhanced light transmittance is crucial for accurate and detailed microscopic examinations, particularly in high-resolution imaging. Additionally, the reduced reflectivity of borosilicate glass minimizes the interference caused by surface reflections, thus enhancing the quality of the image. Low reflectivity is especially beneficial when examining specimens that require high magnification or intricate detail observation, as it ensures that the light is focused on the specimen rather than being reflected off the surface. The absence of additives in borosilicate glass during the manufacturing process contributes to its enhanced purity, yielding superior optical and thermal characteristics.

In embodiments, the tissue is immobilized to the receiving substrate by covalently binding the tissue to one or more bioconjugate reactive moieties of the receiving substrate. In embodiments, the tissue is immobilized to the receiving substrate by non-covalently binding the tissue to the receiving substrate. For non-covalent binding, the tissue sections attach to the receiving substrate surface due to surface interactions, such as Van der Waal forces, electrostatic forces, hydrophobic interactions and hydrogen bonds. The physical adsorption efficiency can be enhanced by treating the material with air plasma to increase its hydrophilicity.

In embodiments, the receiving substrate is a microplate assembly. In embodiments, the microplate assembly includes at least one microplate section and a planar support positioned on a bottom of the at least one microplate section. In embodiments, the microplate assembly includes integrated unit, wherein the frame and microplate section are fused together or otherwise inseparable. For example, the microplate assembly may include a microwell insert, wherein a plurality of wells are bored directly into the microwell insert. The integrated unit may have dimensions as provided and described by American National Standards Institute (ANSI) and Society for Laboratory Automation And Screening (SLAS); for example the tolerances and dimensions set forth in ANSI SLAS 1-2004 (R2012); ANSI SLAS 2-2004 (R2012); ANSI SLAS 3-2004 (R2012); ANSI SLAS 4-2004 (R2012); and ANSI SLAS 6-2012, which are incorporated herein by reference. The microplate insert does not necessarily include any wells. For example, the microplate insert may be configured to retain a microscope slide, wherein the microplate insert provides a plurality of defined wells, and may be referred to a microwell insert. In embodiments, the microwell insert includes a thermoplastic. In embodiments, the microwell insert includes a thermoplastic polyetherimide (PEI), for example ULTEM™ PEI PolyEtherImide (PEI). In embodiments, the microwell insert is glass. In embodiments, the microwell insert is ceramic. In embodiments, the microwell insert is steel. In embodiments, the microwell insert is glass, wherein the plurality of wells are bored directly into the glass.

In embodiments, the receiving array is a microplate array and includes 2, 4, 6, 12, 24, 48, 96, 384 or 1536 wells. In embodiments, the microplate array includes 24, 48, 96, or 384 wells. In embodiments, the microplate array includes 24 wells. In embodiments, the microplate array includes 48 wells. In embodiments, the microplate array includes 96 wells. In embodiments, the microplate array includes 384 wells. In embodiments, the dimensions of the microplate conform to the standards provided by the American National Standards Institute (ANSI) and Society For Laboratory Automation And Screening (SLAS); for example the tolerances and dimensions set forth in ANSI SLAS 1-2004 (R2012); ANSI SLAS 2-2004 (R2012); ANSI SLAS 3-2004 (R2012); ANSI SLAS 4-2004 (R2012); and ANSI SLAS 6-2012. In embodiments, the microplate has a rectangular shape that measures 127.7 mm±0.5 mm in length by 85.4 mm±0.5 mm in width, and includes 6, 12, 24, 48, or 96 wells. In embodiments, the microplate has a rectangular shape that measures 127.7 mm±0.5 mm in length by 85.4 mm±0.5 mm in width, and includes 6, 12, 24, 48, or 96 wells, wherein each well has an average diameter of about 5-7 mm. In embodiments, the microplate has a rectangular shape that measures 127.7 mm±0.5 mm in length by 85.4 mm±0.5 mm in width, and includes 6, 12, 24, 48, or 96 wells, wherein each well has an average diameter of about 6 mm. In embodiments, the microplate includes wells that are formatted for compatibility with automated reagent loading equipment (e.g., pipetting robots) that exists and are in common usage in laboratories and manufacturing facilities. In embodiments, the microplate array includes a plurality of wells. In embodiments, the microplate array includes a solid support including a plurality of openings and a planar support attached to the solid support. In embodiments, a bottom region of the microplate array is glass. In embodiments, a bottom region of the microplate section is a functionalized solid support (i.e., a planar support). In embodiments, the planar support is removably attached to the microplate array.

In embodiments, the receptacles (alternatively referred to as wells) of the array are separated from each other by about 1 mm to about 10 mm. In embodiments, the well is about 3 mm in diameter. In embodiments, the well is about 3.6 mm in diameter. In embodiments, the well is about 4 mm in diameter. In embodiments, the well is about 5 mm in diameter. In embodiments, the well is about 6 mm in diameter. In embodiments, the well is about 6.5 mm in diameter. In embodiments, the well is about 7 mm in diameter. In embodiments, the well is about 7.5 mm in diameter. In embodiments, the well is about 8 mm in diameter. In embodiments, the well is 5 mm in diameter. In embodiments, the well is 6 mm in diameter. In embodiments, the well is 6.5 mm in diameter. In embodiments, the well is 7 mm in diameter. In embodiments, the well is 7.5 mm in diameter. In embodiments, the well is 8 mm in diameter. In embodiments, the well is about 6 to 12 mm in depth. It is also understood that the size of the wells on the array can be of various sizes and will ultimately depend on the systems and/or apparatus used to analyze later reactions.

In embodiments, the receiving substrate forms part of a flow cell assembly. In embodiments, the flow cell assembly includes a glass solid support. Fused silica or borosilicate glass is typically used due to their optical clarity, chemical resistance, low autofluorescence, and stability. The channels and/or wells within the flow cell are formed through microfabrication techniques such as photolithography, etching, or micro-molding. These channels are designed to be small and precise, allowing controlled flow and management of reagents and samples. In embodiments, the channels are etched into the glass solid support. In embodiments, a channel spacer is attached to the glass solid support. For example, a channel spacer or gasket is engineered to maintain uniform thickness and channel dimensions. In embodiments, the channels are bored into the second solid support to form the channels. The flow cell assembly may further include a second glass support bonded to the channel spacer.

Alternatively, the flow cell assembly may include a second glass support bonded to the first glass solid support.

Microplates with clear-bottom wells facilitate optical measurements from the bottom, e.g., inverted high-resolution microscopy and imaging. For optical detection modalities, an optically transparent planar support is useful. Microplate color may be tuned to maximize the signal-to-background ratio. Black microplates are well-suited for fluorescence-based readouts; the black color can reduce well-to-well crosstalk, while also reducing background autofluorescence. In embodiments, the microplate includes a thermoplastic. In embodiments, the microplate includes a thermoplastic polyetherimide (PEI), for example ULTEM™ PEI PolyEtherImide (PEI). In embodiments, the microplate is glass. In embodiments, the microplate is ceramic. In embodiments, the microplate includes steel attached to a glass bottom. In embodiments, the microplate is glass, wherein a plurality of wells are bored directly into the glass. In embodiments, the microplate does not degrade at temperatures greater than 50° C., 60° C., 70° C., 80° C., 90° C., 100° C., 110° C., or 120° C. In embodiments, the microplate does not degrade at temperatures greater than 50° C., 60° C., 70° C., 80° C., 90° C., or 100° C. In embodiments, the microplate does not degrade at 100° C. In embodiments, the microplate bonded to the planar support does not degrade or result in sample contamination at elevated temperatures (e.g., 80° C.-120° C.). The microplate may be used to detect biomolecules (e.g., nucleic acids). Typically, the nucleic acids need to be amplified. In embodiments the term "amplified" refers to a method that includes a polymerase chain reaction (PCR). Conditions conducive to amplification (i.e., amplification conditions) are well known and often include at least a suitable polymerase, a suitable template, a suitable primer or set of primers, suitable nucleotides (e.g., dNTPs), a suitable buffer, and application of suitable annealing, hybridization and/or extension times and temperatures. Amplification conditions may cycle between different temperatures, often involving a large temperature gradient (e.g., 20° C.-40° C.). Additionally, samples embedded in formalin may require additional protocols to render biomolecules available. Heat induced epitope retrieval (HIER) uses heat coupled with buffered solutions to recover antigen reactivity in formalin fixed paraffin embedded tissue samples. Typical HIER methods include increasing the temperature from 25° C. to 95° C.-120° C., if utilizing a water bath or pressure enhanced temperature device (e.g., a pressure cooker). In embodiments, the microplate includes a microplate insert and a planar support attached to the microplate insert. In embodiments, a the planar support can include glass (e.g., a glass slide) that has been coated with a substance or otherwise modified to confer conductive properties to the glass. In some embodiments, a glass slide can be coated with a conductive coating. In some embodiments, a conductive coating includes tin oxide (TO) or indium tin oxide (ITO). In some embodiments, a conductive coating includes a transparent conductive oxide (TCO). In some embodiments, a conductive coating includes aluminum doped zinc oxide (AZO). In some embodiments, a conductive coating includes fluorine doped tin oxide (FTO).

In embodiments, the microplate includes a plurality of wells. In embodiments, each well includes about 10,000 to 100,000 cells per well. In embodiments, each well includes at least 1000, 2000, 3000, 4000, 5000, 6000, 7000, 8000, 9000 or at least 10,000 cells per well. In embodiments, each well includes about 10,000, 20,000, 30,000, 40,000, 50,000, 60,000, 70,000, 80,000, 90,000 or at least 100,000 cells per well.

In embodiments, the receiving substrate includes (3-aminopropyl)triethoxysilane (APTES), (3-Aminopropyl) trimethoxysilane (APTMS), γ-Aminopropylsilatrane (APS), N-(6-aminohexyl)aminomethyltriethoxysilane (AHAMTES), polyethylenimine (PEI), 5,6-epoxyhexyltriethoxysilane, or triethoxysilylbutyraldehyde, or a combination thereof. In embodiments, the receiving substrate includes (3-aminopropyl)triethoxysilane (APTES). In embodiments, the receiving substrate includes (3-Aminopropyl)trimethoxysilane (APTMS). In embodiments, the receiving substrate includes γ-Aminopropylsilatrane (APS). In embodiments, the receiving substrate includes N-(6-aminohexyl)aminomethyltriethoxysilane (AHAMTES). In embodiments, the receiving substrate surface includes polyethylenimine (PEI). In embodiments, the receiving substrate includes 5,6-epoxyhexyltriethoxysilane. In embodiments, the receiving substrate includes triethoxysilylbutyraldehyde. In embodiments, the receiving substrate is a functionalized glass surface or a functionalized plastic surface. In embodiments, the functionalized glass surface is functionalized with APTES, APTMS, APS, or AHAMTES.

Figures 9A, 9B:
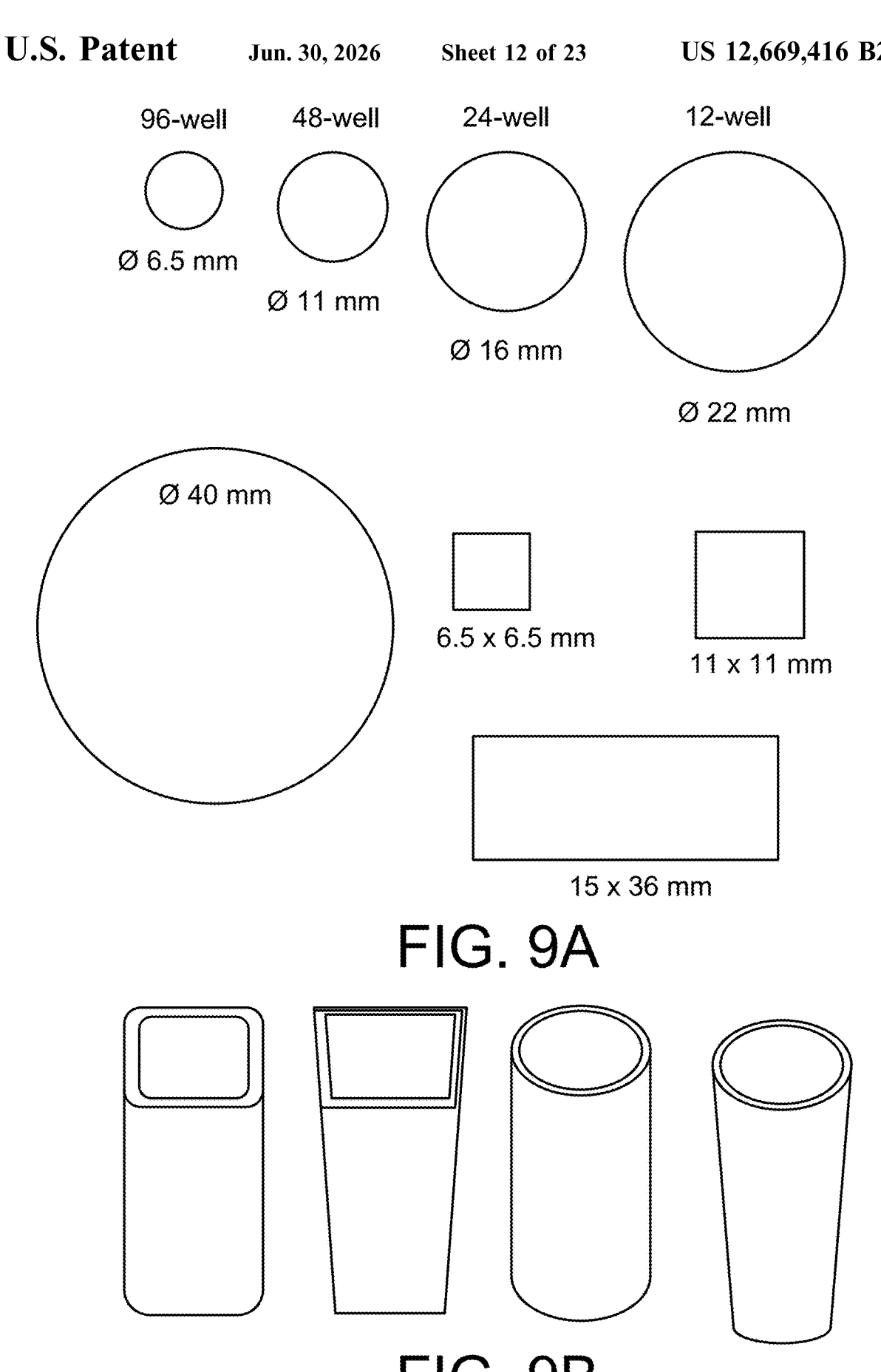
FIGS. 9A-9D is an illustration of the different diameters and dimensions of the devices contemplated herein. For example, the diameters of the sample portions may be cut to fit into individual wells in 96-well, 48-well, 24-well, and 12-well plates, and/or tissue capture areas of several com-mercial products. The cutting devices, as described herein, permit collecting biological samples of various dimensions. The devices and methods described herein may be used to cut a sample to any of the dimensions depicted in FIG. 9A. The shapes of the punch device may vary and may be (in non-limiting examples) cuboid, cylindrical, pyramidal, coni-cal, or frustoconical as illustrated in FIG. 9B.
Figure 9C:
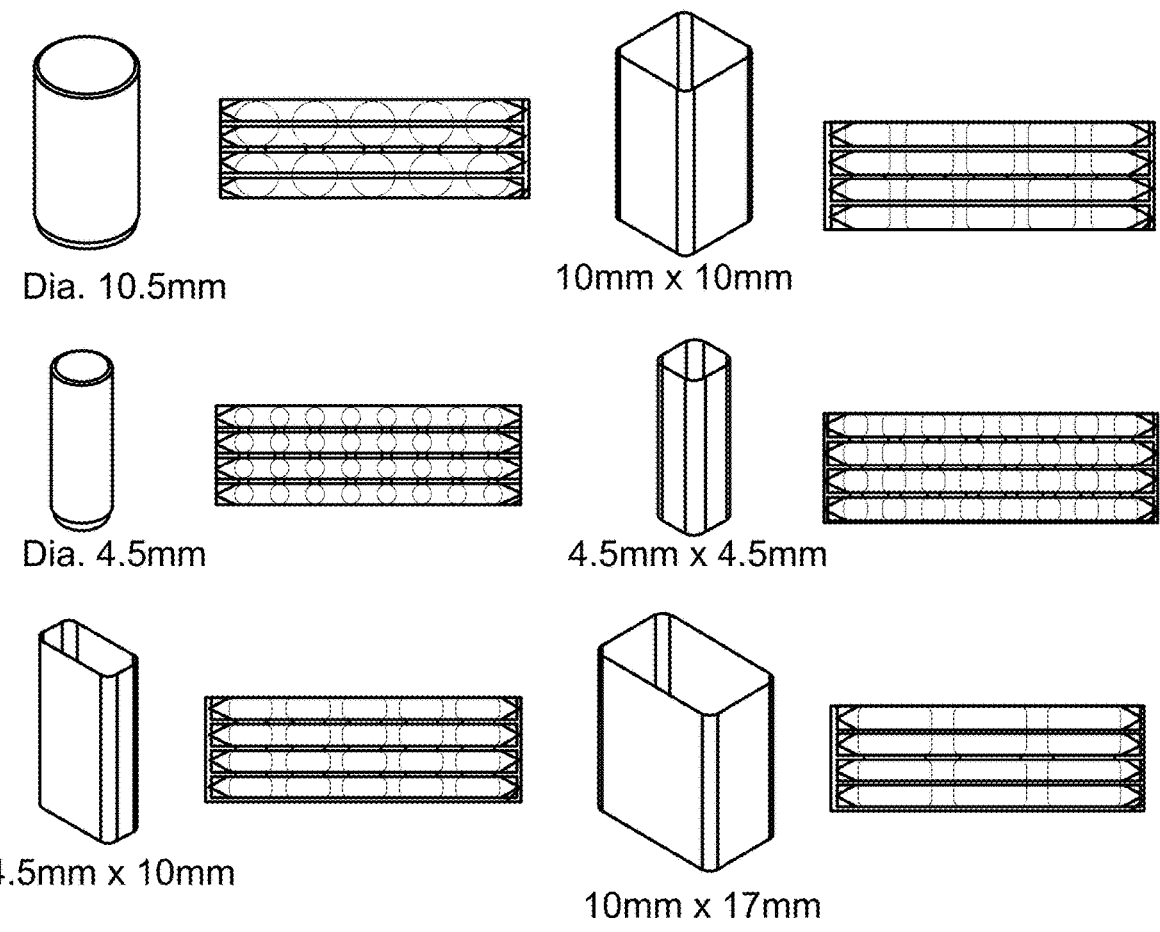

In embodiments, the punch device includes a top end and a bottom end, wherein the bottom end is distal to the top end and includes the bottom edge. In embodiments, the punch device is cylindrical. In embodiments, the punch device is hollow. In embodiments, the punch device includes a shaft, wherein the shaft forms the internal cavity. In embodiments, the punch device includes a column body having an open upper end, an open lower end, and an open channel between the upper and lower end of the column body. The column body is a tube having two open ends connected by an open channel, sometimes referred to as a through passageway. The tube can be in any shape, including but not limited to cuboid, cylindrical, pyramidal, conical, or frustoconical, and of any dimensions consistent with the function of the punch device as described herein, as illustrated in FIG. 9B and FIG. 9C. In embodiments, the punch device has a cross-sectional shape that is cylindrical, square, oval, or rectangular, having a characteristic length and width. For example, a cylindrical punch device includes a length that is typically the distance from one end of the punch device to the other, measured along its axis, and the width in a cylindrical punch is the same as its diameter. For a rectangular punch, the length corresponds to the longer dimension of the rectangle and the width corresponds to the shorter dimension of the rectangle. For a square punch the length is equal to the side of the square and the width is the same as the length since all sides of a square are equal. For an oval punch, the length corresponds to the longest dimension of the oval, typically referred to as the major axis, and the width corresponds to the shortest dimension of the oval, typically referred to as the minor axis.

In embodiments, the punch device includes one or more bores, slots, seats, notches, or other structures sized and shaped to align and/or retain the punch device within the receiving array. In embodiments, the punch device includes other texture such as grooves, indentations, rippling, stippling, or the like, to improve grip. In embodiments, each punch device comprises an alignment feature configured to mate and align the punch device and receptacle in a proper orientation.

In embodiments, the punch device is configured to cut through the biological sample and a carrier substrate. In embodiments, the bottom edge of the punch device is tapered to facilitate cutting. In embodiments, the bottom edge of the punch device includes one or more blade(s) or sharpened razor(s). In embodiments, the bottom edge of the punch device includes a knife or scalpel edge. In embodiments, the punch device is sufficiently sharp to cut through both the sample portion and the carrier substrate. In embodiments, the bottom edge includes a serrated edge (i.e., jagged edge including a plurality of teeth) to facilitate cutting. In embodiments, the interior of the punch device includes a rough surface (i.e., not smooth). In embodiments, the punch device includes the dimensions (e.g., the internal dimensions) identified in FIG. 9A or FIG. 9C.

In embodiments, the punch device is configured to be positioned in the receptacle in the receiving array with the sample portion in the punch device and the sample portion contacting a bottom of the receptacle of the receiving array.

In embodiments, the punch device includes a gasket (e.g., a silicone or rubber gasket).

In embodiments, the punch device is disposable, which are typically composed of a plastic, but may alternatively be composed of a metal or ceramic. In embodiments, the punch device is reusable (or "non-disposable"), wherein it is capable of being used for its intended purpose multiple times.

In embodiments, the piston inserts into the bottom end of the punch device into the internal cavity of the punch device to expel the sample portion through the top end. In embodiments a portion of the sample portion is expelled from the punch device. In embodiments, the biological sample is expelled from the punch device and the carrier substrate is not expelled from the punch device. In embodiments, the biological sample enters the punch device through one end and exits through the other end. Alternatively, in embodiments, the biological sample enters the punch device through one end and exits through the same end.

In embodiments, the piston is driven manually into the internal cavity of the punch device, wherein a force is applied to the piston. In embodiments, the piston is driven into the internal cavity of the punch device using a spring and/or air pressure. In embodiments, the piston is driven into the internal cavity of the punch device using an actuator (e.g., a solenoid applied downward pressure), a stepper motor, a pneumatic cylinder, or a shape memory alloy (e.g., nickel-titanium or "nitinol"). In embodiments, the actuator is driven manually, by spring, hydraulic, pneumatic, and/or electrical force. In embodiments, the piston includes a seal (e.g., a rubber gasket). In embodiments, the seal is in slidable engagement with the internal cavity of the punch device. When a downward pressure is applied an increase in air pressure facilitates expulsion of the sample portion from the punch device. In embodiments, the diameter of the internal cavity at the top end is greater than the diameter of the internal cavity at the bottom end A range of suitable materials for the punch device, piston, and receiving array are available and known to one of skill in the art. For example, various plastics make for suitable materials, but other materials such as glass, ceramics or metals could be used in some embodiments. In embodiments, the punch device, piston, and receiving array are made from polysulfone, polypropylene, polyethylene, polyethylene-terephthalate, polyethersulfone, polytetrafluoroethylene, cellulose acetate, cellulose acetate butyrate, acrylonitrile PVC copolymer, polystyrene, polystyrene/acrylonitrile copolymer, polyvinylidene fluoride, glass, metal, silica, and combinations of the above listed materials. In embodiments, the receiving array includes a plurality of receptacles arranged in a pattern that complements the first pattern such that a plurality of loaded punch devices and pistons can be inserted into the plurality of receptacles. In embodiments, the receiving array includes a base and a plurality of receptacles extending through the base. In embodiments, the receiving array includes 2, 4, 6, 12, 24, 48, 96, 384, or 1536 pistons. In embodiments, the receiving array includes 12, 24, 48, or 96 pistons. In embodiments, the pattern within a receiving array (and the corresponding piston array) is useful for configuring, aligning, and generating reproducible samples. In embodiments, the pattern of the receiving array is designed to complement a corresponding pattern in the piston array. In embodiments, the receiving array includes 2, 4, 6, 8, 10, 12, 14, 16, 18, 20, 22, 24, 26, 28, 30, 32, 34, 36, 38, 40, 42, 44, 46, or 48 receptacles.

In embodiments, the piston includes a piston head, wherein the piston head is configured to contact the biological sample. In embodiments, the piston head is concave. In embodiments, the piston head is substantially flat. In embodiments, the piston head is convex. In embodiments, the piston head includes a porous material attached at the end (e.g., a thin, low pore volume filter, such as a membrane screen). In embodiments, the piston is cuboid, cylindrical, pyramidal, conical, or frustoconical. In embodiments, the cross-section geometry of the piston is circular, square or rectangular shape with a flat, V- or U-form bottom or other combinations. In embodiments, the piston includes a toroid seal. For example, an O-ring is also commonly referred to as a "toroidal seal" or "toroid seal" indicative of the shape of the O-ring, which is a torus, or a doughnut-shaped ring. Toroidal seals are used in various applications for sealing fluid or gas, providing a barrier to prevent leakage between two surfaces. In embodiments, the diameter of the piston head is less than (e.g., 10%, 20%, or 30% less than) the diameter of the piston.

In embodiments, one or more pistons are affixed to a solid support to enable all pistons to plunge in concert. For example, a piston array includes a plurality of pistons. In embodiments, the piston array includes a plurality of pistons arranged in a pattern that complements the first pattern such that the plurality of pistons can be inserted into the plurality of receptacles. In embodiments, the piston array includes a base and a plurality of pistons extending from the base. In embodiments, the piston array includes 2, 4, 6, 12, 24, 48, 96, 384, or 1536 pistons. In embodiments, the piston array includes 12, 24, 48, or 96 pistons. In embodiments, the pattern within a piston array (and the corresponding receiving array) is useful for configuring, aligning, and generating reproducible samples. In embodiments, the pattern of the piston array is designed to complement a corresponding pattern in the receiving array. In embodiments, the receiving array permits punch devices to contact each other (e.g., be adjacent to each other) to minimize gaps. In embodiments, the piston array includes 2, 4, 6, 8, 10, 12, 14, 16, 18, 20, 22, 24, 26, 28, 30, 32, 34, 36, 38, 40, 42, 44, 46, or 48 pistons.

In embodiments, the diameter of the internal cavity of the punch device at the top end is greater than the diameter of the internal cavity at the bottom end. In embodiments, when the punch device is case of a cylindrical or frustoconical, the cross section may provide a useful metric for determining the size. In embodiments, the internal cavity may have a cross-section which is circular, triangular, square, rectangular, or a combination thereof. In embodiments, the cross section of the internal cavity at the top end is greater than the cross section of the internal cavity at the bottom end of the punch device. The cross-sectional area is simply the area of the circle (area=$pi \times r^2$, where r is the radius). In embodiments, when the cross-sectional area varies throughout the punch device and/or piston, e.g., having a frustoconical shape, the average cross-sectional area is an average of the cross-sectional areas. As a good approximation, the average cross-sectional area of a frustoconical-shaped device is the average of the circular cross-sections at each end. In embodiments, the internal diameter of the punch device is 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mm. In embodiments, the diameter of the internal cavity at the top end is about 4.5 mm to about 6.5 mm and the diameter of the internal cavity at the bottom end is about 5.0 mm to about 5.5 mm.

In embodiments, the piston is smaller than the punch device (i.e., the piston includes a diameter smaller than the diameter of the internal cavity). For example, the piston may fit inside the punch device to expel the tissue section.

In embodiments, the biological sample is a tissue section. In embodiments, the tissue section may be referred to herein as a biological sample. In embodiments, the thickness of the biological sample is about 1 $\mu$m to about 20 $\mu$m. In embodiments, the thickness of the biological sample is about 5 $\mu$m to about 12 $\mu$m. In embodiments, the thickness of the biological sample is about 8 $\mu$m to about 15 $\mu$m. In embodiments, the thickness of the biological sample is about 1 $\mu$m, about 2 $\mu$m, about 3 $\mu$m, about 4 $\mu$m, about 5 $\mu$m, about 6 $\mu$m, about 7 $\mu$m, about 8 $\mu$m, about 9 $\mu$m, about 10 $\mu$m, about 11 $\mu$m, about 12 $\mu$m, about 13 $\mu$m, about 14 $\mu$m, or about 15 $\mu$m. In embodiments, the thickness of the biological sample is about 1 $\mu$m. In embodiments, the thickness of the biological sample is about 2 $\mu$m. In embodiments, the thickness of the biological sample is about 3 $\mu$m. In embodiments, the thickness of the biological sample is about 4 $\mu$m. In embodiments, the thickness of the biological sample is about 5 $\mu$m. In embodiments, the thickness of the biological sample is about 6 $\mu$m. In embodiments, the thickness of the biological sample is about 7 $\mu$m. In embodiments, the thickness of the biological sample is about 8 $\mu$m. In embodiments, the thickness of the biological sample is about 9 $\mu$m. In embodiments, the thickness of the biological sample is about 10 $\mu$m. In embodiments, the thickness of the biological sample is about 11 $\mu$m. In embodiments, the thickness of the biological sample is about 12 $\mu$m. In embodiments, the thickness of the biological sample is about 13 $\mu$m. In embodiments, the thickness of the biological sample is about 14 $\mu$m. In embodiments, the thickness of the biological sample is about 15 $\mu$m. In embodiments, the thickness of the biological sample is less than about 10 $\mu$m. In embodiments, the thickness of the biological sample is less about 6 $\mu$m, 7 $\mu$m, 8 $\mu$m, 9 $\mu$m or 10 $\mu$m. In embodiments, the thickness of the biological sample ranges from 1 $\mu$m to 20 $\mu$m. In embodiments, the thickness of the biological sample ranges from 5 $\mu$m to 12 $\mu$m. In embodiments, the thickness of the biological sample ranges from 8 $\mu$m to 15 $\mu$m. In embodiments, the thickness of the biological sample is 1 $\mu$m, 2 $\mu$m, 3 $\mu$m, 4 $\mu$m, 5 $\mu$m, 6 $\mu$m, 7 $\mu$m, 8 $\mu$m, 9 $\mu$m, 10 $\mu$m, 11 $\mu$m, 12 $\mu$m, 13 $\mu$m, 14 $\mu$m, or 15 $\mu$m. In embodiments, the thickness of the biological sample is 1 $\mu$m. In embodiments, the thickness of the biological sample is 2 $\mu$m. In embodiments, the thickness of the biological sample is 3 $\mu$m. In embodiments, the thickness of the biological sample is 4 $\mu$m. In embodiments, the thickness of the biological sample is 5 $\mu$m. In embodiments, the thickness of the biological sample is 6 $\mu$m. In embodiments, the thickness of the biological sample is 7 $\mu$m. In embodiments, the thickness of the biological sample is 8 $\mu$m. In embodiments, the thickness of the biological sample is 9 $\mu$m. In embodiments, the thickness of the biological sample is 10 $\mu$m. In embodiments, the thickness of the biological sample is 11 $\mu$m. In embodiments, the thickness of the biological sample is 12 $\mu$m. In embodiments, the thickness of the biological sample is 13 $\mu$m. In embodiments, the thickness of the biological sample is 14 $\mu$m. In embodiments, the thickness of the biological sample is 15 $\mu$m. In embodiments, the thickness of the biological sample is less than 10 $\mu$m. In embodiments, the thickness of the biological sample is less than 6 $\mu$m, 7 $\mu$m, 8 $\mu$m, 9 $\mu$m, or 10 $\mu$m.

Tissue sections include tissue or organ samples obtained from a subject, e.g., a mammal. In certain embodiments, the subject is diagnosed with a disease or disorder, such as a cancerous tumor, or considered at risk of having or developing the disease or disorder. Tissue sections may also be obtained from healthy donors, e.g., as normal control samples. In certain embodiments, both a disease tissue (e.g., a tumor tissue) sample and a normal sample are obtained from the same subject. In embodiments, the tissue section is obtained from a patient, e.g., a mammal such as a human. In other embodiments, a tissue section is obtained from an animal model of disease. Various animal models of disease are known and available in the art. Particular animal models of cancer include but are not limited to xenograft, syngeneic, and PDx models. Patient-derived xenografts (PDX) are models of cancer where the tissue or cells from a patient's tumor are implanted into an immunodeficient or humanized mouse. Animal models may also include human cells, cancerous or otherwise, introduced into animal models wherein tumor properties, progress, and treatment may be assessed.

In embodiments, the tissue section includes a tissue or a cell. In embodiments, the tissue section includes a biomolecule (e.g., a biomolecule as described herein). Biological tissue samples suitable for use with the methods and systems described herein generally include any type of tissue samples collected from living or dead subjects, such as, for example, tumor tissue and autopsy samples. Tissue samples may be collected and processed using the methods and systems described herein and subjected to microscopic analysis immediately following processing, or may be preserved and subjected to microscopic analysis at a future time, e.g., after storage for an extended period of time. In some embodiments, the methods described herein may be used to preserve tissue samples in a stable, accessible and fully intact form for future analysis. For example, tissue samples, such as, e.g., human tumor tissue samples, may be processed as described herein and cleared to remove a plurality of cellular components, such as, e.g., lipids, and then stored for future analysis. In some embodiments, the methods and systems described herein may be used to analyze a fresh tissue section. In some embodiments, the methods and systems described herein may be used to analyze a previously-preserved (e.g., previously fixed) or stored tissue section (e.g., tissue sample). For example, in some embodiments a previously-preserved tissue sample that has not been subjected to a sample preparation process described herein may be processed and analyzed as described herein. In particular methods, a tissue sample is frozen prior to being processed as described herein.

In certain embodiments, tissue sections are tumor tissue samples. Tumor samples may contain only tumor cells, or they may contain both tumor cells and non-tumor cells. In particular embodiments, a tissue section includes only non-tumor cells. In particular embodiments, the tumor is a solid tumor. In particular embodiments, the tissue section is obtained from or includes an adrenal cortical cancer, anal cancer, aplastic anemia, bileduct cancer, bladder cancer, bone cancer, bone metastasis, brain tumor, brain cancer, breast cancer, childhood cancer, cancer of unknown primary origin, Castleman disease, cervical cancer, colon/rectal cancer, endometrial cancer, esophagus cancer, Ewing family of tumors, eye cancer, gallbladder cancer, gastrointestinal carcinoid tumors, gastrointestinal stromal tumors, gestational trophoblastic disease, head or neck cancer, Kaposi sarcoma, renal cell carcinoma, laryngeal and hypopharyngeal cancer, liver cancer, non-small cell lung cancer, small cell lung cancer, lung carcinoid tumor, lymphoma of the skin, malignant mesothelioma, myelodysplasia syndrome, nasal cavity or paranasal sinus cancer, nasopharyngeal cancer, neuroblastoma, oral cavity or oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma in adult soft tissue, basal or squamous cell skin cancer, melanoma, small intestine cancer, stomach cancer, testicular cancer, throat cancer, thymus cancer, thyroid cancer, uterine sarcoma, vaginal cancer, vulvar cancer, Waldenstrom macroglobulinemia, Wilms tumor and secondary cancers caused by cancer treatment, is a tissue section obtained from a subject diagnosed with or suspected of having any of these tumors or cancers. In embodiments, the tissue section is a breast tissue section. In embodiments, the tissue section is a lung tissue section. In embodiments, the tissue section is a colon tissue section. In embodiments, the tissue section is a kidney tissue section. In embodiments, the tissue section is a lymph node tissue section. In embodiments, the tissue section is a bone marrow tissue section.

Tissue sections may be obtained from a subject by any means known and available in the art. In particular embodiments, a tissue section, e.g., a tumor tissue sample, is obtained from a subject by fine needle aspiration, core needle biopsy, stereotactic core needle biopsy, vacuum-assisted core biopsy, or surgical biopsy. In particular embodiments, the surgical biopsy is an incisional biopsy, which removes only part of the suspicious area. In other embodiments, the surgical biopsy is an excisional biopsy, which removes the entire diseased tissue (e.g., tumor) or abnormal area. In particular embodiments, an excisional tumor tissue sample is obtained from a tumor that has been excised with the intent to "cure" a patient in the case of early stage disease, wherein in other embodiments, the excisional tumor tissue sample is obtained from an excised bulk of primary tumor in later stage disease. Tumor tissue samples may include primary tumor tissue, metastatic tumor tissue and/or secondary tumor tissue. Tumor tissue samples may be cell cultures, e.g., cultures of tumor-derived cell lines. In certain embodiments, a tissue section is a cell line, e.g., a cell pellet of a cultured cell line, such as a tumor cell line. In particular embodiments, the cell line or cell pellet is frozen or was previously frozen. Such cell lines and pellets are useful, e.g., as positive or negative controls for imaging with various reagents. Tumor tissue samples may also be xenograft tumors, e.g., tumors obtained from animals administered with tumor cells, e.g., a human tumor cell line. In certain embodiments, a first tumor tissue sample from a subject is a primary tumor tissue sample obtained during an initial surgery intended to remove the entire tumor, and a second tumor tissue sample is obtained from the same subject is a metastatic tumor tissue sample or a secondary tumor tissue sample obtained during a later surgery.

Tissue sections, e.g., tumor tissue samples, may be obtained surgically or using a laparoscope. A tissue section may be a tissue sample obtained from any part of the body to examine it for disease or injury, e.g., presence of cancer tissue or cells, or the extent or characteristics thereof. In particular embodiments, the tissue section includes abdominal tissue, bone, bone marrow, breast tissue, endometrial tissue, kidney tissue, liver tissue, lung or chest tissue, lymph node, nerve tissue, skin, testicular tissue, head or neck tissue, or thyroid tissue. In certain embodiments, the tissue is obtained from brain, breast, skin, bone, joint, skeletal muscle, smooth muscle, red bone marrow, thymus, lymphatic vessel, thoracic duct, spleen, lymph node, nasal cavity, pharynx, larynx, trachea, bronchus, lung, oral cavity, esophagus, liver, stomach, small intestine, large intestine, rectum, anus, spinal cord, nerve, pineal gland, pituitary gland, thyroid gland, thymus, adrenal gland, pancreas, ovary, testis, heart, blood vessel, kidney, uterus, urinary bladder, urethra, prostate gland, penis, prostate, testis, scrotum, ductus deferens, mammary glands, ovary, uterus, vagina, or uterine tube.

In particular embodiments, a tissue section has a size greater than sections typically examined by traditional pathology thin section or immunohistochemical analysis, which are typically in the range of 2-10 microns thick. In certain embodiments, a tissue section is greater than 20 microns, greater than 50 microns, greater than 100 microns, greater than 200 microns, greater than 500 microns, greater than 1 mm, greater than 2 mm, greater than 5 mm, greater than 10 mm or greater than 20 mm in thickness and/or length. In particular embodiments, the tissue section has a length and/or a thickness between 20 microns and 20 mm, between 20 microns and 10 mm, or between 50 microns and 1 mm. In certain embodiments, a tissue section is a cubic sample with each side greater than 10 microns, greater than 20 microns, greater than 50 microns, greater than 100 microns, greater than 200 microns, greater than 500 microns, greater than 1 mm, greater than 2 mm, greater than 5 mm, greater than 10 mm, or greater than 2 mm in thickness and/or length. In some embodiments, a tissue section is thinner, e.g., from about 4-10 or 4-20 microns in thickness. A micron is short for micrometer, one-millionth of a meter, or $1 \times 10^{-6}$ (denoted p) meters.

In embodiments, the tissue section forms part of a tissue in situ. In embodiments, the tissue section includes one or more prokaryotic cells. In embodiments, the tissue section includes one or more eukaryotic cells. In embodiments, the tissue section includes a bacterial cell (e.g., a bacterial cell or bacterial spore), a fungal cell (e.g., a fungal spore), a plant cell, or a mammalian cell. In embodiments, the tissue section includes a stem cell. In embodiments, the stem cell is an embryonic stem cell, a tissue-specific stem cell, a mesenchymal stem cell, or an induced pluripotent stem cell. In embodiments, the tissue section includes an endothelial cell, muscle cell, myocardial, smooth muscle cell, skeletal muscle cell, mesenchymal cell, epithelial cell; hematopoietic cell, such as lymphocytes, including T cell, e.g., (Th1 T cell, Th2 T cell, ThO T cell, cytotoxic T cell); B cell, pre-B cell; monocytes; dendritic cell; neutrophils; or a macrophage. In embodiments, the tissue section includes a stem cell, an immune cell, a cancer cell (e.g., a circulating tumor cell or cancer stem cell), a viral-host cell, or a cell that selectively binds to a desired target. In embodiments, the cell includes a T cell receptor gene sequence, a B cell receptor gene sequence, or an immunoglobulin gene sequence. In embodiments, the cell includes a Toll-like receptor (TLR) gene sequence. In embodiments, the cell includes a gene sequence corresponding to an immunoglobulin light chain polypeptide and a gene sequence corresponding to an immunoglobulin heavy chain polypeptide. In embodiments, the tissue section includes a genetically modified cell. In embodiments, the tissue section includes a circulating tumor cell or cancer stem cell.

In embodiments, the tissue section includes an adherent cell (e.g., epithelial cell, endothelial cell, or neural cell). Adherent cells are usually derived from tissues of organs and attach to a substrate (e.g., epithelial cells adhere to an extracellular matrix coated substrate via transmembrane adhesion protein complexes). Adherent cells typically require a substrate, e.g., tissue culture plastic, which may be coated with extracellular matrix (e.g., collagen and laminin) components to increase adhesion properties and provide other signals needed for growth and differentiation. In embodiments, the tissue section includes a neuronal cell, an endothelial cell, epithelial cell, germ cell, plasma cell, a muscle cell, peripheral blood mononuclear cell (PBMC), a myocardial cell, or a retina cell. In embodiments, the tissue section includes a suspension cell (e.g., a cell free-floating in the culture medium, such a lymphoblast or hepatocyte). In embodiments, the tissue section includes a glial cell (e.g., astrocyte, radial glia), pericyte, or stem cell (e.g., a neural stem cell). In embodiments, the tissue section includes a neuronal cell. In embodiments, the tissue section includes an endothelial cell. In embodiments, the tissue section includes an epithelial cell. In embodiments, the tissue section includes a germ cell. In embodiments, the tissue section includes a plasma cell. In embodiments, the tissue section includes a muscle cell. In embodiments, the tissue section includes a peripheral blood mononuclear cell (PBMC). In embodiments, the tissue section includes a myocardial cell. In embodiments, the tissue section includes a retina cell. In embodiments, the tissue section includes a lymphoblast. In embodiments, the tissue section includes a hepatocyte. In embodiments, the tissue section includes a glial cell. In embodiments, the tissue section includes an astrocyte. In embodiments, the tissue section includes a radial glia. In embodiments, the tissue section includes a pericyte. In embodiments, the tissue section includes a stem cell. In embodiments, the tissue section includes a neural stem cell.

In embodiments, the tissue section includes a cell bound to a known antigen. In embodiments, the cell is a cell that selectively binds to a desired target, wherein the target is an antibody, or antigen binding fragment, an aptamer, affimer, non-immunoglobulin scaffold, small molecule, or genetic modifying agent. In embodiments, the cell is a leukocyte (i.e., a white-blood cell). In embodiments, leukocyte is a granulocyte (neutrophil, eosinophil, or basophil), monocyte, or lymphocyte (T cells and B cells). In embodiments, the cell is a lymphocyte. In embodiments, the cell is a T cell, an NK cell, or a B cell.

In embodiments, the tissue section includes an immune cell. In embodiments, the immune cell is a granulocyte, a mast cell, a monocyte, a neutrophil, a dendritic cell, or a natural killer (NK) cell. In embodiments, the immune cell is an adaptive cell, such as a T cell, NK cell, or a B cell. In embodiments, the cell includes a T cell receptor gene sequence, a B cell receptor gene sequence, or an immunoglobulin gene sequence. In embodiments, the immune cell is a granulocyte. In embodiments, the immune cell is a mast cell. In embodiments, the immune cell is a monocyte. In embodiments, the immune cell is a neutrophil. In embodiments, the immune cell is a dendritic cell. In embodiments, the immune cell is a natural killer (NK) cell. In embodiments, the immune cell is a T cell. In embodiments, the immune cell is a B cell. In embodiments, the cell includes a T cell receptor gene sequence. In embodiments, the cell includes a B cell receptor gene sequence. In embodiments, the cell includes an immunoglobulin gene sequence. In embodiments, the plurality of target nucleic acids includes non-contiguous regions of a nucleic acid molecule. In embodiments, the non-contiguous regions include regions of a VDJ recombination of a B cell or T cell.

In embodiments, the tissue section includes a cancer cell. In embodiments, the cancer is lung cancer, colorectal cancer, skin cancer, colon cancer, pancreatic cancer, breast cancer, cervical cancer, lymphoma, leukemia, or a cancer associated with aberrant K-Ras, aberrant APC, aberrant Smad4, aberrant p53, or aberrant TGFβ. In embodiments, the cancer cell includes a ERBB2, KRAS, TP53, PIK3CA, or FGFR2 gene. In embodiments, the cancer cell includes a cancer-associated gene (e.g., an oncogene associated with kinases and genes involved in DNA repair) or a cancer-associated biomarker. A "biomarker" is a substance that is associated with a particular characteristic, such as a disease or condition. A change in the levels of a biomarker may correlate with the risk or progression of a disease or with the susceptibility of the disease to a given treatment. In embodiments, the cancer is Acute Myeloid Leukemia, Adrenocortical Carcinoma, Bladder Urothelial Carcinoma, Breast Ductal Carcinoma, Breast Lobular Carcinoma, Cervical Carcinoma, Cholangiocarcinoma, Colorectal Adenocarcinoma, Esophageal Carcinoma, Gastric Adenocarcinoma, Glioblastoma Multiforme, Head and Neck Squamous Cell Carcinoma, Hepatocellular Carcinoma, Kidney Chromophobe Carcinoma, Kidney Clear Cell Carcinoma, Kidney Papillary Cell Carcinoma, Lower Grade Glioma, Lung Adenocarcinoma, Lung Squamous Cell Carcinoma, Mesothelioma, Ovarian Serous Adenocarcinoma, Pancreatic Ductal Adenocarcinoma, Paraganglioma & Pheochromocytoma, Prostate Adenocarcinoma, Sarcoma, Skin Cutaneous Melanoma, Testicular Germ Cell Cancer, Thymoma, Thyroid Papillary Carcinoma, Uterine Carcinosarcoma, Uterine Corpus Endometrioid Carcinoma, or Uveal Melanoma. In embodiments, the cancer-associated gene is a nucleic acid sequence identified within The Cancer Genome Atlas Program, accessible at www.cancer.gov/tcga.

In embodiments, the tissue section is obtained from a subject (e.g., human or animal tissue). Once obtained, the tissue section is placed in an artificial environment in plastic or glass containers supported with specialized medium containing essential nutrients and growth factors to support proliferation. In embodiments, the tissue section is permeabilized and immobilized to a solid support surface. In embodiments, the tissue section is permeabilized and immobilized to an array (i.e., to discrete locations arranged in an array). In embodiments, the tissue section is immobilized to a solid support surface. In embodiments, the surface includes a patterned surface (e.g., suitable for immobilization of a plurality of cells in an ordered pattern. The discrete regions of the ordered pattern may have defined locations in a regular array, which may correspond to a rectilinear pattern, circular pattern, hexagonal pattern, or the like. These discrete regions are separated by interstitial regions. As used herein, the term "interstitial region" refers to an area in a substrate or on a surface that separates other areas of the substrate or surface. In embodiments, a plurality of cells are immobilized on a patterned surface that have a mean or median separation from one another of about 10-20 μm. In embodiments, a plurality of cells are immobilized on a patterned surface that have a mean or median separation from one another of about 10-20; 10-50; or 100 μm. In embodiments, a plurality of cells are arrayed on a substrate. In embodiments, a plurality of cells are immobilized in a 96-well microplate having a mean or median well-to-well spacing of about 8 mm to about 12 mm (e.g., about 9 mm). In embodiments, a plurality of cells are immobilized in a 384-well microplate having a mean or median well-to-well spacing of about 3 mm to about 6 mm (e.g., about 4.5 mm).

In embodiments, the tissue section is attached to the receiving substrate via a bioconjugate reactive linker. In embodiments, the tissue section is attached to the receiving substrate via one or more bioconjugate linker(s). The bioconjugate linker is the product of a reaction between the two bioconjugate group (e.g., click chemistry groups). In embodiments, the tissue section is attached to the substrate via a specific binding reagent. In embodiments, the specific binding reagent includes an antibody, single-chain Fv fragment (scFv), antibody fragment-antigen binding (Fab), or an aptamer. In embodiments, the specific binding reagent includes an antibody, or antigen binding fragment, an aptamer, affimer, or non-immunoglobulin scaffold. In embodiments, the specific binding reagent is a peptide, a cell penetrating peptide, an aptamer, a DNA aptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a polylysine, polyethyleneimine, diethylaminoethyl (DEAE)-dextran, cholesterol, or a sterol moiety. Substrates may be prepared for selective capture of particular cells of the tissue section. For example, a substrate containing a plurality of bioconjugate reactive moieties or a plurality of specific binding reagents, optionally in an ordered pattern, contacts a plurality of cells of the tissue section. Only cells of the tissue section containing complementary bioconjugate reactive moieties or complementary specific binding reagents are capable of reacting, and thus adhering, to the substrate.

In embodiments, the receiving substrate includes a coating for enhanced biomolecule adhesion. Coatings for enhanced biomolecule adhesion are known, for example extracellular matrix proteins such as collagen type I, fibronectin, and laminin mediate specific binding of the cell to the protein. Poly-D-Lysine (PDL), a synthetically produced biomolecule, belongs to the non-specific adhesion-promoting polypeptides. PDL is typically used to promote cell adhesion, especially during washing steps, as well as to enhance cell vitality and proliferation during serum-reduced or serum-free cultivation.

In embodiments, the tissue section is exposed to paraformaldehyde (i.e., by contacting the cell with paraformaldehyde). Any suitable permeabilization and fixation technologies can be used for making the cell available for the detection methods provided herein. In embodiments the method includes affixing single cells or tissues to a transparent substrate. Exemplary tissue include those from skin tissue, muscle tissue, bone tissue, organ tissue and the like. In embodiments, the method includes immobilizing the tissue section in situ to a substrate and permeabilized for delivering probes, enzymes, nucleotides and other components required in the reactions. In embodiments, the tissue section includes many cells from a tissue section in which the original spatial relationships of the cells are retained. In embodiments, the tissue section in situ is within a Formalin-Fixed Paraffin-Embedded (FFPE) sample. In embodiments, the tissue section is subjected to paraffin removal methods, such as methods involving incubation with a hydrocarbon solvent, such as xylene or hexane, followed by two or more washes with decreasing concentrations of an alcohol, such as ethanol. The tissue section may be rehydrated in a buffer, such as PBS, TBS or MOPs. In embodiments, the FFPE sample is incubated with xylene and washed using ethanol to remove the embedding wax, followed by treatment with Proteinase K to permeabilized the tissue. In embodiments, the tissue section is fixed with a chemical fixing agent. In embodiments, the chemical fixing agent is formaldehyde or glutaraldehyde. In embodiments, the chemical fixing agent is glyoxal or dioxolane. In embodiments, the chemical fixing agent includes one or more of ethanol, methanol, 2-propanol, acetone, and glyoxal. In embodiments, the chemical fixing agent includes formalin, Greenfix®, Greenfix® Plus, UPM, CyMol®, HOPE®, CytoSkelFix™, F-Solv©, FineFIX®, RCL2/KINFix, UMFIX, Glyo-Fixx®, Histochoice®, or PAXgene®. In embodiments, the tissue section is fixed within a synthetic three-dimensional matrix (e.g., polymeric material). In embodiments, the synthetic matrix includes polymeric-crosslinking material. In embodiments, the material includes polyacrylamide, poly-ethylene glycol (PEG), poly(acrylate-co-acrylic acid) (PAA), or Poly(N-isopropylacrylamide) (NIPAM).

In embodiments, the fixed tissue may be frozen tissue. The frozen biological tissue can be fixed using a fixing agent, which is suitably an organic fixing agent. In some embodiments, the fixing agent can be chilled and can be at a temperature of about 0° C. to about 100° C., suitably about zero to about 50° C., or about 1° C. to about 50° C. The fixing agent can be chilled by placing it over a bed of ice to maintain its temperature as close to 0° C. as possible. The frozen biological tissue can be treated with the fixing agent using any suitable technique, suitably by immersing it in the fixing agent for a period of time. Depending on the type and size of the biological tissue sample, the treatment time can range from about 5 minutes to about 60 minutes, suitably about 10 minutes to about 30 minutes, or about 15 minutes to about 25 minutes, or about 20 minutes. In some embodiments, treatment time may be overnight. During fixing, the snap-frozen tissue will thaw but will suitably remain at a low temperature due to the low temperature environment of the fixing agent.

In embodiments, the biological sample is embedded in an embedding material including paraffin wax, polyepoxide polymer, polyacrylic polymer, agar, gelatin, celloidin, cryogel, optimal cutting temperature (OCT) compositions, glycols, or a combination thereof. In embodiments, the tissue section is embedded in an embedding material including paraffin wax. In embodiments, the OCT composition includes about 10% polyvinyl alcohol and about 4% polyethylene glycol. In embodiments, the OCT composition includes sucrose (e.g., 30% sucrose). In embodiments, the OCT composition is Tissue Freezing Medium (TFM) available from Leica Microsystems, Catalog #14020108926.

In embodiments, the tissue section is an artificial tissue section, wherein the artificial tissue section includes one or more cells suspended in a hydrogel. In embodiments, the artificial tissue section includes one or more cells suspended in a hydrogel that is embedded in an optimal cutting temperature (OCT) composition. In embodiments, the artificial tissue section is prepared according to the following method: the sample containing the biomolecule of interest (e.g., a cell or a particle) is embedded in a crosslinked hydrogel (e.g., a polymer composition including 3 to 20% acrylamide and N,N-dimethylacrylamide). Any suitable hydrogel may be used, for example a hydrogel including poly(2-hydroxyethyl methacrylate) (PHEMA), optionally crosslinked with poly-ethylene glycol dimethacrylate; 2-hydroxyethyl methacrylate (HEMA) optionally crosslinked with TEGDMA (triethylene glycol dimethacrylate); polyethylene glycol methacrylate (PEGMA), optionally crosslinked with TEGDMA (triethylene glycol dimethacrylate); a copolymer of methacrylic acid (MAA) and polyethylene glycol methacrylate (PEGMA), optionally crosslinked with tetra(ethylene glycol) dimethacrylate; or poly(N-isopropyl acrylamide) (PNIPAM), optionally crosslinked with N,N-methylene bisacrylamide. Additional hydrogels include a polymer such as poly(hydroxyethyl methacrylate) (PHEMA), poly(glyc-eryl methacrylate) (PGMA), poly(hydroxypropyl methacry-late) (PHPMA), polyacrylamide (PAM), polymethacrylam-ide (PMAM), polyvinyl alcohol (PVA), polyacrylic acid (PAA), polyvinyl pyrrolidone (PVP), poly(ε-caprolactone) (PCL), poly(ethyleneimine) (PEI), poly(N,N-dimethylacry-lamide) (PDMAM), poly(2-methoxyethyl acrylate) (PMEA), or a copolymer thereof. Polymer chains in a hydrogel may be crosslinked with each other chemically via covalent bonds or physically via non-covalent interactions to produce the network structure. The physical cross-linking involves hydrogen bonding, hydrophobic interactions, crys-tallinity, and ionic interactions. In chemically cross-linked hydrogels, covalent bonds cross-link individual polymer chains. Any suitable crosslinker may be used, for example N,N-methylene bisacrylamide, N,N-ethylene bisacrylamide, 1,4-Bis(acryloyl)piperazine, triethylene glycol dimethacry-late (TEGDMA), 1,1,1-trimethylolpropane trimethacrylate (TMPTMA), poly(ethylene glycol) dimethacrylate (PEGDMA), glyoxal, or tetramethylethylenediamineor N,N'-Bis(acryloyl)cystamine. Following hydrogel embed-ding, the sample may be frozen in OCT at –80° C. The frozen OCT-hydrogel complex may then be sectioned (e.g., tissue sections of 5 μm and 9 μm thickness were derived). It is known that OCT compounds may impact PCR amplifi-cation, see for example Turbett and Sellner (Diagn Mol Pathol. 1997 October; 6(5):298-303), so embedding the biological sample in a hydrogel first helps protect the sample from downstream effects from the OCT.

In embodiments, the biological sample is embedded in an embedding material including a polyepoxide polymer. In embodiments, the biological sample is embedded in an embedding material including polyacrylic polymer. In embodiments, the biological sample is embedded in an embedding material including agar. In embodiments, the biological sample is embedded in an embedding material including gelatin. In embodiments, the biological sample is embedded in an embedding material including celloidin. In embodiments, the biological sample is embedded in an embedding material including a cryogel. In embodiments, the biological sample is embedded in an embedding material including an optimal cutting temperature (OCT) composi-tions. In embodiments, the biological sample is embedded in an embedding material including one or more glycols.

In embodiments, the biological sample is attached to (e.g., mounted on) a carrier substrate forming the sample-carrier construct. In embodiments, the carrier substrate includes agarose, amylose, amylopectin, alginate, gelatin, cellulose, polyolefin, polyethylene glycol, polyvinyl alcohol, and/or acrylate polymers and copolymers thereof.

In embodiments, the carrier substrate includes a hydrogel. In embodiments, the carrier substrate includes agarose, amylose, amylopectin, alginate, gelatin, cellulose, poly-olefin, polyethylene glycol, polyvinyl alcohol, and/or acry-late polymers and copolymers thereof. In embodiments, the carrier substrate includes agarose, amylose, or amylopectin. In embodiments, the carrier substrate includes agarose. In embodiments, the carrier substrate includes amylose. In embodiments, the carrier substrate includes amylopectin. In embodiments, the carrier substrate includes alginate. In embodiments, the carrier substrate includes gelatin. In embodiments, the carrier substrate includes cellulose. In embodiments, the carrier substrate includes polyolefin. In embodiments, the carrier substrate includes polyethylene glycol. In embodiments, the carrier substrate includes poly-vinyl alcohol. In embodiments, the carrier substrate includes acrylate polymers and copolymers thereof. In embodiments, the carrier substrate includes agarose, agar, amylopectin, polyvinyl alcohol, Gellan gum, or alginate.

In embodiments, the carrier substrate includes about 2% to about 10% agarose. In embodiments, the carrier substrate includes about 2% agarose. In embodiments, the carrier substrate includes about 3% agarose. In embodiments, the carrier substrate includes about 4% agarose. In embodi-ments, the carrier substrate includes about 5% agarose. In embodiments, the carrier substrate includes about 6% aga-rose. In embodiments, the carrier substrate includes about 7% agarose. In embodiments, the carrier substrate includes about 8% agarose. In embodiments, the carrier substrate includes about 9% agarose. In embodiments, the carrier substrate includes about 10% agarose.

In embodiments, the carrier substrate further includes a support scaffold. For example, the carrier substrate (i.e., the material in contact with the biological sample) may include a glass, plastic, or other material (e.g., cellulose) support scaffold. The support scaffold facilitates transfer by provid-ing additional rigidity to the carrier substrate and may reduce deformation of the carrier substrate during sample capture and/or transfer. In embodiments, the support scaffold is glass. In embodiments, the support scaffold is polydim-ethylsiloxane (PDMS).

In embodiments, the carrier substrate includes a hydrogel. In embodiments, the hydrogel carrier substrate includes agarose, alginate, gelatin, cellulose, polyolefin, polyethylene glycol, polyvinyl alcohol, and/or acrylate polymers and copolymers. In embodiments, the hydrogel carrier substrate includes agarose, amylose, or amylopectin. In embodiments, the hydrogel carrier substrate includes acrylamide, meth-acrylate and methacrylamide polymers and copolymers thereof. Any suitable hydrogel may be used as a carrier substrate, for example a hydrogel including poly(2-hydroxy-ethyl methacrylate) (PHEMA), optionally crosslinked with polyethylene glycol dimethacrylate; 2-hydroxyethyl meth-acrylate (HEMA) optionally crosslinked with TEGDMA (triethylene glycol dimethacrylate); polyethylene glycol methacrylate (PEGMA), optionally crosslinked with TEGDMA (triethylene glycol dimethacrylate); a copolymer of methacrylic acid (MAA) and polyethylene glycol meth-acrylate (PEGMA), optionally crosslinked with tetra(ethyl-ene glycol) dimethacrylate; or poly(N-isopropyl acrylamide) (PNIPAM), optionally crosslinked with N,N-methylene bisacrylamide. Additional hydrogels include a polymer such as poly(hydroxyethyl methacrylate) (PHEMA), poly(glyc-eryl methacrylate) (PGMA), poly(hydroxypropyl methacry-late) (PHPMA), polyacrylamide (PAM), polymethacrylam-ide (PMAM), polyvinyl alcohol (PVA), polyacrylic acid (PAA), polyvinyl pyrrolidone (PVP), poly(ε-caprolactone) (PCL), poly(ethyleneimine) (PEI), poly(N,N-dimethylacry-lamide) (PDMAM), poly(2-methoxyethyl acrylate) (PMEA), or a copolymer thereof. Polymer chains in a hydrogel may be crosslinked with each other chemically via covalent bonds or physically via non-covalent interactions to produce the network structure. The physical cross-linking involves hydrogen bonding, hydrophobic interactions, crys-tallinity, and ionic interactions. In chemically cross-linked hydrogels, covalent bonds cross-link individual polymer chains. Any suitable crosslinker may be used, for example N,N-methylene bisacrylamide, N,N-ethylene bisacrylamide, 1,4-Bis(acryloyl)piperazine, triethylene glycol dimethacry-late (TEGDMA), 1,1,1-trimethylolpropane trimethacrylate (TMPTMA), poly(ethylene glycol) dimethacrylate (PEGDMA), glyoxal, or tetramethylethylenediamineor N,N'-Bis(acryloyl)cystamine.

In embodiments, the carrier substrate and/or the receiving substrate is sterile prior to immobilizing the tissue section onto the carrier substrate. In embodiments, the hydrogel carrier substrate is sterile prior to immobilizing the tissue section onto the carrier substrate. In embodiments, the carrier substrate is sterilized prior to contact with the tissue section. In embodiments, the receiving substrate is sterilized prior to contact with the tissue section. In embodiments, the hydrogel carrier substrate is sterilized prior to contact with the tissue section Methods of sterilization include, but are not limited to, steam autoclaving (e.g., sterilization in an autoclave under a standard condition at 121° C. for 30 min), ethanol sterilization, and gamma irradiation, as described further in Han X. Biointerphases. 2017; 12(2): 02C411 and Galante R et al., J. Biomed. Mater. Res. B Appl. Biomater. 2018; 106(6): 2472-2492, each of which is incorporated herein by reference.

In embodiments, the carrier substrate includes a semi-solid foam. In embodiments, the carrier substrate includes a polythioketal-based polyurethane (PTK-UR) foam scaffold. In embodiments, the carrier substrate includes hydroxypropyl methylcellulose (HPMC) and polyvinylpyrrolidone (PVP). In embodiments, the carrier substrate includes dry ice (i.e., solid carbon dioxide). In embodiments, the carrier substrate includes ice (i.e., frozen water).

In embodiments, the hydrogel carrier substrate includes an agarose gel. Agarose gels can be made at different weight percentages by varying the amount of purified agarose in solution prior to gelation, which alters the microstructure and subsequent bulk mechanical behavior significantly. Agarose gels are typically categorized by their weight percentages, meaning that a 1% agarose gel is defined by 1 g of agarose powder (agar) per 100 mL of buffer solution. The type of buffer solution used to make agarose is generally a TBE buffer, which is a tris base, boric acid, and EDTA (ethylene diamine tetraacetic acid) mixture produced at various concentrations in water. In embodiments, the hydrogel carrier substrate includes less than about 5% agarose. In embodiments, the hydrogel carrier substrate includes less than about 4% agarose. In embodiments, the hydrogel carrier substrate includes less than about 3% agarose. In embodiments, the hydrogel carrier substrate includes less than about 2% agarose. In embodiments, the hydrogel carrier substrate includes more than about 5% agarose.

In embodiments, the hydrogel carrier substrate is contacted with glycerol (e.g., a 50-80% solution of glycerol. Without wishing to be bound by any theory, it is hypothesized that saturating hydrogel carrier substrate with glycerol reduced damage to frozen tissue samples, possibly by changing the surface tension or hydrophobicity. In embodiments, the hydrogel carrier substrate is stored in a glycerol solution prior to use.

In embodiments, the hydrogel carrier substrate further includes a support scaffold (e.g., the hydrogel carrier substrate forms part of a multi-layer substrate). In embodiments, the support scaffold is forms a rigid backing for the hydrogel carrier substrate. In embodiments, the support scaffold includes a thermoplastic elastomer. In embodiments, the support scaffold includes a polyester. In embodiments, the support scaffold includes polyethylene terephthalate. In embodiments, the support scaffold includes biaxially-oriented polyethylene terephthalate. In embodiments, the support scaffold is non-porous. In embodiments, the support scaffold is solid.

When considering a carrier substrate as a two-dimensional body, i.e., neglecting its thickness, the mechanical properties in the absence of anisotropies can be character-ized by one or more elastic constants according to continuum elasticity theory. One such elastic constant is the Young's modulus (alternatively referred to as an elastic modulus). In principle, the Young's modulus of a carrier substrate can be measured by finding a relationship between a force applied to the carrier substrate and the resultant deformation. On a macroscale, the Young's modulus is usually obtained by measuring the stress-strain curves of a substrate specimen through the compression method or the tensile method and then finding the slope of the curve.

In embodiments, the carrier substrate includes a Young's modulus of about 5 kPa to about 30 kPa. In embodiments, the carrier substrate includes a Young's modulus of about 5 kPa to about 20 kPa. In embodiments, the carrier substrate includes a Young's modulus of about 5 kPa to about 15 kPa. In embodiments, the carrier substrate includes a Young's modulus of about 5 kPa, about 10 kPa, about 15 kPa, about 20 kPa, about 25 kPa, or about 30 kPa. In embodiments, the carrier substrate includes a Young's modulus of about 5 kPa. In embodiments, the carrier substrate includes a Young's modulus of about 10 kPa. In embodiments, the carrier substrate includes a Young's modulus of about 15 kPa. In embodiments, the carrier substrate includes a Young's modulus of about 20 kPa. In embodiments, the carrier substrate includes a Young's modulus of about 25 kPa. In embodiments, the carrier substrate includes a Young's modulus of about 30 kPa. In embodiments, the Young's modulus is quantified according to known techniques in the art (e.g., the indentation test). For example, the indentation test employs the use of an indenter which comes in to contact with and applies a perpendicular force on a small area of the carrier substrate. Alternatively, the Young's Modulus of thin elastic membranes of materials can be determined using Diaphragm tests, where the membrane is clamped at two ends and inflated in the form of a dome while the pressure of suction is controlled by a pressure controller.

In embodiments, the compression modulus is about 38+/−2 kPa (e.g., 1% agarose), about 254+/−20 kPa (e.g., 2% agarose), about 929+/−48 kPa (e.g., 5% agarose), or about 2580+/−225 kPa (e.g., 10% agarose). In embodiments, the carrier substrate includes interfacial water, wherein the interfacial water is on the surface, such that the interfacial water is between the carrier substrate and the tissue section when forming a sample-carrier construct.

In embodiments, the carrier substrate includes about 80% to about 99% water. In embodiments, the carrier substrate includes about 80% to about 95% water. In embodiments, the carrier substrate includes about 80% to about 90% water. In embodiments, the carrier substrate includes about 80% to about 85% water. In embodiments, the carrier substrate includes about 80%, about 85%, about 90%, about 91%, about 92%, about 93%, about 94%, about 95%, about 96%, about 97%, about 98%, or about 99% water. In embodiments, the carrier substrate includes about 80% water. In embodiments, the carrier substrate includes about 85% water. In embodiments, the carrier substrate includes about 90% water. In embodiments, the carrier substrate includes about 91% water. In embodiments, the carrier substrate includes about 92% water. In embodiments, the carrier substrate includes about 93% water. In embodiments, the carrier substrate includes about 94% water. In embodiments, the carrier substrate includes about 95% water. In embodiments, the carrier substrate includes about 96% water. In embodiments, the carrier substrate includes about 97% water. In embodiments, the carrier substrate includes about 98% water. In embodiments, the carrier substrate includes about 99% water.

In embodiments, the hydrogel carrier substrate includes a Young's modulus of about 5 kPa to about 30 kPa. In embodiments, the hydrogel carrier substrate includes a Young's modulus of about 5 kPa to about 20 kPa. In embodiments, the hydrogel carrier substrate includes a Young's modulus of about 5 kPa to about 15 kPa. In embodiments, the hydrogel carrier substrate includes a Young's modulus of about 5 kPa, about 10 kPa, about 15 kPa, about 20 kPa, about 25 kPa, or about 30 kPa. In embodiments, the hydrogel carrier substrate includes a Young's modulus of about 5 kPa. In embodiments, the hydrogel carrier substrate includes a Young's modulus of about 10 kPa. In embodiments, the hydrogel carrier substrate includes a Young's modulus of about 15 kPa. In embodiments, the hydrogel carrier substrate includes a Young's modulus of about 20 kPa. In embodiments, the hydrogel carrier substrate includes a Young's modulus of about 25 kPa. In embodiments, the hydrogel carrier substrate includes a Young's modulus of about 30 kPa. In embodiments, the Young's modulus is quantified according to known techniques in the art (e.g., the indentation test). For example, the indentation test employs the use of an indenter which comes in to contact with and applies a perpendicular force on a small area of the carrier substrate. Alternatively, the Young's Modulus of thin elastic membranes of materials can be determined using Diaphragm tests, where the membrane is clamped at two ends and inflated in the form of a dome while the pressure of suction is controlled by a pressure controller.

In embodiments, the sample-carrier construct includes interfacial water, wherein the interfacial water is between the carrier substrate and the tissue section. In embodiments, the sample-carrier construct includes interfacial water, wherein the interfacial water is between the hydrogel carrier substrate and the tissue section.

In embodiments, the hydrogel carrier substrate includes interfacial water, wherein the interfacial water is on the surface, such that the interfacial water is between the carrier substrate and the tissue section when forming a sample-carrier construct.

In embodiments, the hydrogel carrier substrate includes about 80% to about 99% water. In embodiments, the hydrogel carrier substrate includes about 80% to about 95% water. In embodiments, the hydrogel carrier substrate includes about 80% to about 90% water. In embodiments, the hydrogel carrier substrate includes about 80% to about 85% water. In embodiments, the hydrogel carrier substrate includes about 80%, about 85%, about 90%, about 91%, about 92%, about 93%, about 94%, about 95%, about 96%, about 97%, about 98%, or about 99% water. In embodiments, the hydrogel carrier substrate includes about 80% water. In embodiments, the hydrogel carrier substrate includes about 85% water. In embodiments, the hydrogel carrier substrate includes about 90% water. In embodiments, the hydrogel carrier substrate includes about 91% water. In embodiments, the hydrogel carrier substrate includes about 92% water. In embodiments, the hydrogel carrier substrate includes about 93% water. In embodiments, the hydrogel carrier substrate includes about 94% water. In embodiments, the hydrogel carrier substrate includes about 95% water. In embodiments, the hydrogel carrier substrate includes about 96% water. In embodiments, the hydrogel carrier substrate includes about 97% water. In embodiments, the hydrogel carrier substrate includes about 98% water. In embodiments, the hydrogel carrier substrate includes about 99% water.

In an aspect is provided a kit. In embodiments, the kit includes a punch device configured to form a sample portion of the biological sample, the punch device forming an internal cavity and having a bottom edge sufficiently sharp to cut through the biological sample; and a piston sized and shaped to fit within the internal cavity of the punch device, wherein the piston inserts into the internal cavity of the punch device to expel the sample portion from the punch device. In embodiments, the kit includes any of the systems described herein.

The present disclosure provides kits for carrying out the methods of the present disclosure. The kits may include one or more of the following: fixative; carrier substrate (e.g., agarose, amylose, amylopectin, alginate, gelatin, cellulose, polyolefin, polyethylene glycol, polyvinyl alcohol, and/or acrylate polymers and copolymers); a surface including a plurality of wells separated from each other by interstitial regions on the surface, clearing reagents; nucleic acid probes, in situ hybridization buffer, labeled and/or unlabeled antibodies, buffers, e.g. buffer for fixing, washing, clearing, and/or staining specimens; mounting medium; embedding molds; dissection tools; etc. The subject reagents and kits thereof may vary greatly and may include a sub-set of the foregoing reagents. In embodiments, the kits include specialized well-plates, and reagents for sample preparation.

In embodiments, the kit includes a glass solid support. In embodiments, the kit includes (i) one or more cutting devices (e.g., a cutting device depicted in FIG. 9C), a piston (e.g., a piston in a piston array), and a receiving array. In embodiments, the receiving array is a solid support including a plurality of openings. The receiving array may be removable coupled to a glass solid support. Following tissue deposition, the glass solid support may be used to form a flow cell (e.g., by affixing a second solid support to the glass solid support, thereby forming one or more reaction chambers which may be used in a microfluidic device). In embodiments, the kit includes a plurality of punch devices. In embodiments, the kit includes a piston array. In embodiments, the receiving array includes one or more components or mechanisms for securing the piston array to the receiving array. Non-limiting examples means for securing the receiving array and the piston array include screws, clamps (e.g., C-clamps, bar clamps, and spring clamps), bolts and nuts, rivets, magnetic holders, Velcro straps, zip ties, adhesive tapes, suction cups, and toggle bolts. In embodiments, the receiving array and the piston array may include one or more pre-drilled holes or indentations to facilitate mating and alignment. In embodiments, the receiving array and/or the piston array may include features or marks to aid in alignment. For example, features may include the use of beveled/chamfered corners (e.g., a beveled corner prevents incorrect orientation by providing a unique, non-symmetrical edge), color coding, notches or grooves, alignment pins and holes, laser etching or marking, magnetic alignment, keyed slots, puzzle fit design, RFID tags or NFC, and optical markings.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, digital storage medium, etc., on which the information has been recorded. Yet another means that may be present is a website address which may be used via the Internet to access the information at a removed site. Any convenient means may be present in the kits.

In an aspect is provided a composition including an alcohol (e.g., polyvinyl alcohol), a glycol (e.g., polyethylene glycol), and a hydrogel, wherein the hydrogel includes a cell. In embodiments the hydrogel includes a plurality of cells, which may serve as a control specimen. In embodiments, the composition is stored at or below 0° C. (i.e., the composition is frozen and solid). In embodiments, the composition is stored at or about 0° C., −10° C., −20° C., 40° C., −60° C., −70° C., or −80° C. In embodiments, the composition is formed by mixing a cell and a hydrogel together to form an embedded cell, followed by contacting the embedded cell with an aqueous solution including the alcohol and the glycol (e.g., 10% polyvinyl alcohol and about 4% polyethylene glycol). In embodiments, the composition further includes sucrose (e.g., 30% sucrose). In embodiments, the alcohol and glycol are an optimal cutting temperature (OCT) reagent (e.g., Tissue Freezing Medium (TFM) available from Leica Microsystems, Catalog #14020108926). An OCT reagent are characterized as being generally non-reactive with biological materials and having a high degree of viscosity due to the presence of viscosity generating substances such as polyvinyl alcohol and polyethylene glycol (see, e.g., O.C.T. sold by Tissue Tek® (product code 4583) which is composed of 10.24% polyvinyl alcohol, 4.26% polyethylene glycol and 85.50% non-reactive ingredients). The OCT compounds function to rapidly freeze biological samples and typically include viscosity agents such as about 5% to about 20% polyvinyl alcohol and/or about 1% to about 10% polyethylene glycol.

The term "kit" includes both fragmented and combined kits. In embodiments, the kit includes, without limitation, nucleic acid primers, probes, adapters, enzymes, and the like, and are each packaged in a container, such as, without limitation, a vial, tube or bottle, in a package suitable for commercial distribution, such as, without limitation, a box, a sealed pouch, a blister pack and a carton. The package typically contains a label or packaging insert indicating the uses of the packaged materials. As used herein, "packaging materials" includes any article used in the packaging for distribution of reagents in a kit, including without limitation containers, vials, tubes, bottles, pouches, blister packaging, labels, tags, instruction sheets and package inserts.

In embodiments, the kit includes a receiving substrate (e.g., a receiving substrate as described herein). For example, the receiving substrate is a microplate. In embodiments, the receiving substrate includes a plurality of wells, wherein one or more wells include a functionalized glass surface or a functionalized plastic surface. In embodiments, the receiving substrate includes a container suitable for air- and moisture-sensitive components (e.g., the receiving substrate is packaged under nitrogen or argon). In embodiments, the kit includes a carrier substrate (e.g., a hydrogel carrier substrate) as described herein. In embodiments, the kit includes a cutting device (e.g., a punch device as described herein). In embodiments, the cutting device includes a circular hollow blade attached to a handle ranging, wherein the diameter of the circular hollow blade is about 0.5 mm to about 10 mm. In embodiments, the cutting device is disposable. In embodiments, the cutting device is reusable. In embodiments, the cutting device includes a plunger to aid in ejection of the cut section. In embodiments, the kit includes one or more detection agents (e.g., a detection agent as described herein, for example a fluorescent oligonucleotide probe and/or sequencing reagents).

In embodiments, the kit can further include one or more biological stain(s) (e.g., any of the biological stains as described herein). For example, the kit can further include eosin and hematoxylin. In other examples, the kit can include a biological stain such as acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, or any combination thereof.

In an aspect is provided a receiving array (e.g., a receiving array as described herein, for example as illustrated in FIG. 5A). In embodiments, the receiving array includes a plurality of receptacles arranged in a pattern, wherein each receptacle is configured to retain or receive a punch device; a plurality of punch devices, wherein each punch device comprises an internal cavity comprising a biological sample (e.g., a portion of a tissue) and a carrier substrate (e.g., a carrier substrate as described herein). In embodiments, the receiving array includes a glass solid support removable attached to the receiving array. In embodiments, the receiving array includes 2, 4, 6, 8, 10, 12, 14, 16, 18, 20, 22, or 22 receptacles.

In embodiments, the receptacle and punch device are configured to provide haptic feedback when the punch device is retained in the receptacle. Haptics often refer to those things that relate to the sense of touch. More specifically, haptics may refer to interfaces that provide force and/or tactile sensations, such as a vibration motor. The feedback may for example be in the form of a physical sensation that can be felt by the user when the user properly engages the punch device in the receiving array. In embodiments, the receiving array includes one or more actuators (e.g., a piezo-electric actuator) coupled to the receiving array. In some embodiments, the haptic feedback component can be a vibrating haptic actuator. For example, the vibrating haptic actuator can comprise an eccentric rotating mass (ERM) motor. In particular, the vibrating haptic actuator can be in a cylindrical form factor or can be in a coin form factor. In another non-limiting example, the vibrating haptic actuator can comprise a linear resonant actuator (LRA).

In embodiments, the punch device is retained in the receptacle using a snap-fit coupling between the punch device and the receptacle. A snap-fit assembly is a widely employed method in various industries for joining two parts together, eliminating the need for additional fastening elements such as screws, bolts, or adhesives. The fundamental concept of a snap-fit coupling relies on a designed protrusion on one part, known as the male component, and a corresponding cavity or undercut on the other, referred to as the female component. During assembly, when these two parts are pressed together, the protrusion flexes slightly until it surpasses the undercut or cavity, at which point it snaps back into its initial shape, thereby securing the connection between the parts. This mechanism allows for a quick and efficient joint, often requiring no tools for assembly.

There are various designs of snap-fits, each serving different purposes. Cantilever snap-fits, one of the most common types, utilize a beam that is anchored at one end and free at the other, snapping into a slot or recess on the mating part. Annular snap-fits, often used in circular applications like bottle lids, feature a series of flexible tabs around a circle that engage with a corresponding groove. Torsional snap-fits, rely on a twisting motion to lock the parts in place.

In embodiments, the receiving array includes an identifying feature at each receptacle, wherein the identifying feature uniquely identifies the receptacle. In embodiments, the piston array includes an identifying feature at each piston, wherein the identifying feature uniquely identifies the piston. For example, the identification feature may be an alphanumeric code or symbol. Alphanumeric codes or symbols are assigned to each item (e.g., a piston or a receptacle) and correspond to their specific location in the configuration. For instance, in a piston array or receiving array system with multiple identical-looking punch devices, each receptacle might be labeled with a unique alphanumeric code. This code not only identifies the punch device but also indicates its precise location within the array, thereby facilitating easy tracking and retrieval. In embodiments, the identifying feature utilizes color-coding as an indexing feature. Different colors are used to mark identical items, with each color corresponding to a specific position or category within the overall configuration. In addition, physical notches or shapes can serve as indexing features. Items may have small, physically distinct features like notches, grooves, or protrusions that correspond to matching features in their designated location.

In an aspect is provided a punch tool. See, for example, FIG. 11 and FIG. 12 for a non-limiting example of a punch tool. In embodiments, the punch tool includes a punch body. In embodiments, the punch tool includes a movable push button on the punch tool body. In embodiments, the punch tool is configured to be coupled to the punch device. In embodiments, the punch tool is a spring-loaded tool including a movable button configured to actuate the punch tool to expel, eject, or otherwise transition the punch device. In embodiments, the punch tool includes an outer housing that extends along a long axis. In embodiments, the punch tool includes a docking region that removably receives the punch device. In an embodiment, the punch device is aligned with the long axis when docked in the punch tool to permit a user to grasp the punch tool and ergonomically manipulate the position and orientation of the punch device such as in the manner of grasping a pen. The punch tool may retain and subsequently eject the punch device. The ejection process sequence is similar to the attachment or tip pickup securing process sequence except in reverse. For example, a distal O-ring axial force component of a compressed distal O-ring that provides a force to help remove the punch device during the ejection process.

In embodiments, the punch tool includes a drive device has a manual and/or an electric drive device (with electric motor, for instance). In particular, the handheld punch tool apparatus can be executed as a solely manually driven device or as a solely electrically driven device or as a device with a combined manual and electric drive device, the latter case in particular when there is a manual, servo-assisted drive.

III. Methods

In an aspect is disclosed methods for manipulating one or more biological samples. With reference to the flow diagram of FIG. 3, a sample portion 106 is obtained using a punch device 101 as described above with reference to FIGS. 4A and 4B. Each loaded punch device 101 (or an array of punch devices loaded with a sample that has been cut) is loaded into a respective receptacle 202 of the receiving array 200 such that the contained sample portion 106 can be deposited into the receptacle 202 in which the punch device 101 is contained. Thus, the receiving array 200 has at least one receptacle 202 that contains a punch device 101 loaded with a sample portion 106. The receiving array 200 is then mounted onto a substrate, such as a microplate or a component which forms part of a flow cell (e.g., a functionalized glass slide).

Figure 3:
FIG. 3 is a flow diagram describing an embodiment of sample manipulation. First a sample is excised (i.e., punched or cut out such as in a die cut fashion) using a hollow punch device (sometimes referred to as a cutting device or cutter.) The punch devices (with samples loaded therein) are then loaded into a receiving array which may have a similar configuration (such as a similar structural configuration) to a microplate or any desired pattern. For example, the pattern may be configured for proper alignment within channels of a flow cell, such that the tissue sections are within the channels. The receiving array is mounted onto a substrate (e.g., a receiving substrate as described herein, such as a well of a microplate or a channel of a flow cell). Optionally, the receiving array may be inverted relative to the punch device(s) to control which surface (e.g., the biological sample or the carrier substrate) makes contact with the substrate. An array of one or more pistons are plunged (e.g., concurrently all at once, or selective plunging particular regions is contemplated) into each punch device to push or expel the cut out sample and aid in removal of the sample from the receiving array. Finally, the receiving array, pistons, and punch devices are removed such that the sample is retained on the substrate.
Figure 3:
Figure 3:
Figure 3:
Figure 6:
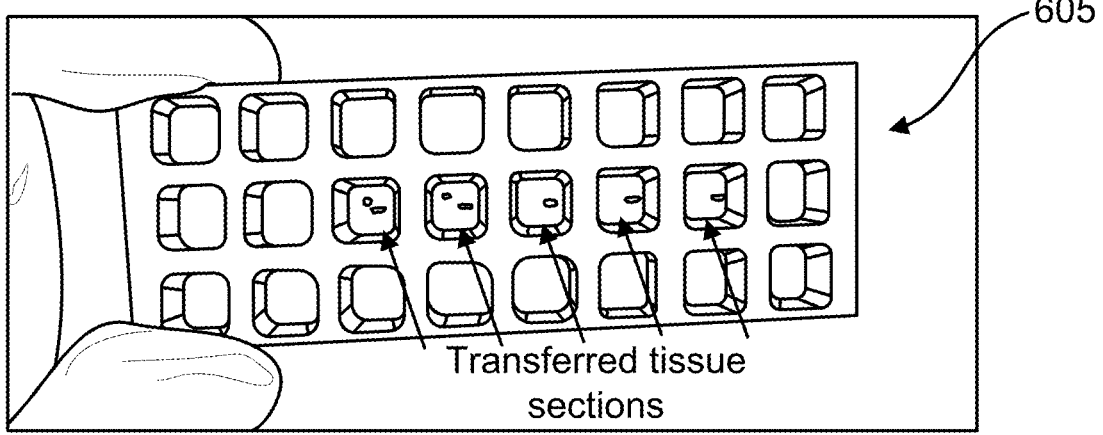
FIG. 6 shows 5 wells of a 24-well microwell plate containing at least a portion of a transferred tissue section within each well.

With reference still to FIG. 3, the piston array 206 is used to eject the sample portions 106 from the punch devices 101 into the receptacles 202. The piston array is 206 oriented with the receiving array 200 such that each rod 204 aligns with a corresponding receptacle 202. The rods 204 are then plunged into the receptacles and specifically into each hollow punch device 101 in a piston manner so that the rods 204 expel the sample portions 106 onto the receiving substrate. The piston array 206 can be used to deposit the sample portions 106 onto any receiving structure aside from the microplate. For example, the sample portions 106 may be affixed to the surface of a flow cell (e.g., a functionalized glass slide containing polymers, a resist, and/or one or more bioconjugate reactive moieties). The receiving array, piston array, and punch devices are then removed such that the sample is retained on the microplate. FIG. 6 shows an example microwell plate 605 containing one or more portions of transferred tissue section.

FIGS. 7A-7C schematically show a method of using a carrier substrate for capture and transfer of a tissue section onto a glass substrate (e.g., a well of a multiwell carrier or microwell plate 605). In an example implementation shown in FIG. 7A, the carrier substrate is an agarose gel and is prepared and placed in a warm water bath (e.g., maintained at a temperature between 42° C. and 67° C.). An FFPE tissue section floats in the water bath, followed by contacting the tissue section with the agarose gel to layer it atop the agarose. A brush (e.g., paint brush) or additional tool may be necessary to aid in transfer. The carrier substrate can maintain a hydrated interfacial surface (i.e., a plurality of water molecules at the surface forming an interstitial water layer) between the tissue section and the carrier substrate. The tissue section and agarose gel (collectively referred to as the sample-carrier construct 105) are removed from the warm water bath and allowed to cool without completely drying out.

Next, the punch device 101 is used to form a sample portion 106 of the construct. In addition, multiple sample portion 106 may be made from a single tissue section. The sample portion 106 are then mounted onto a functionalized glass slide by bringing the tissue section in contact with the glass surface such as by using a piston of a piston array as described above. The glass, tissue section, and carrier substrate (e.g., agarose) may then heated to facilitate removal of the carrier substrate while retaining the tissue section on the glass surface. Alternatively, the carrier substrate (e.g., an agarose gel) is physically removed (e.g., with forceps or tweezers). In embodiments, the assembly is heated to about 30° C.-50° C. In embodiments, the assembly is heated to at least 37° C. In embodiments, the assembly is heated to about 37° C. In embodiments, the assembly is heated to about 50° C. In embodiments, the assembly is heated to about 50° C. for about 30 seconds and then cooled to 37° C. for about 5 minutes.

In an aspect is provided a method of manipulating a biological sample, including: cutting a sample portion from the biological sample using a punch device such that the punch device contains the sample portion; mounting the punch device containing the sample portion onto a receiving substrate (e.g., inverting the punch device); pushing the sample portion out of the punch device using a piston, so that all or a portion thereof of the sample portion is positioned on the receiving substrate. In embodiments, the method further includes affixing a second solid support wherein the second solid support is configured to define a reaction chamber when attached to the first solid support (e.g., thereby forming a flow cell). In embodiments, one or more reaction chambers (e.g., flow cell channels) are formed.

In another aspect is provided a method of manipulating a biological sample, including: cutting a sample portion from the biological sample using a punch device such that the punch device contains the sample portion; mounting the punch device containing the sample portion into a receptacle of a receiving array; mounting the receiving array onto a substrate; pushing the sample portion out of the punch device using a piston so that the sample portion is positioned on the substrate. In embodiments, the method further includes heating the substrate. In embodiments, the method further includes forming a flow cell assembly from the substrate (e.g., according to the methods described herein) and flowing reagents into the flow cell to detect biomolecules in the biological sample (e.g., proteins and/or RNA molecules).

In an aspect is provided a method of manipulating a biological sample, including: cutting a sample portion from the biological sample using a punch device such that the punch device contains the sample portion; mounting the punch device containing the sample portion into a receptacle of a receiving array, wherein the receiving array is coupled to a solid support; pushing the sample portion out of the punch device using a piston so that the sample portion is positioned on the solid support. In embodiments, the method is repeated to position a plurality of sample portions on the solid support. In embodiments, the method further includes affixing a second solid support wherein the second solid support is configured to define a reaction chamber when attached to the first solid support (e.g., thereby forming a flow cell). In embodiments, one or more reaction chambers (e.g., flow cell channels) are formed.

In yet another aspect is provided a method of manipulating a biological sample, including: cutting a sample portion from the biological sample using two or more punch devices such that each punch device contains a different the sample portion; mounting each punch device containing the sample portion into a receptacle of a receiving array; mounting the receiving array onto a substrate; pushing the sample portions out of the punch devices using one or more pistons so that the sample portions are positioned on the substrate.

In embodiments, the method includes immobilizing the tissue section onto a carrier substrate to generate a sample-carrier construct, wherein the carrier substrate includes a first adhesion strength; and contacting the tissue section of the sample-carrier construct with a receiving substrate to generate an immobilized tissue section, wherein the receiving substrate includes a second adhesion strength, wherein the second adhesion strength is greater than the first adhesion strength. In embodiments, the second adhesion strength is at least 20%, at least 40%, at least 60%, or at least 80% greater than the first adhesion strength. In embodiments, the second adhesion strength is at least 20% greater than the first adhesion strength. In embodiments, the second adhesion strength is at least 40% greater than the first adhesion strength. In embodiments, the second adhesion strength is at least 60% greater than the first adhesion strength. In embodiments, the second adhesion strength is at least 80% greater than the first adhesion strength.

In embodiments, the first adhesion strength is in a range such that the immobilization of the tissue section onto the carrier substrate is reversible (e.g., the tissue section is not damaged to an unacceptable degree following contact of the tissue section with the receiving substrate and removal of the carrier substrate). In embodiments, the second adhesion strength is in a range such that the movement of the tissue section upon, or immediately after, contact with the receiving substrate is restricted. In embodiments, the first adhesion strength of the carrier substrate is low upon immobilization of the tissue section onto the carrier substrate, such that the tissue section may be repositioned on the carrier substrate (e.g., repositioned without damaging the tissue section to an unacceptable degree). In embodiments, the adhesion strength (e.g., the first adhesion strength and/or the second adhesion strength) may be measured as a shear strength or a tensile strength. For example, shear strength is the strength of a material against the type of yield when the material fails under a shear load. A shear load is a force that tends to produce a sliding failure on a material along a plane that is parallel to the direction of the force. In embodiments, the shear strength is less than about 0.1 kPa to 2 MPa. In embodiments, the shear strength is less than 2 MPa, less than 1 MPa, less than 500 kPa, less than 200 kPa, less than 100 kPa, less than 10 kPa, less than 1 kPa, or less than 0.1 kPa.

In embodiments, cutting a sample portion includes pressing a bottom edge of the punch device onto the biological sample so that the bottom edge cuts through the biological sample, and optionally a carrier substrate.

In embodiments, the sample portion remains inside an internal cavity of the punch device after the punch device cuts through the biological sample.

In embodiments, the piston inserts through an internal cavity of the punch device as it pushes all or a portion of the sample portion out of the punch device.

In embodiments, the method further includes removing the receiving array, piston, and punch device from the substrate.

In embodiments, the method includes arranging the biological samples in a pattern on the substrate. In embodiments, the biological samples do not contact each other.

In embodiments, the first solid support or the second solid support includes an infrared (IR) reflective coating. In embodiments, the first solid support includes an IR reflective coating. In embodiments, the second solid support includes an IR reflective coating. In embodiments, the IR reflective coating is attached to the first solid support. In embodiments, the IR reflective coating is attached to the second solid support. In embodiments, the IR reflective coating includes metal oxides. In embodiments, the IR reflective coating includes titanium dioxide, zinc oxide, tin oxide, tantalum pentoxide, silicon dioxide, indium tin oxide, silver-based coating, ceramic-based coating or a combination thereof. In embodiments, the IR reflective coating includes tantalum pentoxide ($Ta_2O_5$) and silicon dioxide ($SiO_2$). In embodiments, the IR reflective coating reflects near-infrared radiation (NIR). In embodiments, the IR reflective coating reflects mid- or far-infrared radiation. In embodiments, the IR reflective coating reflects wavelengths greater than 750 nm. In embodiments, the IR reflective coating reflects wavelengths greater than 760 nm. In embodiments, the IR reflective coating reflects wavelengths greater than 770 nm. In embodiments, the IR reflective coating reflects wavelengths greater than 780 nm. In embodiments, the IR reflective coating reflects wavelengths greater than 790 nm. In embodiments, the IR reflective coating reflects wavelengths greater than 800 nm. In embodiments, the IR reflective coating reflects wavelengths from about 750 nm to 1,000 μm. In embodiments, the infrared (IR) reflective coating includes one or more layers of silicon dioxide ($SiO_2$) and tantalum pentoxide ($Ta_2O_5$). A multilayer configuration leverages the distinct optical properties of both materials to enhance the IR reflectivity. Silicon dioxide, known for its low refractive index, and tantalum pentoxide, recognized for its high refractive index, are alternately layered to create a stack that exhibits high reflectance in the infrared spectrum. The alternating layers of $SiO_2$ and $Ta_2O_5$ result in constructive interference of light at specific wavelengths, thereby enhancing the IR reflective capability of the coating. The number and thickness of these layers can be tailored to target specific wavelengths within the IR range, or permitting a certain percentage of radiation to transmit. For example, the IR reflective coating may reflect 2-3% of the total IR radiation, and it absorbs or transmits 97-98% of the IR radiation. In embodiments, the IR reflective coating enables the autofocus mechanisms in optical instruments (e.g., fluorescence microscopy instruments) to provide consistent signal across various z-heights (e.g., the depth of an image). In embodiments, the IR reflective coating increases the amount of light reflected to the autofocus sensor to provide consistent signal across various z-heights. In embodiments, the IR reflective coating improves the signal to noise ratio of an image acquired by an optical instrument.

In embodiments, the method further includes obtaining an image of a tissue section, the method including: immobilizing the tissue section onto a carrier substrate to generate a sample-carrier construct including the carrier substrate and the tissue section; cutting a sample portion from the sample-carrier construct using a punch device such that the punch device contains the sample portion; mounting the punch device containing the sample portion onto a receiving substrate; pushing the sample portion out of the punch device using a piston so that the sample portion is positioned on the receiving substrate, and imaging the tissue section, thereby obtaining an image of the tissue section. In embodiments, the imaging (e.g., step E)) includes phase-contrast microscopy, bright-field microscopy, Nomarski differential-interference-contrast microscopy, dark field microscopy, electron microscopy, or cryo-electron microscopy. In embodiments, the imaging reagents or stains include phase-contrast microscopy, bright-field microscopy, Nomarski differential-interference-contrast microscopy, or dark field microscopy imaging reagents. In embodiments, the light transmittance of the sample is measured. For example, light transmittance may be measured with a visible near-infrared optical fiber spectrometer, wherein a circular spot of light (e.g., diameter, 5 mm) is irradiated on the central part a sample and the transmitted light is collected using an optical sensor.

In embodiments, the method includes imaging the immobilized tissue section. In embodiments, the method further includes an imaging modality, immunofluorescence (IF), or immunohistochemistry modality (e.g., immunostaining). In embodiments, the method includes ER staining (e.g., contacting the tissue section with a cell-permeable dye which localizes to the endoplasmic reticula), Golgi staining (e.g., contacting the tissue section with a cell-permeable dye which localizes to the Golgi), F-actin staining (e.g., contacting the tissue section with a phalloidin-conjugated dye that binds to actin filaments), lysosomal staining (e.g., contacting the tissue section with a cell-permeable dye that accumulates in the lysosome via the lysosome pH gradient), mitochondrial staining (e.g., contacting the tissue section with a cell-permeable dye which localizes to the mitochondria), nucleolar staining, or plasma membrane staining. For example, the method includes live cell imaging (e.g., obtaining images of the tissue section) prior to or during fixing, immobilizing, and permeabilizing the tissue section. Immunohistochemistry (IHC) is a powerful technique that exploits the specific binding between an antibody and antigen to detect and localize specific antigens in cells and tissue, commonly detected and examined with the light microscope. Known IHC modalities may be used, such as the protocols described in Magaki, S., Hojat, S. A., Wei, B., So, A., & Yong, W. H. (2019). *Methods in molecular biology* (Clifton, N.J.), 1897, 289-298, which is incorporated herein by reference. In embodiments, the additional imaging modality includes bright field microscopy, phase contrast microscopy, Nomarski differential-interference-contrast microscopy, or dark field microscopy. In embodiments, the method further includes determining the cell morphology of the tissue section (e.g., the cell boundary or cell shape) using known methods in the art. For example, to determining the cell boundary includes comparing the pixel values of an image to a single intensity threshold, which may be determined quickly using histogram-based approaches as described in Carpenter, A. et al Genome Biology 7, R100 (2006) and Arce, S., Sci Rep 3, 2266 (2013)). By "microscopic analysis" is meant the analysis of a specimen using techniques that provide for the visualization of aspects of a specimen that cannot be seen with the unaided eye, i.e., that are not within the resolution range of the normal human eye. Such techniques may include, without limitation, optical microscopy, e.g., bright field, oblique illumination, dark field, phase contrast, differential interference contrast, interference reflection, epifluorescence, confocal microscopy, CLARITY-optimized light sheet microscopy (COLM), light field microscopy, tissue expansion microscopy, etc., laser microscopy, such as, two photon microscopy, electron microscopy, and scanning probe microscopy. By "preparing a biological specimen for microscopic analysis" is generally meant rendering the specimen suitable for microscopic analysis at an unlimited depth within the specimen. In embodiments, the immobilized tissue section is imaged using "optical sectioning" techniques, such as laser scanning confocal microscopes, laser scanning 2-Photon microscopy, parallelized confocal (i.e. spinning disk), computational image deconvolution methods, and light sheet approaches. Optical sectioning microscopy methods provide information about single planes of a volume by minimizing contributions from other parts of the volume and do so without physical sectioning. The resulting "stack" of such optically sectioned images, represents a full reconstruction of the 3-dimensional features of a tissue volume. Rotational orientation for each punch device and tissue should be accounted for to aid in alignment of stacks of images. A typical confocal microscope includes a 10×/0.5 objective (dry; working distance, 2.0 mm) and/or a 20×/0.8 objective (dry; working distance, 0.55 mm), with a s z-step interval of 1 to 5 μm. A typical light sheet fluorescence microscope includes an sCMOS camera, a 2×/0.5 objective lens, and zoom microscope body (magnification range of ×0.63 to ×6.3). For entire scanning of whole samples, the z-step interval is 5 or 10 μm, and for image acquisition in the regions of interest, an interval in the range of 2 to 5 μm may be used.

To microscopically visualize tissue sections prepared by the subject methods, in some embodiments the tissue section is embedded in a mounting medium. Mounting medium is typically selected based on its suitability for the reagents used to visualize the cellular biomolecules, the refractive index of the tissue section, and the microscopic analysis to be performed. For example, for phase-contrast work, the refractive index of the mounting medium should be different from the refractive index of the specimen, whereas for bright-field work the refractive indexes should be similar. As another example, for epifluorescence work, a mounting medium should be selected that reduces fading, photobleaching or quenching during microscopy or storage. In certain embodiments, a mounting medium or mounting solution may be selected to enhance or increase the optical clarity of the cleared tissue specimen. Nonlimiting examples of suitable mounting media that may be used include glycerol, CC/Mount™, Fluoromount™ Fluoroshield™, ImmunHistoMount™ Vectashield™, Permount™, Acrytol™, CureMount™, FocusClear™, or equivalents thereof.

The biological targets or molecules to be detected can be any biological molecules including but not limited to proteins, nucleic acids, lipids, carbohydrates, ions, or multicomponent complexes containing any of the above. Examples of subcellular targets include organelles, e.g., mitochondria, Golgi apparatus, endoplasmic reticulum, chloroplasts, endocytic vesicles, exocytic vesicles, vacuoles, lysosomes, etc. Exemplary nucleic acid targets can include genomic DNA of various conformations (e.g., A-DNA, B-DNA, Z-DNA), mitochondria DNA (mtDNA), mRNA, tRNA, rRNA, hRNA, miRNA, and piRNA. For example, following immobilization on the receiving substrate, the sections may be fixed with methanol, permeabilized with 0.025% Triton in PBS solution, and stained with primary antibodies directed against vimentin (fibroblasts) and macrophages, followed by secondary antibody labeling (e.g., Alexa-594 conjugated secondary antibodies). Additional counterstaining may be performed, for example using 4,6-diamidino-2-phenylindole (DAPI) mounting media to counterstain nuclei.

In embodiments, the collection of information (e.g., sequencing information and cell morphology) is referred to as a signature. The term "signature" may encompass any gene or genes, protein or proteins, or epigenetic element(s) whose expression profile or whose occurrence is associated with a specific cell type, subtype, or cell state of a specific cell type or subtype within a population of cells. It is to be understood that also when referring to proteins (e.g., differentially expressed proteins), such may fall within the definition of "gene" signature. Levels of expression or activity or prevalence may be compared between different cells in order to characterize or identify for instance signatures specific for cell (sub)populations. Increased or decreased expression or activity of signature genes may be compared between different cells in order to characterize or identify for instance specific cell (sub)populations.

In embodiments, the methods described herein may further include constructing a 3-dimensional pattern of abundance, expression, and/or activity of each target from spatial patterns of abundance, expression, and/or activity of each target of multiple samples. In embodiments, the multiple samples can be consecutive tissue sections of a 3-dimensional tissue sample.

In embodiments, the biological sample includes a biomolecule. In embodiments, the method further includes detecting the biomolecule. Means for detecting biomolecules are described, for example, in U.S. Pat. Nos. 11,492,662; 11,643,679; 11,434,525; 11,680,288; and/or U.S. Pat. No. 11,753,678, each of which are incorporated herein in their entirety.

In embodiments, the biomolecule to be detected in the tissue section or in the cell is contacted with a detection agent. In embodiments, the biomolecule to be detected on the surface of the tissue section or on the surface of a cell is contacted with a detection agent. In embodiments, the detection agent includes a protein-specific binding agent. In embodiments, the detection agent includes a protein-specific binding agent bound to a nucleic acid sequence, bioconjugate reactive moiety, an enzyme, or a fluorophore. In embodiments, the protein-specific binding agent is an antibody, single domain antibody, single-chain Fv fragment (scFv), antibody fragment-antigen binding (Fab), affimer, or an aptamer. In embodiments, the protein-specific binding agent is an antibody. In embodiments, the protein-specific binding agent is a single domain antibody. In embodiments, the protein-specific binding agent is a single-chain Fv fragment (scFv). In embodiments, the protein-specific binding agent is an antibody fragment-antigen binding (Fab). In embodiments, the protein-specific binding agent is an affimer. In embodiments, the protein-specific binding agent is an aptamer.

In embodiments, the detection agent includes a protein-specific binding agent or oligonucleotide-specific binding agent. In embodiments, the detection agent includes a protein-specific binding agent. In embodiments, the detection agent includes an oligonucleotide-specific binding agent. In embodiments, the detection agent includes an oligonucleotide-specific binding agent including an identifying nucleic acid sequence. In embodiments, the detection agent includes an oligonucleotide-specific binding agent bound to a bioconjugate reactive moiety, an enzyme, or a fluorophore.

In embodiments, the method includes forming a circular polynucleotide in the cell or tissue. In embodiments, forming the circular polynucleotide includes a) hybridizing a circularizable oligonucleotide to a target nucleic acid (e.g., an RNA molecule), wherein the circularizable oligonucleotide includes a first region at a 3' end that hybridizes to a first complementary region of the target nucleic acid, and a second region at a 5' end that hybridizes to a second complementary region of the target nucleic acid, wherein the second complementary region is 5' with respect to the first complementary region and b) circularizing the circularizable oligonucleotide to generate a circular polynucleotide, wherein circularizing includes optionally extending the 3' end of the circularizable oligonucleotide (e.g., extending the 3' end using a polymerase to incorporate one or more nucleotides) along the target nucleic acid to generate a complementary sequence (e.g., complementary to the target nucleic acid, for example a target RNA sequence), and ligating the complementary sequence to the 5' end of the oligonucleotide primer.

In embodiments, the method includes binding a polynucleotide to a nucleic acid molecule in the cell or tissue. In embodiments, the method includes binding a first sequence and a second sequence of the polynucleotide to the nucleic acid molecule. In embodiments, the method includes ligating the first sequence and second sequence together to form a circular polynucleotide. In embodiments, the method includes amplifying the circular polynucleotide to form amplification products. In embodiments, the method includes detecting the amplification products (e.g., sequencing the amplification products). In embodiments, detecting the amplification product includes hybridizing an oligonucleotide associated with a detectable label to the amplification product and identifying the detectable label. In embodiments, detecting includes serially contacting the amplification products with labeled probes (e.g., labeled oligonucleotides or labeled nucleotides). In embodiments, detecting the amplification product includes sequencing the amplification products.

In embodiments, the amplifying includes rolling circle amplification (RCA) or rolling circle transcription (RCT) (see, e.g., Lizardi et al., Nat. Genet. 19:225-232 (1998), which is incorporated herein by reference in its entirety). Several suitable rolling circle amplification methods are known in the art. For example, RCA amplifies a circular polynucleotide (e.g., DNA) by polymerase extension of an amplification primer complementary to a portion of the template polynucleotide. This process generates copies of the circular polynucleotide template such that multiple complements of the template sequence arranged end to end in tandem are generated (i.e., a concatemer) locally preserved at the site of the circle formation. In embodiments, the amplifying occurs at isothermal conditions. In embodiments, the amplifying includes hybridization chain reaction (HCR). HCR uses a pair of complementary, kinetically trapped hairpin oligomers to propagate a chain reaction of hybridization events, as described in Dirks, R. M., & Pierce, N. A. (2004) PNAS USA, 101(43), 15275-15278, which is incorporated herein by reference for all purposes. In embodiments, the amplifying includes branched rolling circle amplification (BRCA); e.g., as described in Fan T, Mao Y, Sun Q, et al. Cancer Sci. 2018; 109:2897-2906, which is incorporated herein by reference in its entirety. In embodiments, the amplifying includes hyberbranched rolling circle amplification (HRCA). Hyperbranched RCA uses a second primer complementary to the first amplification product. This allows products to be replicated by a strand-displacement mechanism, which yields drastic amplification within an isothermal reaction (Lage et al., Genome Research 13:294-307 (2003), which is incorporated herein by reference in its entirety).

In embodiments, the first sequence and the second sequence are adjacent. For example, the first sequence and the second sequence, when bound to the target nucleic acid molecule, do not include a gap sequence between the two sequences. In alternative embodiments, the first sequence and the second sequence are separated by 1 or more nucleotides. For example, in embodiments, the first sequence and the second sequence, when bound to the target nucleic acid molecule, form a gap sequence including 1, 2, 3, 4, 5, 6, 7, 8, 9, 10, or more nucleotides. In embodiments, the gap sequence is 5, 10, 15, 20, 25, 30, 40, 50, 60, 70, 80, 90, 100, 125, 150, 175, or 200 nucleotides. In embodiments, the gap sequence is 5 to 150 nucleotides. In embodiments, the gap sequence is 1, 2, 3, 4, or 5 nucleotides.

In embodiments, the method further includes binding a specific binding reagent (e.g., an antibody, affimer, or aptamer) to a protein in the cell or tissue, wherein the specific binding reagent includes an oligonucleotide. In embodiments, the method includes binding a polynucleotide to the oligonucleotide. In embodiments, the method includes binding a first sequence and a second sequence of the polynucleotide to the oligonucleotide. In embodiments, the method includes ligating the first sequence and second sequence together to form a circular polynucleotide. In embodiments, the method includes amplifying the circular polynucleotide to form amplification products. In embodiments, the specific binding reagent is covalently attached to the oligonucleotide. In embodiments, sequencing the oligonucleotide includes hybridizing a sequencing primer to the amplification products and incorporating a labeled nucleotide into the sequencing primer and detecting the incorporated nucleotide. In embodiments, additional proteins may be detected with different specific binding reagents bound to different oligonucleotides containing different sequences, wherein each oligonucleotide is associated with the identity of the specific binding reagent, and thus the protein of interest.

In embodiments, the sequencing includes sequencing by synthesis, sequencing by hybridization, sequencing by binding, sequencing by ligation, or pyrosequencing. In embodiments, the sequencing includes extending a sequencing primer by incorporating a labeled nucleotide or labeled nucleotide analogue, and detecting the label to generate a signal for each incorporated nucleotide or nucleotide analogue, wherein the sequencing primer is hybridized to the extension product. In embodiments, sequencing includes a plurality of sequencing cycles. In embodiments, sequencing includes 1, 2, 3, 4, 5, 6, 7, 8, 9, 10, 11, 12, 13, 14, or 15 sequencing cycles. In embodiments, sequencing includes at least 10, 20, 30 40, or 50 sequencing cycles. In embodiments, sequencing includes at least 10 sequencing cycles. In embodiments, sequencing includes 10 to 20 sequencing cycles. In embodiments, sequencing includes 10, 11, 12, 13, 14, or 15 sequencing cycles. In embodiments, sequencing includes (a) extending a sequencing primer by incorporating a labeled nucleotide, or labeled nucleotide analogue and (b) detecting the label to generate a signal for each incorporated nucleotide or nucleotide analogue.

In an aspect is provided a method of detecting a protein in a cell or tissue, wherein the cell or tissue is attached to the solid support as described herein (e.g., attached to the solid support according to the methods described herein). In embodiments, the method includes contacting each of the proteins with a specific binding reagent, wherein the specific binding reagent includes an oligonucleotide barcode; hybridizing a padlock probe to two nucleic acid sequences of the barcode, wherein the padlock probe is a single-stranded polynucleotide having a 5' and a 3' end, wherein the padlock probe comprises a primer binding sequence from a known set of primer binding sequences; amplifying the barcode sequence according to a method described herein (e.g., in an aspect provided herein); sequencing each barcode to obtain a multiplexed signal in the cell in situ; demultiplexing the multiplexed signal by comparison with the known set of barcodes; and detecting the plurality of targets by identifying the associated barcodes detected in the cell.

In an aspect is provided a method of sequencing, the method including contacting a cell or tissue including a nucleic acid molecule with a polynucleotide probe including a first target hybridization sequence and a second target hybridization sequence; hybridizing the first target hybridization sequence to the nucleic acid molecule and hybridizing the second target hybridization sequence to the nucleic acid molecule; ligating the first target hybridization sequence to the second target hybridization sequence to form a circular polynucleotide; amplifying the circular polynucleotide to form an amplification product according to the method described herein; and hybridizing a first sequencing primer to the amplification product, and sequencing the first target hybridization sequence or the second target hybridization sequence, wherein the cell or tissue is affixed to a solid support as described herein.

In embodiments, the circular polynucleotide includes an endogenous nucleic acid sequence, or a complement thereof. In embodiments, the circular polynucleotide includes a genomic sequence, or a complement thereof. In embodiments, the circular polynucleotide includes a synthetic sequence, or a complement thereof.

In embodiments, the method includes amplifying the circular polynucleotide of the cell in situ. In embodiments, amplifying the circular polynucleotide generates an amplification product. In embodiments, the amplification product includes three or more copies of the circular polynucleotide. In embodiments, the amplification product includes at least three or more copies of the circular polynucleotide. In embodiments, the amplification product includes at least five or more copies of the circular polynucleotide. In embodiments, the amplification product includes at 5 to 10 copies of the circular polynucleotide. In embodiments, the amplification product includes 10 to 20 copies of the circular polynucleotide. In embodiments, the amplification product includes 20 to 50 copies of the circular polynucleotide.

In embodiments, the method includes contacting the sample portion with a detection agent comprising a fluorophore, and detecting an emission from the fluorophore. In embodiments, the detectable agents could be conjugated to biomolecule-specific binding agents (e.g., antibodies). In embodiments, the solid support as described herein could have a composition containing detectable moieties (e.g., dyes or fluorochromes) in various ratios or concentrations that permit the detection of the solid support. Upon being exposed to an absorption light, the detectable agent will emit an emission light. The presence of an emission light can indicate the presence of the biomolecule-specific binding agents (and therefore, the bound target) on the solid support.

In embodiments, the method includes contacting the sample portion with amplification reagents and amplifying a nucleic acid molecule in the sample portion. In embodiments, the amplification reagents refer to an aqueous mixture that contains the reagents necessary to add a nucleotide (e.g., dNTP or dNTP analogue) to a DNA strand by a DNA polymerase. In embodiments, the sequencing reaction mixture includes a buffer. In embodiments, the amplification reagents include a suitable polymerase, a suitable primer or set of primers, suitable nucleotides (e.g., dNTPs), and a suitable buffer. In embodiments, amplification reagents, tailored for the amplification of a target nucleic acid molecule in the sample portion, may encompass an array of components. This array includes deoxynucleoside triphosphates (dNTPs), such as adenine, guanine, cytosine, and thymine; a thermostable DNA polymerase; and a suite of custom-designed primers which bind precisely to the target nucleic acid sequence, facilitating the initiation of amplification. The formulation may further include salts, such as magnesium chloride or sodium chloride. In embodiments, the amplification reagents includes betaine or dimethyl sulfoxide (DMSO), and a molecular crowding agent, such as polyethylene glycol (PEG).

EXAMPLES

Example 1. Carrier-Assisted Tissue Section Transfer

Biopsies and cytology specimens typically include cell and tissue sections and are a major component of disease research and clinical pathology. Unstained slides derived from formalin-fixed paraffin-embedded (FFPE) tissue sections may be analyzed using hematoxylin and eosin (H&E) histology techniques, immunohistochemistry/immunofluorescence assays and protocols, and chromogenic or fluorescent in situ hybridization methods. H&E staining of FFPE sections reviewed by a pathologist are highly valuable to ensure the presence of suitable lesional cells for molecular and other analyses (Sy J and Ang LC. Methods Mol. Biol. 2019; 1897:269-278). In addition to standard morphology-based imaging, more current approaches are interrogating the spatial and structural context of specimens. For example, in situ gene expression approaches, such as those commercialized by 10× Genomics, Interpace Biosciences, Thermo Fisher Scientific, and others represent an emerging area of spatial genomics. In addition, multiplexed in situ proteomic expression approaches such as those commercialized by Akoya Biosciences, Fluidigm, Ionpath, and others are developing complementary spatial proteomics approaches. For example, in situ gene expression methods typically involve attaching a section of a frozen tissue of interest to patterned microarrays carrying spatially barcoded oligo-dT primers that capture the polyadenylated transcriptome contained within the tissue section. Each spot on the microarray contains a capture probe with a spatial barcode unique to that spot allowing the individual sequencing reads to be mapped to the originating spot. After cDNA synthesis on the surface via reverse transcription, the tissue is removed and the mRNA-cDNA hybrids are released from the array to be prepared for sequencing on a separate platform; see Vickovic, S., et al. Nat. Methods 16, 987-990 (2019) for greater detail on the approach. In parallel, multiplex protein measurements in situ enable profiling multiple detectable tags simultaneously (e.g., cyclical immunostaining).

A number of new techniques have been described for reading out RNA transcription levels in tissue sections directly (i.e., in situ), without requiring spatial barcoding, based on single molecule fluorescence in situ hybridization. These include MERFISH (Multiplexed Error-Robust Fluorescence In Situ Hybridization), STARmap (Spatially-resolved Transcript Amplicon Readout mapping), FISSEQ, BaristaSeq, seq-FISH (Sequential Fluorescence In Situ Hybridization) and others (see for example Chen, K. H., et al. (2015). Science, 348(6233), aaa6090; Wang, G., Moffitt, J. R. & Zhuang, X. Sci Rep. 2018; 8, 4847; Wang X. et al; Science, 2018; 27, Vol 361, Issue 6400, eaat5691; Cai, M. *Dissertation*, (2019) UC San Diego. ProQuest ID: Cai_ucsd_0033D_18822; and Sansone, A. Nat Methods 16, 458; 2019). In these techniques, individual RNA transcripts are individually resolved, typically with pre-amplification or requiring multiple instances of labeled probes. Some of these techniques have been combined with super-resolution microscopy, expansion microscopy, or both, to increase the resolution and allow more transcripts to be resolved and thus counted.

Methods for acquiring, preparing, and storing tissue sections for either immediate or future analysis have been largely unchanged for decades. For example, when a patient has a biopsy or surgery, the surgeon often removes a portion of tissue for examination by a pathologist. Typically when dealing with biopsy samples, the recommended approach is to process the samples by embedding individually in a supporting material such as a paraffin block or freezing the sample. The resected tissue may be snap-frozen in liquid nitrogen shortly after surgical resection, generating what is commonly referred to as "fresh frozen" tissue. Freshly obtained tissue samples require snap freezing to prevent RNA degradation and avoid crystal formation, which can cause physical damage to the tissue architecture. Once frozen, tissue samples are embedded in a freezing and embedding compound, referred to as optimal cutting temperature (OCT), to preserve the structure of the tissue and provide structural support during subsequent cryosectioning. Alternatively, preservation techniques such as formalin-fixation and paraffin embedding (FFPE) are widely used for preserving the macroscopic architecture of cellular structures (e.g., preserve tissue architecture, cell shape, and the components of the cell, such as proteins, carbohydrates, and enzymes) in tissue sections but are known to damage and alter nucleic acids. Prolonged formalin fixation causes the crosslinking of proteins and nucleic acids and random breakages in nucleotide sequences rendering downstream analyses a challenge. Fresh frozen tissue is the preferred sample for detecting gene mutations due to its superiority in preserving DNA, while FFPE tissue provides the benefits of ease of storage and preservation of cellular and architectural morphology. However, the fixation and archiving process in FFPE often leads to the cross-linking, degradation, and fragmentation of DNA molecules (Gao X H et al. Front. Oncol. 2020; 10: 310). In recent years with the development of additional technologies to further analyze the sample (e.g., spatial gene expression and/or proteomic analyses), extracting or transferring the sample from a glass slide/ transitional surface to another medium would be an attractive step in the processing of tissue samples. However, subsequent transfer of the tissue section to another surface often introduces additional damage to the sample. For example, once the tissue section is attached to the first surface (e.g., a typical biopsy slide, such as a charged glass surface), it may be extremely difficult to transfer again without damaging the tissue due to strong contact forces between the tissue section and attachment surface. Novel approaches for transferring biological specimens while minimizing damage are greatly needed.

Tissue samples, such as those taken by biopsy, are commonly formalin-fixed and paraffin embedded (FFPE) to allow for extended storage of the samples and the structure of the cell and sub-cellular components to be maintained. In such FFPE processing, the samples are typically fixed in a formalin solution (e.g., a 10% formalin solution may contain 3.7% formaldehyde and 1.0 to 1.5% methanol), which creates crosslinks between nucleic acids, between proteins and/or between nucleic acids and proteins. Afterward, the sample is dehydrated, e.g., by placing the sample in an alcohol, and exposed xylene. The sample is then embedded in paraffin, where the sample is surrounded by paraffin which replaces the xylene in the sample. The paraffin embedded sample (i.e., an FFPE block) can then be stored for extended periods of days, months, or years. At a desired time, the samples may then be transferred to a vessel or other system for further processing.

Once a tissue sample has been obtained and preserved (e.g., either a fresh frozen tissue block or FFPE tissue block), a scientist typically slices the tissue sample into very thin sections (e.g., sectioning using a microtome, vibratome, or cryotome). A vibratome (i.e., a vibrating microtome) is an instrument that uses a vibrating blade to cut thin slices of material, for example, from about 10 μm to about 300 μm in thickness (e.g., product number E0977 from Beyotime), or from about 1 mm to about 40 mm (e.g., model #VT1000S from Leica Biosystems). FFPE tissue sections, for example, are placed in a warm water bath and then mounted onto a glass slide following sectioning from a tissue block. The water bath temperature may be set about 5-10° C. below the melting point of paraffin (e.g., the water bath temperature is maintained at about 40-50° C.), and the tissue section is floated for several seconds or up to a few minutes to allow the section to spread open and remove any wrinkles prior to contacting the receiving substrate (i.e., the glass slide). The water bath temperature is highly dependent upon the ambient temperature in the room, the humidity, and the melting temperature of the wax. Typical water bath temperatures include about 37° C. to about 50° C. The temperature should be selected such that the water bath temperature is lower than the melting temperature of the wax, but high enough so that the section completely flattens out for even transfer. Once on the slide, the tissue section is baked at 50-60° C., to improve adherence to the slide. Next, the tissue section may be inspected under a microscope for proper positioning of the section prior to further processing. This process (i.e., mounting a tissue section onto a glass slide) leads to a strong attachment between the tissue section and the glass slide.

Transferring intact regions of interest from a tissue section into a vessel or another slide would be very advantageous for downstream analyses. Though it would be desirable to be able to transfer undamaged tissue sections from a prepared glass slide after sectioning, current technology is limited. Subsequent transfer of the tissue section, or region of interest, from the glass slide to another surface often introduces additional damage to the sample. For example, once the tissue section is attached to the first surface (e.g., a typical biopsy slide, such as a charged glass surface), it may be extremely difficult to transfer again without damaging the tissue section due to strong contact forces between the tissue section and attachment surface. Being able to effectively transfer tissue sections without damage or loss of material is critical when working with rare and valuable samples such as tissue biopsy specimens.

Current commercial solutions for spatial transcriptome analyses, such as the Visium Spatial Gene Expression method, requires that one to four sections be captured on a single slide using traditional approaches. A user interested in analyzing 4 FFPE samples using the Visium platform would need to float each corresponding tissue section in a water bath and catch them individually on the patterned slide, for example, in the small 6.5×6.5 mm oligo-patterned areas provided in a Visium Spatial Gene Expression Slide (10× Genomics, Item #PN-2000233). Not only are these protocols labor intensive, obtaining proper alignment and placement on the patterns slide is difficult due to the mobility of the tissue section on the surface of the as the water bath. Complicating matters, following capture and immobilization of a first tissue section, the sections may move again while retrieving subsequent tissue sections. Accordingly, the Visium for FFPE tissue protocol does not prevent the immobilized tissue sections from folding, wrinkling, or moving out of the specified target capture regions on the slide during this process.

Unique challenges arise when working with fresh frozen tissue sections. Usually upon contact with the slide, the frozen tissue sections melt and bind to the surface of the slide. To prevent the temperature differential, maintaining the slides at a reduced temperature (e.g., −20° C.) reduces tissue section thawing and allows for proper placement, however the tissue strongly adheres to the slide upon increasing the temperature. These issues are further complicated when attempting to place tissue sections directly into a concave well (e.g., a well of a microtiter plate). For example, the tissue sections may adhere to the walls of the wells due to various forces (e.g., electrostatic forces) that may interact with the tissue section during the transfer and mounting process. The devices and methods described herein provide approaches that overcome existing challenges in tissue transfer-associated damage through the introduction of a carrier layer between the tissue section and the attachment surface and allow for effective transfer of tissue sections to both slides and multi-well plates (e.g., a 6-well, 12-well, 24-well, 48-well, or 96-well plate) without significant physical damage to the tissue section.

Given the challenges described supra, few commercial solutions exist for transferring frozen tissue sections onto a slide. One offering for transferring frozen tissue sections is the CryoJane Tape-Transfer System from Leica Biosystems, which uses adhesive coated slides and adhesive tapes to capture sections (see, e.g., Yang Y et al. J. Orthop. Translat. 2020; 26:92-100, which is incorporated herein by reference in its entirety). Briefly, a strip of cold adhesive tape is affixed to the trimmed frozen tissue block and a section is then cut onto the tape. The tape with the frozen tissue section is then placed on a pre-coated cold adhesive slide. UV light is then applied to the slide, converting the adhesive coating into a hard, solvent-resistant plastic, and the tape is then peeled away. Other cryofilm-based approaches have been commercialized for similar processing of tissue sections, such as Cryofilm (#C-MK001-C2, cryofilm type 2C(9) 3.5 cm, Section lab, Hiroshima, Japan), as described in Ticha P et al. Scientific Reports. 2020; 10: 19510 and Kawamoto T. Arch. Histol. Cytol. 2003; 66(2): 123-143, each of which is incorporated by reference herein in its entirety. Recent modifications to the cryofilm protocol include a "sticker method", which combines cryofilm with OCT-embedded tissue samples to transfer tissue sections, instead of freeze-embedding of the tissue sample with CMC gel in hexane using a stainless-steel container, and subsequent UV light treatment (see, Ryu B et al. Journal of Neuroscience Methods. 2019; 328: 108436, which is incorporated herein by reference in its entirety). These adhesive-based frozen tissue section methods have a number of shortcomings that may affect downstream analyses. First, the films are applied at the time of sectioning the tissue, slowing down the tissue sectioning process for which timing is critical given the fragile nature of frozen tissue. Secondly, these tape-based methods rely on adhesive compounds which, following mounting of the tape-transferred tissue section, are removed with organic solvents (e.g., hexane), and may therefore not be compatible with commercial multi-well plates, many of which have poor chemical compatibility with organic solvents (e.g., multi-well plates made from polystyrene). These studies on adhesive tape-based transfer of frozen tissue sections also did not explore the stability of the tissue sections after transferring, for example, stability after heating and cooling the transferred tissue section. Adhesive removal, and treatment with solvents, may impact the structural integrity of the tissue sections when subjected to thermal variation.

The devices and methods described herein are applicable to both freshly cut tissue and frozen tissue samples, as well as preserved samples, and are compatible with a broad range of downstream applications such as in situ sequencing and proteomic analysis. In lieu of a glass slide, tissue sections are first mounted on a carrier substrate (e.g., a polymeric hydrogel), forming a sample-carrier construct. An overview of this process is provided in FIG. 1, for example. In embodiments, the carrier substrate includes a hydration layer (i.e., interfacial water layer) between the tissue section and the carrier substrate hydrated prior to transfer to a final substrate (e.g., a charged glass well). In contrast to the adhesive tape-based methods discussed supra, the carrier substrate described herein is free of adhesives and does not require UV curing following transfer to the final substrate. Reducing the strength of the tissue section adherence to the carrier substrate facilitates subsequent detachment and transference without damaging the tissue. Maintaining hydration of the tissue section is also useful for facilitating transfer from the carrier substrate to the final target surface. Under hydrated conditions, the tissue section is more likely to have complete contact with a hydration layer surface of the carrier substrate while exhibiting reduced contact forces, in comparison to dehydrated conditions. After dehydration, ideally once the tissue section is transferred to the final surface, strong surface interactions (e.g., van der Waals and/or electrostatic interactions) result in the tissue section being retained on the surface. For example, the carrier substrate may include agarose or gelatin.

The sample-carrier construct can undergo additional manipulations, see for example FIGS. 2A-2B that illustrates a workflow for the sample-carrier constructs. For example, FIG. 2A depicts a sample-carrier construct (i) wherein the sample is embedded in an embedding material, e.g., paraffin wax. The embedding material may then removed, for example when the embedding material is paraffin wax by contacting the construct with an organic solvent such as xylene or heptane, leaving the tissue section on the construct. Alternatively, the sample-carrier construct may be subjected to fluorogenic and/or chromogenic counterstaining (e.g., H&E staining) methods to aid in visualization and identifying details of the cell types, organelles, structures in the tissue section. Additionally, selected removal of one or more portions of the construct is contemplated. To a sample-carrier construct, (i), one or more portions of the construct are removed, for example using a cutting device, and depicted as dashed lines in step (ii). The resulting portions of the construct, illustrated in step (iii), are then placed into wells of a multiwell container (e.g., a 96-well microplate), such that the biological sample of the portion is in contact with the bottom of the receiving substrate (i.e., well), as shown in step (iv) of FIG. 2A. Alternatively the portions of the construct may be affixed to the surface of a flow cell, as illustrated in FIG. 2B.

In an embodiment, the tissue section is transferred from a carrier substrate (e.g., a hydrophilic polymeric layer) to a receiving substrate (e.g., charged glass surface). In embodiments, the carrier substrate includes agarose, gelatin, polyacrylamide, or any suitable hydrogel. In embodiments, the carrier substrate includes a hydrophilic surface (e.g., an interfacial water layer). The hydrophilic surface maintains the tissue section wet at the point of contact with the underlying attachment surface and prevents damage to the tissue during the transfer process. As an example, an agarose gel layer with similar dimensions to the charged glass slide is prepared for use as a carrier substrate using methods described. The concentration of agarose is chosen to provide optimal support for the tissue section to be transferred, and to prevent tissue section distortion during subsequent transfer steps. For example, an agarose gel medium is prepared by dissolving agarose powder in boiling deionized water such that the final concentration of the agarose gel is between 2% to 5%. The dissolved agarose is then poured into a 4-well plate mold and cooled to cast the gel. In embodiments, and depending on the thickness of the tissue section, an agarose concentration of at least 5% or higher may be preferable preferred when facilitating tissue transfer to avoid fracturing the agarose layer. Once the agarose surface is prepared, the agarose surface and tissue section (e.g., a FFPE tissue section) are contacted in a warm water bath (e.g., a water bath with a temperature setpoint of about 42° C.) such that the FFPE section can become captured on the surface of the agarose gel layer (see, e.g., FIG. 7A). The agarose contacted FFPE section is then removed from the incubation bath and allowed to cool. Portions of the agarose-FFPE construct are then cut and removed, (e.g., punched-out using a device as described herein), and subsequently mounted on a charged glass slide such that the FFPE section is contacted directly with the glass surface. The removed portion may be cut according to any dimension depending on the application, for example the diameter and dimensions of individual portions may be suitable for use in 96-well, 48-well, 24-well, and 12-well plates. Alternatively, the removed portion may be placed on a glass slide for use in a flow cell (e.g., FIGS. 9C-9D). The methods described herein may be cut to any of the dimensions depicted in FIG. 9A, or a dimension smaller (e.g., about 10% smaller) than the dimensions identified in FIG. 9A. The agarose-tissue section cutout is then heated (e.g., heated to a temperature between 42° C. or 67° C.) to facilitate release of the agarose layer, leaving behind the FFPE tissue section on the glass slide.

When considering a carrier substrate for effective tissue transfer onto a receiving substrate, for example, the carrier substrate composition (e.g., the percentage of agarose in an agarose gel layer) should withstand manipulation (e.g., have a Young's modulus to support handling by a user during tissue section catching, cutting, and transferring, wherein the Young's modulus is between about 5 kPa to about 2.5 MPa, or more) while effectively transferring the tissue section onto the receiving substrate. Several tissue section samples were transferred from a series of agarose gel layers, wherein each agarose gel layer contained a different weight percentage of agarose (e.g., 0.5%, 1%, 2%, 5%, or 10%, as indicated in the photograph). Both 0.5% and 1% agarose gel layers effectively transferred the tissue sections, but may require additional care while handling due to their low expected compression modulus (e.g., about 5 kPa and about 40 kPa, respectively), in contrast with the 2%, 5%, and 10% agarose gel layers, each of which have a higher expected compression modulus (e.g., about 100 kPa, about 900 kPa, and about 2.5 MPa, respectively). An agarose gel layer with a higher compression modulus of about 100 kPa to about 1 MPa, or more, may therefore provide easier handling while retaining effective tissue transfer properties as described herein. Additional information on the mechanical properties of agarose gels is described, e.g., in Normand V. et al. Biomacromolecules. 2000; 1(4): 730-8, which is incorporated herein by reference in its entirety.

To examine the amount of force required to cut through the hydrogel polymer (e.g., a 5% agarose polymeric slab) we took a 5 mm thick slab. After obtaining a cutter on the surface and exerting a force as measured by the force gauge, we determined the amount of force required to cut through a polymeric slab. The smaller the perimeter of the cutting tool, the less force is required. On average 1.63 pounds of force is required.

Figure 9D:
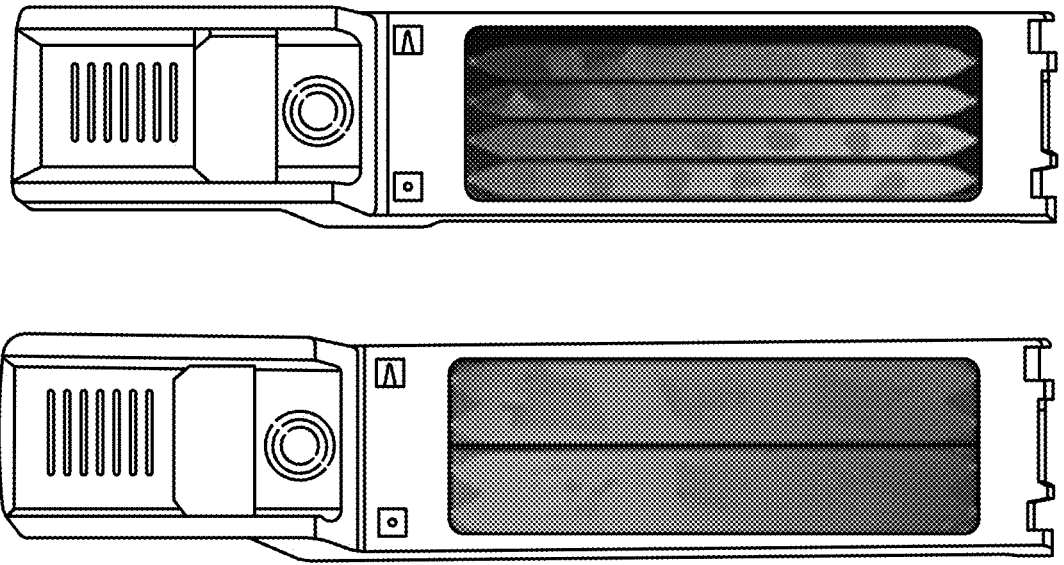
Figure 10A:
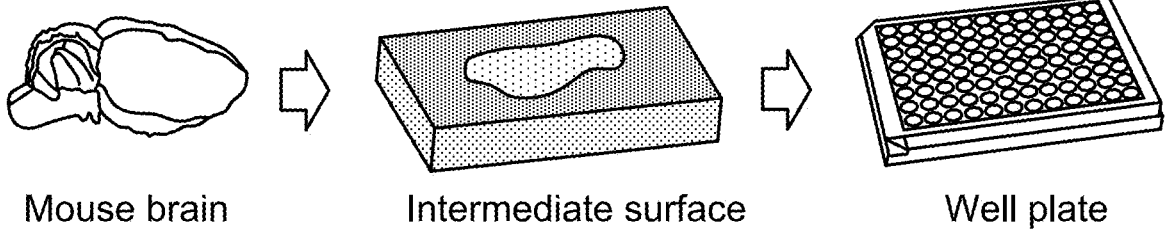
FIGS. 10A-10B.
Figure 10A:
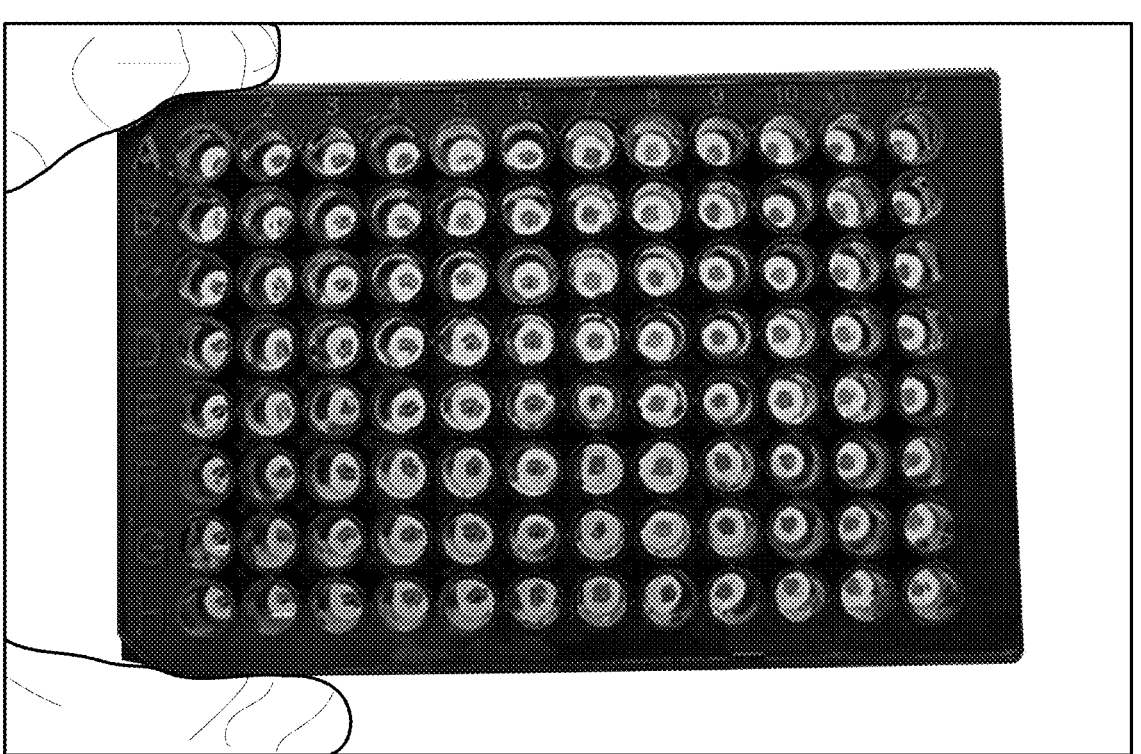
Figure 10B:
Figure 10B:
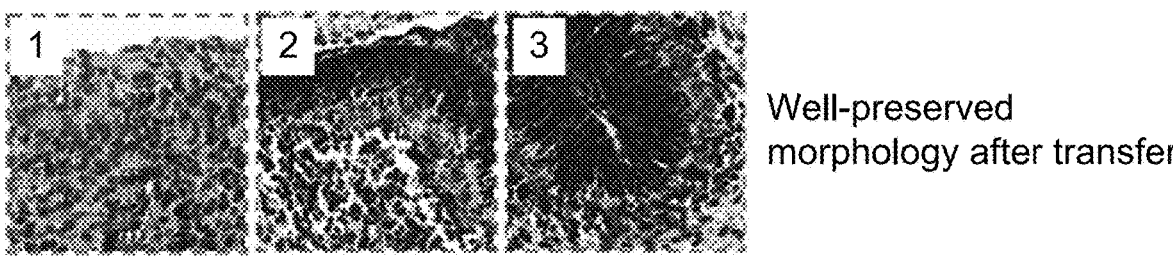

In another embodiment, a fresh frozen tissue section is prepared using a cryostat with a temperature setpoint of about −15° C. to about −25° C. The tissue section is then mounted directly onto a carrier substrate (e.g., an agarose polymeric layer) to transfer it onto a glass slide or multiwell plate, bypassing the water bath floating step that described supra for FFPE tissue section transfers. As described in FIG. 9A, the capture regions of various sizes of multiwell plates and commercial slides can vary in surface area, and each may be suitable for use in an embodiment of the invention. As the polymeric layer has reversible adherence to the fresh frozen tissue section, the issues that typically exist when mounting frozen tissue sections onto glass slides (e.g., rapid melting and binding) are overcome using the methods described herein. Alternatively, as depicted in FIGS. 9C and 9D, different punch devices may be used in conjunction with a flow cell.

The punch devices are configured to accommodate various shapes and sizes, facilitating precise cutting and manipulation of fresh frozen or FFPE preserved tissue sections. Specifically, the punch devices are engineered to include not only circular shapes but also rectangular and square configurations. For instance, embodiments of the invention may incorporate a 10.5 mm circular cutting device, suitable for larger tissue sections. Additionally, smaller circular cutting devices with a diameter of 4.5 mm are contemplated for more precise tissue extraction. See FIG. 9C as an example. Further embodiments extend to rectangular and square punch devices. A 4.5 mm×10 mm rectangular punch device is provided for elongated tissue sections, while a 10 mm×10 mm square punch device is designed for uniformly sized tissue samples. Moreover, a smaller square punch device measuring 4.5 mm×4.5 mm is included for minute tissue sections. Lastly, an embodiment with a 10 mm×17 mm rectangular punch device is introduced, offering a larger surface area for tissue extraction, thus accommodating various sizes of custom multiwell plates and/or commercial slides. These additional shapes and sizes of punch devices enhance versatility allowing for a broader range of tissue section sizes to be effectively mounted onto solid supports (e.g., glass slides or flow cells).

Various properties of the carrier substrate being used may be optimized for more effective transfer of the tissue section, including the stiffness of the hydrophilic material, for example, whether the layer forms a softer or harder gel. The thickness of the gel may also contribute to whether there is any deformation of the tissue section while it is being cut from the construct. The methods presented herein describe a novel approach to transferring fresh or preserved tissue sections onto a final medium (e.g., a receiving substrate, such as a functionalized glass slide) that minimizes tissue damage and is scalable, flexible, and also compatible with the conventional lab equipment and consumables, enabling easy adaptation and automation.

Example 2. Tissue Transfer and Surface Functionalization

Preparing a surface for tissue section mounting is a critical step in minimizing loss of tissue material during subsequent processing. For example, repeated exposure to immunohistochemistry reagents and solvents used during analysis may lead to loss of cellular or tissue section material if the tissue section is weakly bound to the surface. The conditions involved in in situ sequencing processes also involve elevated pH and incubation temperatures, in addition to the addition and removal of various fluids repeatedly. Lack of strong binding of the tissue section to the surface may therefore lead to detachment of the tissue section during in situ sequencing. Some common methods of preparing a surface for tissue section mounting, for example, a glass slide, include plasma treatment and functionalization with charged moieties. To determine the optimal surface functionalization conditions, we performed a comparison of several surface functionalization reagents, including (3-aminopropyl)triethoxysilane (APTES), (5,6-epoxyhexyl)triethoxysilane (EHTES), polyethyleneimine (PEI), or a combination thereof. Tissue sections were then transferred to the functionalized glass slide surfaces using the methods described herein, and tissue integrity cycles in the presence of various buffers performed to assess for any tissue section detachment from the treated glass slides.

Glass functionalization: Glass slides were washed three times in an acetone/ethanol bath while being sonicated. The glass slides were then oxygen plasma-treated (100 mTorr for vacuum, 1 Torr oxygen injection for 3 mins, plasma treatment at high power for 6 mins). Glass slides were then submerged in EtOH with either 1% APTES or 1% EHTES and incubated overnight. Following the overnight treatment, the slides were washed three times with EtOH and dried with an air gun. For PEI functionalization, the slides were incubated with 50 μg/mL in deionized water for 30 min followed by three washes with deionized water.

Tissue transfer and deparaffinization: Mouse intestine FFPE tissue sections were prepared and mounted on an agarose layer using the transfer methods described in Example 1. The agarose-mounted tissue sections were stored at 4° C. for about 2 months prior to being cut into 6.5 mm diameter portions (i.e., to fit in a well of a 96-well plater, see FIG. 9A for various comparative well dimensions) using a blade and transferred to each of the functionalized glass slides. 24 portions were cut and transferred to each glass slide. Following tissue section transfer, the slides were baked at 50° C. for 15 mins and the agarose layer removed. The slides were then baked at 60° C. for 30 mins and placed in dark storage at room temperature overnight. The tissue sections were then deparaffinized using xylene followed by 100% EtOH incubation. The slides were dried at 37° C. for 15 mins.

Plate assembly and rehydration: The slides were then assembled onto a bottomless 96-well plate. The slides were attached to the 96-well plate using a Kapton double-sided adhesive cut using a Silhouette Curio cutter. Samples were then serially incubated in 100%, 96%, and 70% EtOH for 5 mins each followed by incubation in deionized water.

H&E staining: Tissue sections were then fixed with 4% PFA in PBS for 30 min. Samples were then H&E stained using methods known in the art and imaged using a color camera.

Figures 8A, 8B, 8C, 8D, 8E, 8F:
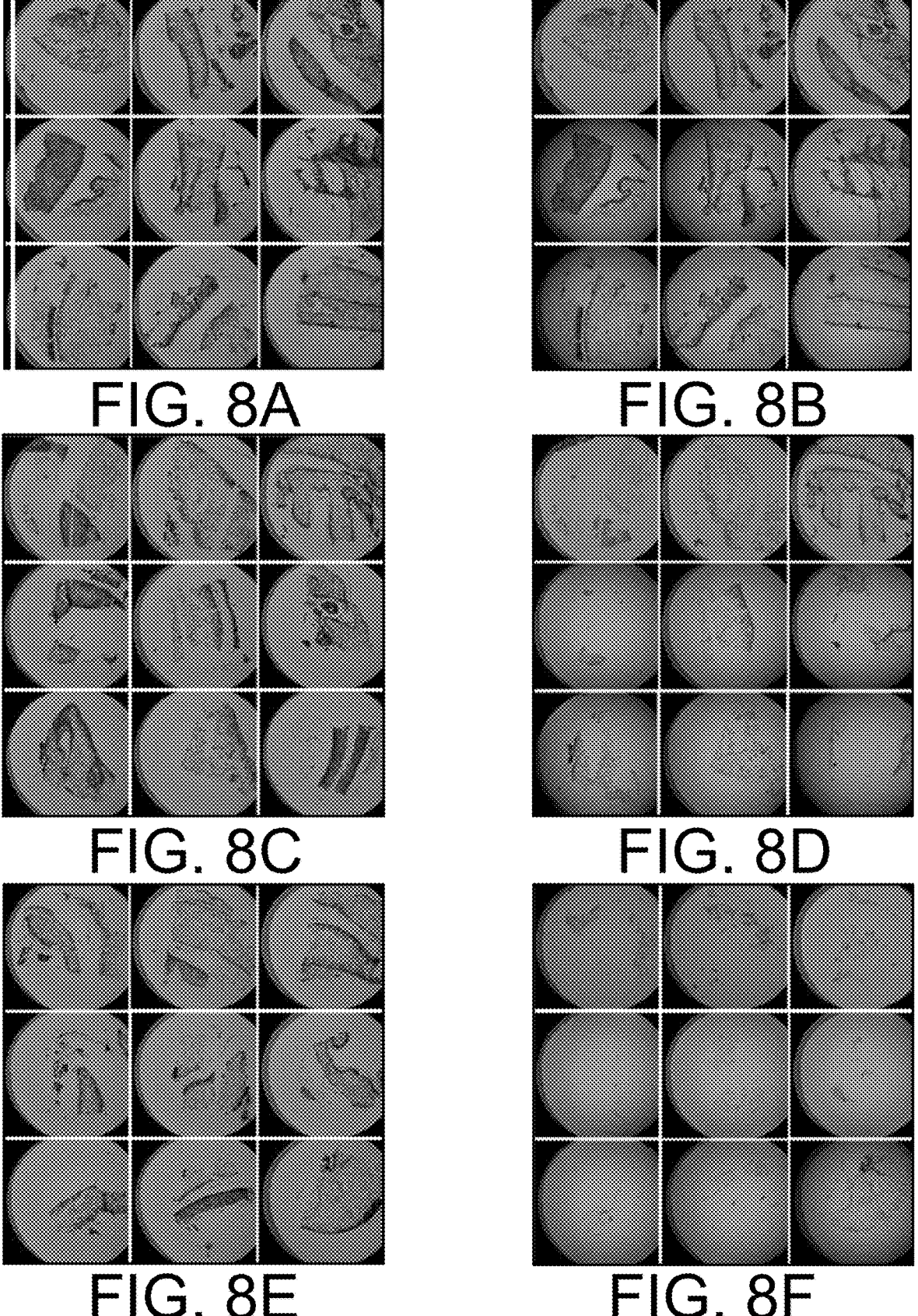

Tissue integrity tests: The 96-well plate was then subjected to 18 cycles of heat and chemical treatment, consistent with conditions useful for DNA sequencing reactions. The wells were exposed to different buffers and different reagents commonly used in amplification and sequencing reactions. For example, each cycle included a 60 sec incubation in an amplification buffer, a 240 sec incubation in sequencing buffer, a 420 sec incubation in a reducing agent, with all incubations performed at 55° C. At the end of each cycle, room temperature wash buffer was applied, and the subsequent cycle initiated. Following the integrity cycles, the tissue sections were then H&E stained and imaged using a color camera (see, FIGS. 8A-8H). FIGS. 8A-8H are images of H&E-stained tissue sections mounted on functionalized glass slides in a 96-well plate and subjected to 18 cycles of heat and chemical treatment, consistent with DNA sequencing reaction conditions, referred to as tissue integrity tests. FIG. 8A shows tissue sections mounted on an APTES-functionalized wells; and FIG. 8B shows the same tissue sections after the 18 cycles of tissue integrity testing. FIG. 8C shows tissue sections mounted on a (5,6-epoxyhexyl) triethoxysilane (EHTES)-functionalized slide, and FIG. 8D shows the same tissue sections after the 18 cycles of tissue integrity testing. FIG. 8E shows tissue sections mounted on an EHTES and polyethyleneimine (PEI)-functionalized slide, and FIG. 8F shows the same tissue sections after the 18 cycles of tissue integrity testing. FIG. 8G shows tissue sections mounted on a PEI-functionalized slide, and FIG. 8H shows the same tissue sections after the 18 cycles of tissue integrity testing.

Constructing a receiving substrate capable of surviving thermal/chemical cycling is useful for retaining the tissue during subsequent analyses. As shown in FIGS. 8A-8B, tissue sections mounted on APTES-functionalized surfaces did not appear to have any significant tissue loss or degradation after 18 cycles. In contrast, the EHTES (FIGS. 8C-8D), EHTES+PEI (FIGS. 8E-8F), and PEI (FIGS. 8G-8H) treated surfaces exhibited greater loss of tissue section material following the thermal/chemical cycling. Without wishing to be bound by any theory, the APTES-functionalized surface successfully retained a majority of the tissue due to the positive charge of the amines covalently bound to the glass which facilitate strong attachment forces and preventing tissue section detachment. PEI attaches to the tissue via an electrostatic bonding, and was likely washed away during the integrity testing. These results indicate that the tissue transfer methods of the invention are compatible with downstream in situ analytical approaches, including immunohistochemistry and multiwell plate sequencing.

Example 3. Tissue Transfer Devices

Loading a 96 well plate with tissue samples takes multiple hours, approximately 2 hours per quadrant, resulting in a at least 8 hours to fully load a 96 microtiter plate with biological samples. The systems and devices devised herein are designed to reduce the overall time and labor while minimizing the risk for sample damage. The contemplated method, as outlined in FIG. 3, is as follows: 1. Formalin-Fixed Paraffin-Embedded (FFPE) tissue sample is sectioned on microtome. 2. Tissue sections (i.e., slices) are caught on a carrier substrate as described herein (e.g., an agarose polymeric gel) in a warm water bath. 3. Using the punch device as described herein, the carrier substrate containing the tissue is cut to generate a portion of the sample having similar diameter as the punch device. 4. The portions are loaded into wells and receptacles of the receiving array, generating a plate-stack. 5. The plate-stack is baked while plunger applies pressure from top, to allow the tissue to adhere to glass bottom of the microplate. 6. The carrier substrate is removed. The microplate is ready for analysis (e.g., imaging).

The punch device may be constructed out of any suitable material (e.g., plastic, glass, aluminum, or steel). In embodiments, the punch device is configured to cut samples having 5×5 mm suitable for a 6.35×6.35 well of a multiwell container. The punch device may include one or more bores, slots, seats, notches, or other structures sized and shaped to align and/or retain the punch device within the receiving array.

The receiving array may be constructed out of any suitable material (e.g., plastic, glass, aluminum, or steel). The receiving array includes receptacles for the punch devices. In embodiments, the receptacles of the receiving array includes one or more bores, slots, seats, retention mechanisms, or other structures sized and shaped to receive, align, and secure a respective punch device within the receptacle. The receiving array may include a first and a second array to aid in retaining the punch devices.

The plunger array may be constructed out of any suitable material (e.g., plastic, glass, aluminum, or steel). In embodiments, the plunger array includes a plurality of arranged posts configured to apply pressure to the sample within the punch device. In embodiments, the plunger array is thermally stable.

Example 4. Tissue Transfer Devices for Loading a Flow Cell

There has been developed a method for tissue transfer to NGS sequencing slides (e.g., Singular Genomics sequencing slides used in flow cells) that enables easy and precise placement a plurality of unique sections (e.g., 24 unique sections, depending on the tissue section punch size) per flow cell and simplifies the overall workflow for identifying regions of interest. The method builds on standard pathology protocols for sectioning FFPE blocks on a microtome, followed by floating the individual sections in a water bath and then capturing each section using a carrier substrate (See FIGS. 7A-7C). A punch device is used as described herein to cut out the region of tissue with desired characteristics. For example, using a holder apparatus (punch tool including a plunger or actuator for retaining and expelling a punch cutting device). The cutter portion of the punch is removed, flipped, and placed in a receiving array. After the punch devices are loaded, a glass slide in a holder is aligned over the tissue array (see, for example Step 6 of FIG. 17B). The glass slide may include channels. Alternatively, the glass slide may be substantially planar and a channel slide is later affixed to the planar glass slide to form one or more channels, after the tissue samples have been deposited. The glass slide may be functionalized with a polymer and/or a coupling agent. The holder may contain an indentation, recession, or suitable pocket for receiving the glass slide. One or more retention mechanisms may be included with the holder for securing and aligning the glass slide. This work-flow allows for robust and consistent high density spatial patterning of sections in flow cells. Finally, heat (e.g., 30° C.-40° C.) and pressure (e.g., a downward force of about 5-10 N, such as the weight of a 1 kg weight placed on the assembly, 9.8 N) are applied to release the section from the carrier substrate, then baking is used as normal for tissue transfer onto glass. From this point on, tissue handling returns to standard pathology protocols. Example images of the resulting flow cells (FIG. 9D) demonstrate the placement of twenty-four 4 mm diameter and six 10 mm diameter sections per flow cell.

The total sample area that can be achieved on one slide/flow cell is unparalleled across existing spatial plat-forms. Using the methods and devices as described herein on a Singular Genomics in situ sequencing platform enables results for up to 96 unique sections (e.g., when the sections of cut tissue are about 4 mm in diameter).

Existing platforms can all only process a handful of small samples per week at peak performance, making their use expensive and often niche. The level of throughput our system provides will transform what is possible with in situ transcript and protein profiling, including enabling large cohort studies and 3D reconstructions from multiple 5 μm sections. This approach dramatically improves the workflow for tissue handling and unlocks higher density tissue place-ment than is possible on other platforms.

Embodiments

Embodiment P1. A system for manipulating a biological sample, comprising: a punch device configured to form a sample portion of the biological sample, the punch device forming an internal cavity and having a bottom edge suffi-ciently sharp to cut through the biological sample; a receiv-ing substrate; and a piston sized and shaped to fit within the internal cavity of the punch device, wherein the piston inserts into the internal cavity of the punch device to expel the sample portion from the punch device onto the receiving substrate.

Embodiment P2. The system of Embodiment P1, wherein the receiving substrate comprises a functionalized glass surface or a functionalized plastic surface.

Embodiment P3. The system of Embodiment P1, wherein the punch device comprises a top end and a bottom end, wherein said bottom end is distal to the top end and comprises the bottom edge.

Embodiment P4. The system of Embodiment P3, wherein the piston inserts into the bottom end of the punch device into the internal cavity of the punch device to expel the sample portion through the top end.

Embodiment P5. The system of Embodiment P3, wherein the diameter of the internal cavity at the top end is greater than the diameter of the internal cavity at the bottom end.

Embodiment P6. The system of Embodiment P1, the biological sample is a tissue section.

Embodiment P7. The system of Embodiment P6, wherein a thickness of the tissue section is about 1 μm to about 20 μm.

Embodiment P8. The system of Embodiment P1, wherein the biological sample is attached to a carrier substrate forming the sample-carrier construct, wherein said carrier substrate comprises agarose, amylose, amylopectin, alg-inate, gelatin, cellulose, polyolefin, polyethylene glycol, polyvinyl alcohol, and/or acrylate polymers and copolymers thereof.

Embodiment P9. The system of Embodiment P8, wherein said punch device is configured to cut through the biological sample and the carrier substrate.

Embodiment P10. The system of Embodiment P1, wherein the piston comprises a piston head, wherein the piston head is configured to contact the biological sample.

Embodiment P11. A system for manipulating a biological sample, comprising: a punch device configured to form a sample portion of the biological sample, the punch device forming an internal cavity and having a bottom edge suffi-ciently sharp to cut through the biological sample; a receiv-ing array having a receptacle sized and shaped to receive at least a portion of the punch device; a piston array having a piston sized and shaped to fit within the internal cavity of the punch device, wherein the piston inserts into the internal cavity of the punch device to expel the sample portion from the punch device into the at least one receptacle of the receiving array.

Embodiment P12. The system of Embodiment P11, wherein the receiving array includes a plurality of recep-tacles arranged in a first pattern.

Embodiment P13. The system of Embodiment P11, wherein the piston array includes a plurality of pistons arranged in a pattern that complements the first pattern such that the plurality of pistons can be inserted into the plurality of receptacles.

Embodiment P14. The system of Embodiment P11, wherein the punch device is cylindrical.

Embodiment P15. The system of Embodiment P11, wherein the bottom edge of the punch device is tapered to facilitate cutting.

Embodiment P16. The system of Embodiment P15, wherein the bottom edge of the punch device comprises a blade.

Embodiment P17. The system of Embodiment P11, wherein the sample biological sample is mounted on a carrier substrate.

Embodiment P18. The system of Embodiment P17, wherein the punch device is sufficiently sharp to cut through both the sample portion and the carrier substrate.

Embodiment P19. The system of Embodiment P11, wherein the punch device is configured to be positioned in the receptacle in the receiving array with the sample portion in the punch device and the sample portion contacting a bottom of the receptacle of the receiving array.

Embodiment P20. The system of Embodiment P11, wherein the piston array comprises a base and a plurality of pistons extending from the base.

Embodiment P21. A method of manipulating a biological sample, comprising: cutting a sample portion from the biological sample using a punch device such that the punch device contains the sample portion; mounting the punch device containing the sample portion into a receptacle of a receiving array; mounting the receiving array onto a substrate; pushing the sample portion out of the punch device using a piston so that the sample portion is positioned on the substrate.

Embodiment P22. The method of Embodiment P21, wherein cutting a sample portion comprises pressing a bottom edge of the punch device onto the biological sample so that the bottom edge cuts through the biological sample.

Embodiment P23. The method of Embodiment P22, wherein the sample portion remains inside an internal cavity of the punch device after the punch device cuts through the biological sample.

Embodiment P24. The method of Embodiment P21, wherein the piston inserts through an internal cavity of the punch device as it pushes all or a portion of the sample portion out of the punch device.

Embodiment P25. The method of Embodiment P21, further comprising removing the receiving array, piston, and punch device from the substrate.

Embodiment P26. A kit comprising a punch device configured to form a sample portion of the biological sample, the punch device forming an internal cavity and having a bottom edge sufficiently sharp to cut through the biological sample; and a piston sized and shaped to fit within the internal cavity of the punch device, wherein the piston inserts into the internal cavity of the punch device to expel the sample portion from the punch device.

Embodiment P27. A kit comprising the system of any one of Embodiments P1-P20.

Embodiment R1. A system for manipulating a biological sample, comprising: a punch device configured to form a sample portion of the biological sample, the punch device forming an internal cavity and having a bottom edge sufficiently sharp to cut through the biological sample; a receiving substrate; and a piston sized and shaped to fit within the internal cavity of the punch device, wherein the piston inserts into the internal cavity of the punch device to expel the sample portion from the punch device onto the receiving substrate.

Embodiment R2. The system of Embodiment R1, wherein the receiving substrate comprises a functionalized glass surface or a functionalized plastic surface.

Embodiment R3. The system of Embodiment R1, wherein the receiving substrate is a glass solid support.

Embodiment R4. The system of Embodiment R3, wherein the receiving substrate further comprises a resist.

Embodiment R5. The system of Embodiment R3, wherein the receiving substrate further comprises a polymer attached to the solid support, wherein the polymer is polylysine, poly(2-dimethylaminoethyl methacrylate) (PDMAEMA), chitosan, poly(amidoamine) (PAMAM), polyvinylamine (PVAm), or poly(allylamine hydrochloride) (PAH).

Embodiment R6. The system of any one of Embodiments 1 to 5, wherein the punch device comprises a top end and a bottom end, wherein said bottom end is distal to the top end and comprises the bottom edge.

Embodiment R7. The system of Embodiment R6, wherein a piston inserts into the bottom end of the punch device into the internal cavity of the punch device to expel the sample portion through the top end.

Embodiment R8. The system of Embodiment R7, wherein the piston comprises a toroid seal.

Embodiment R9. The system of Embodiment R6, wherein the diameter of the internal cavity at the top end is greater than the diameter of the internal cavity at the bottom end.

Embodiment R10. The system of any one of Embodiments R1 to R9, wherein the biological sample is a tissue section.

Embodiment R11. The system of Embodiment R10, wherein a thickness of the tissue section is about 1 μm to about 20 μm.

Embodiment R12. The system of Embodiment R10, wherein a thickness of the tissue section is about 3 μm to about 10 μm.

Embodiment R13. The system of Embodiment R10, wherein a thickness of the tissue section is about 5 μm to about 7 μm.

Embodiment R14. The system of any one of Embodiments R1 to R13, wherein the biological sample is attached to a carrier substrate forming the sample-carrier construct, wherein said carrier substrate comprises agarose, amylose, amylopectin, alginate, gelatin, cellulose, polyolefin, polyethylene glycol, polyvinyl alcohol, and/or acrylate polymers and copolymers thereof.

Embodiment R15. The system of any one of Embodiments R1 to R13, wherein the biological sample is attached to a carrier substrate forming the sample-carrier construct, wherein said carrier substrate comprises agarose, agar, amylopectin, polyvinyl alcohol, Gellan gum, or alginate.

Embodiment R16. The system of Embodiments R14 or R15, wherein said punch device is configured to cut through the biological sample and the carrier substrate.

Embodiment R17. The system of any one of Embodiments R7 to R16, wherein the piston comprises a piston head, wherein the piston head is configured to contact the biological sample.

Embodiment R18. The system of Embodiment R17, wherein the diameter of the piston head is less than the diameter of the piston.

Embodiment R19. A system for manipulating a biological sample, comprising: a punch device configured to form a sample portion of the biological sample, the punch device forming an internal cavity and having a bottom edge sufficiently sharp to cut through the biological sample; a receiving array having a receptacle sized and shaped to receive at least a portion of the punch device; a piston array having a piston sized and shaped to fit within the internal cavity of the punch device, wherein the piston inserts into the internal cavity of the punch device to expel the sample portion from the punch device into the at least one receptacle of the receiving array.

Embodiment R20. The system of Embodiment R19, wherein the receiving array includes a plurality of receptacles arranged in a first pattern.

Embodiment R21. The system of Embodiment R19 or R20, wherein the piston array includes a plurality of pistons arranged in a pattern that complements the first pattern such that the plurality of pistons can be inserted into the plurality of receptacles.

Embodiment R22. The system of any one of Embodiments R19 to R21, wherein the punch device is cylindrical, square, or rectangular.

Embodiment R23. The system of any one of Embodiments R19 to R22, wherein the bottom edge of the punch device is tapered to facilitate cutting.

Embodiment R24. The system of Embodiment R23, wherein the bottom edge of the punch device comprises a blade.

Embodiment R25. The system of any one of Embodiments R19 to R24, wherein the sample biological sample is mounted on a carrier substrate.

Embodiment R26. The system of Embodiment 25, wherein the punch device is sufficiently sharp to cut through both the sample portion and the carrier substrate.

Embodiment R27. The system of any one of Embodiments 19 to 26, wherein the punch device is configured to be positioned in the receptacle in the receiving array with the sample portion in the punch device.

Embodiment R28. The system of any one of Embodiments R19 to R27, wherein the piston array comprises a base and a plurality of pistons extending from the base.

Embodiment R29. A receiving array comprising a plurality of receptacles arranged in a pattern, wherein each receptacle is configured to retain a punch device; a plurality of punch devices, wherein each punch device comprises an internal cavity comprising a biological sample and a carrier substrate.

Embodiment R30. The receiving array of Embodiment R29, wherein the receiving array comprises an identifying feature at each receptacle, wherein the identifying feature uniquely identifies the receptacle.

Embodiment R31. The receiving array of Embodiments R29 or R30, wherein each punch device comprises an alignment feature configured to mate and align the punch device and receptacle in a proper orientation.

Embodiment R32. The receiving array of any one of Embodiments R29 to R31, wherein the receptacle and punch device are configured to haptic feedback when the punch device is retained in the receptacle.

Embodiment R33. The receiving array of any one of Embodiments R29 to R31, wherein the punch device is retained in the receptacle using a snap-fit coupling.

Embodiment R34. A method of manipulating a biological sample, comprising: cutting a sample portion from the biological sample using a punch device such that the punch device contains the sample portion; mounting the punch device containing the sample portion into a receptacle of a receiving array; mounting the receiving array onto a substrate; pushing the sample portion out of the punch device using a piston so that the sample portion is positioned on the substrate.

Embodiment R35. The method of Embodiment R34, wherein cutting a sample portion comprises pressing a bottom edge of the punch device onto the biological sample so that the bottom edge cuts through the biological sample.

Embodiment R36. The method of Embodiment R35, wherein the sample portion remains inside an internal cavity of the punch device after the punch device cuts through the biological sample.

Embodiment R37. The method of Embodiment R36, wherein the piston inserts through an internal cavity of the punch device as it pushes all or a portion of the sample portion out of the punch device.

Embodiment R38. The method of any one of Embodiments R34 to R37, further comprising removing the receiving array, piston, and punch device from the substrate.

Embodiment R39. The method of any one of Embodiments R34 to R38, wherein the substrate comprises a functionalized glass surface or a functionalized plastic surface.

Embodiment R40. The method of any one of Embodiments R34 to R38, wherein the substrate is a glass solid support.

Embodiment R41. The method of any one of Embodiments R34 to R40, wherein the substrate further comprises a resist.

Embodiment R42. The method of any one of Embodiments R34 to R41, wherein the substrate further comprises a polymer attached to the solid support, wherein the polymer is polylysine, poly(2-dimethylaminoethyl methacrylate)

(PDMAEMA), chitosan, poly(amidoamine) (PAMAM), polyvinylamine (PVAm), or poly(allylamine hydrochloride) (PAH).

Embodiment R43. The method of any one of Embodiments R34 to R42, wherein the substrate further comprises an anti-reflective coating.

Embodiment R44. A kit comprising a punch device configured to form a sample portion of the biological sample, the punch device forming an internal cavity and having a bottom edge sufficiently sharp to cut through the biological sample; and a piston sized and shaped to fit within the internal cavity of the punch device, wherein the piston inserts into the internal cavity of the punch device to expel the sample portion from the punch device.

Embodiment R45. A kit comprising the system of any one of Embodiments R1 to R28.

Embodiment 1. A system for manipulating a biological sample, comprising: a punch device configured to form a sample portion of the biological sample, the punch device forming an internal cavity and having a bottom edge sufficiently sharp to cut through the biological sample; a receiving substrate; and a piston sized and shaped to fit within the internal cavity of the punch device, wherein the piston inserts into the internal cavity of the punch device to expel the sample portion from the punch device onto the receiving substrate.

Embodiment 2. The system of Embodiment 1, wherein the receiving substrate comprises a functionalized glass surface or a functionalized plastic surface.

Embodiment 3. The system of Embodiment 1, wherein the receiving substrate is a glass solid support.

Embodiment 4. The system of Embodiment 3, wherein the receiving substrate further comprises a resist.

Embodiment 5. The system of Embodiment 3, wherein the receiving substrate further comprises polylysine, poly(2-dimethylaminoethyl methacrylate) (PDMAEMA), chitosan, poly(amidoamine) (PAMAM), polyvinylamine (PVAm), or poly(allylamine hydrochloride) (PAH).

Embodiment 6. The system of any one of Embodiments 1 to 5, wherein the punch device comprises a top end and a bottom end, wherein said bottom end is distal to the top end and comprises the bottom edge.

Embodiment 7. The system of Embodiment 6, wherein a piston inserts into the bottom end of the punch device into the internal cavity of the punch device to expel the sample portion through the top end.

Embodiment 8. The system of Embodiment 7, wherein the piston comprises a toroid seal.

Embodiment 9. The system of Embodiment 6, wherein the diameter of the internal cavity at the top end is greater than the diameter of the internal cavity at the bottom end.

Embodiment 10. The system of any one of Embodiments 1 to 9, wherein the biological sample is a tissue section.

Embodiment 11. The system of Embodiment 10, wherein a thickness of the tissue section is about 1 μm to about 20 μm.

Embodiment 12. The system of Embodiment 10, wherein a thickness of the tissue section is about 3 μm to about 10 μm.

Embodiment 13. The system of Embodiment 10, wherein a thickness of the tissue section is about 5 μm to about 7 μm.

Embodiment 14. The system of any one of Embodiments 1 to 13, wherein the biological sample is attached to a carrier substrate forming the sample-carrier construct, wherein said carrier substrate comprises agarose, amylose, amylopectin,

81 alginate, gelatin, cellulose, polyolefin, polyethylene glycol, polyvinyl alcohol, and/or acrylate polymers and copolymers thereof.

Embodiment 15. The system of any one of Embodiments 1 to 13, wherein the biological sample is attached to a carrier substrate forming the sample-carrier construct, wherein said carrier substrate comprises agarose, agar, amylopectin, polyvinyl alcohol, Gellan gum, or alginate.

Embodiment 16. The system of Embodiments 14 or 15, wherein said punch device is configured to cut through the biological sample and the carrier substrate.

Embodiment 17. The system of any one of Embodiments 7 to 16, wherein the piston comprises a piston head, wherein the piston head is configured to contact the biological sample.

Embodiment 18. The system of Embodiment 17, wherein the diameter of the piston head is less than the diameter of the piston.

Embodiment 19. A system for manipulating a biological sample, comprising: a punch device configured to form a sample portion of the biological sample, the punch device forming an internal cavity and having a bottom edge sufficiently sharp to cut through the biological sample; a receiving array having a receptacle sized and shaped to receive at least a portion of the punch device; a piston array having a piston sized and shaped to fit within the internal cavity of the punch device, wherein the piston inserts into the internal cavity of the punch device to expel the sample portion from the punch device into the at least one receptacle of the receiving array.

Embodiment 20. The system of Embodiment 19, wherein the receiving array includes a plurality of receptacles arranged in a first pattern.

Embodiment 21. The system of Embodiment 19 or 20, wherein the piston array includes a plurality of pistons arranged in a pattern that complements the first pattern such that the plurality of pistons can be inserted into the plurality of receptacles.

Embodiment 22. The system of any one of Embodiments 19 to 21, wherein the punch device is cylindrical, square, or rectangular.

Embodiment 23. The system of any one of Embodiments 19 to 22, wherein the bottom edge of the punch device is tapered to facilitate cutting.

Embodiment 24. The system of Embodiment 23, wherein the bottom edge of the punch device comprises a blade.

Embodiment 25. The system of any one of Embodiments 19 to 24, wherein the sample biological sample is mounted on a carrier substrate.

Embodiment 26. The system of Embodiment 25, wherein the punch device is sufficiently sharp to cut through both the sample portion and the carrier substrate.

Embodiment 27. The system of any one of Embodiments 19 to 26, wherein the punch device is configured to be positioned in the receptacle in the receiving array with the sample portion in the punch device.

Embodiment 28. The system of any one of Embodiments 19 to 27, wherein the piston array comprises a base and a plurality of pistons extending from the base.

Embodiment 29. A receiving array comprising a plurality of receptacles arranged in a pattern, wherein each receptacle is configured to retain a punch device; a plurality of punch devices, wherein each punch device comprises an internal cavity comprising a biological sample and a carrier substrate.

Embodiment 30. The receiving array of Embodiment 29, wherein the receiving array comprises an identifying feature at each receptacle, wherein the identifying feature uniquely identifies the receptacle.

Embodiment 31. The receiving array of Embodiments 29 or 30, wherein each punch device comprises an alignment feature configured to mate and align the punch device and receptacle in a proper orientation.

Embodiment 32. The receiving array of any one of Embodiments 29 to 31, wherein the receptacle and punch device are configured to haptic feedback when the punch device is retained in the receptacle.

Embodiment 33. The receiving array of any one of Embodiments 29 to 31, wherein the punch device is retained in the receptacle using a snap-fit coupling.

Embodiment 34. A method of manipulating a biological sample, comprising: cutting a sample portion from the biological sample using a punch device such that the punch device contains the sample portion; mounting the punch device containing the sample portion into a receptacle of a receiving array; mounting the receiving array onto a substrate; pushing the sample portion out of the punch device using a piston so that the sample portion is positioned on the substrate.

Embodiment 35. The method of Embodiment 34, wherein cutting a sample portion comprises pressing a bottom edge of the punch device onto the biological sample so that the bottom edge cuts through the biological sample.

Embodiment 36. The method of Embodiment 35, wherein the sample portion remains inside an internal cavity of the punch device after the punch device cuts through the biological sample.

Embodiment 37. The method of Embodiment 36, wherein the piston inserts through an internal cavity of the punch device as it pushes all or a portion of the sample portion out of the punch device.

Embodiment 38. The method of any one of Embodiments 34 to 37, further comprising removing the receiving array, piston, and punch device from the substrate.

Embodiment 39. The method of any one of Embodiments 34 to 38, wherein the substrate comprises a functionalized glass surface or a functionalized plastic surface.

Embodiment 40. The method of any one of Embodiments 34 to 38, wherein the substrate is a glass solid support.

Embodiment 41. The method of any one of Embodiments 34 to 40, wherein the substrate further comprises a resist.

Embodiment 42. The method of any one of Embodiments 34 to 41, wherein the substrate further comprises polylysine, poly(2-dimethylaminoethyl methacrylate) (PDMAEMA), chitosan, poly(amidoamine) (PAMAM), polyvinylamine (PVAm), or poly(allylamine hydrochloride) (PAH).

Embodiment 43. The method of any one of Embodiments 34 to 42, wherein the substrate further comprises an anti-reflective coating.

Embodiment 44. A kit comprising a punch device configured to form a sample portion of the biological sample, the punch device forming an internal cavity and having a bottom edge sufficiently sharp to cut through the biological sample; and a piston sized and shaped to fit within the internal cavity of the punch device, wherein the piston inserts into the internal cavity of the punch device to expel the sample portion from the punch device.

Embodiment 45. A kit comprising the system of any one of Embodiments 1 to 28.

What is claimed is:

1. A method for manipulating a biological sample, comprising:

positioning a punch device against a sample-carrier construct formed of a tissue section and carrier substrate, wherein the tissue is mounted on the carrier substrate, the punch device formed of an outer wall having a top edge, a bottom edge, and an internal lumen;

pushing the bottom edge of the punch device through the sample-carrier construct to cut through the sample-carrier construct such that an excised tissue section is positioned within the internal lumen of the punch device to form a loaded punch device;

positioning the loaded punch device against a slide;

positioning a piston relative to the loaded punch device so that the piston can be inserted into the loaded punch device; and using the piston to push the excised tissue section out of the loaded punch device toward the slide.

2. The method of claim 1, wherein the piston is part of a piston array formed of a plurality of pistons.

3. The method of claim 2, further comprising loading a plurality of loaded punch devices onto a corresponding plurality of pistons of the piston array.

4. The method of claim 3, wherein using the piston to push the excised tissue out of the loaded punch device toward the slide comprises using the piston array to simultaneously push excised tissues of a plurality of loaded punch devices toward the slide.

5. The method of claim 1, further comprising incubating the slide.

6. The method of claim 5, wherein the slide is incubated while the loaded punch device is positioned on the slide.

7. The method of claim 6, further comprising, after incubating the slide, removing the loaded punch device from the slide such that the excised tissue section is retained on the slide.

8. The method of claim 5, wherein the slide is incubated on a heat plate.

9. The method of claim 1, wherein positioning the loaded punch device against a slide comprises positioning a top edge of the loaded punch device against the slide.

10. The method of claim 9, wherein the loaded punch device is positioned in a perpendicular orientation relative to the slide.

11. The method of claim 1, further comprising removably attaching the punch device to a punch tool formed an outer housing that removably receives the punch device, wherein the housing serves as a handle for manipulating the punch device.

12. The method of claim 11, wherein the punch tool is a spring-loaded tool that can be actuated by a user to expel, eject, or otherwise transition the punch device toward the sample carrier-construct.

13. The method of claim 12, wherein pushing the bottom edge of the punch device through the sample-carrier construct comprises actuating the punch tool.

14. The method of claim 1, wherein the bottom edge of the punch device is sharp.

15. The method of claim 1, wherein the bottom edge of the punch device is a blade.

16. The method of claim 1, wherein the punch device is cylindrical.

17. The method of claim 16, wherein the punch device is cuboid, cylindrical, pyramidal, conical, or frustoconical.

18. The method of claim 1, wherein the slide forms part of a flow cell.

19. The method of claim 1, wherein the carrier substrate comprises agarose, gelatin, polyacrylamide, or any suitable hydrogel.

20. The method of claim 1, wherein the tissue is mounted on top of the carrier substrate.

21. The method of claim 1, wherein the tissue is mounted on top of an uppermost surface of the carrier substrate.

22. The method of claim 1, wherein the sample-carrier construct comprises interfacial water, wherein the interfacial water is positioned between the carrier substrate and the tissue section.

23. A method for manipulating a biological sample, comprising:

positioning a loaded punch device against a glass solid support, wherein said loaded punch device comprises an outer wall having a top edge, a bottom edge, and an internal lumen, wherein a tissue sample is positioned within the internal lumen;

inserting a plunger through the top edge into the internal lumen and advancing the plunger through the internal lumen to push the tissue sample to contact the glass solid support; and while the tissue sample remains in contact with the glass solid support, heating the glass solid support to a temperature of 30° C. or greater.

* * * * *